US011851486B2

(12) United States Patent
Matsuoka et al.

(10) Patent No.: US 11,851,486 B2
(45) Date of Patent: Dec. 26, 2023

(54) METHOD FOR PREDICTING AND EVALUATING THERAPEUTIC EFFECT IN DISEASES RELATED TO IL-6 AND NEUTROPHILS

(71) Applicants: NATIONAL CENTER OF NEUROLOGY AND PSYCHIATRY, Tokyo (JP); CHUGAI SEIYAKU KABUSHIKI KAISHA, Tokyo (JP)

(72) Inventors: Takako Matsuoka, Tokyo (JP); Manabu Araki, Tokyo (JP); Takashi Yamamura, Tokyo (JP)

(73) Assignees: National Center of Neurology and Psychiatry, Tokyo (JP); Chugai Seiyaku Kabushiki Kaisha, Tokyo (JP)

(*) Notice: Subject to any disclaimer, the term of this patent is extended or adjusted under 35 U.S.C. 154(b) by 94 days.

(21) Appl. No.: 16/609,053

(22) PCT Filed: May 1, 2018

(86) PCT No.: PCT/JP2018/017374
§ 371 (c)(1),
(2) Date: Oct. 28, 2019

(87) PCT Pub. No.: WO2018/203545
PCT Pub. Date: Nov. 8, 2018

(65) Prior Publication Data
US 2020/0148760 A1 May 14, 2020

(30) Foreign Application Priority Data
May 2, 2017 (JP) ................. 2017-091600

(51) Int. Cl.
C07K 16/24 (2006.01)
A61K 39/395 (2006.01)
A61K 45/06 (2006.01)

(52) U.S. Cl.
CPC .......... C07K 16/248 (2013.01); A61K 39/395 (2013.01); A61K 45/06 (2013.01)

(58) Field of Classification Search
None
See application file for complete search history.

(56) References Cited

U.S. PATENT DOCUMENTS

| 4,689,299 A | 8/1987 | Insel et al. |
| 4,801,687 A | 1/1989 | Ngo |
| 5,126,250 A | 6/1992 | McDonough et al. |
| 5,202,253 A | 4/1993 | Esmon et al. |
| 5,216,128 A | 6/1993 | Novick et al. |
| 5,322,678 A | 6/1994 | Morgan, Jr. et al. |
| 5,501,854 A | 3/1996 | Raso |
| 5,530,101 A | 6/1996 | Queen et al. |
| 5,585,089 A | 12/1996 | Queen et al. |
| 5,621,077 A | 4/1997 | Novick et al. |
| 5,639,455 A | 6/1997 | Shimamura et al. |
| 5,639,641 A | 6/1997 | Pedersen et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,830,478 A | 11/1998 | Raso et al. |
| 5,856,135 A | 1/1999 | Tsuchiya et al. |
| 5,888,510 A | 3/1999 | Kishimoto et al. |
| 5,935,935 A | 8/1999 | Connelly et al. |
| 5,945,311 A | 8/1999 | Lindhofer et al. |
| 5,990,286 A | 11/1999 | Khawli et al. |
| 6,074,642 A | 6/2000 | Wang et al. |
| 6,074,643 A | 6/2000 | Barbera-Guillem |
| 6,121,423 A | 9/2000 | Tsuchiya et al. |
| 6,261,560 B1 | 7/2001 | Tsujinaka et al. |
| 6,309,636 B1 | 10/2001 | Do Couto et al. |
| 6,329,511 B1 | 12/2001 | Vasquez et al. |
| 6,485,943 B2 | 11/2002 | Stevens et al. |
| 6,552,083 B1 | 4/2003 | Isobe et al. |
| 6,677,436 B1 | 1/2004 | Sato et al. |
| 6,723,319 B1 | 4/2004 | Ito et al. |
| 6,737,056 B1 | 5/2004 | Presta |
| 6,821,505 B2 | 11/2004 | Ward |
| 6,884,879 B1 | 4/2005 | Baca |

(Continued)

FOREIGN PATENT DOCUMENTS

AR 068564 A1 11/2009
AU 2009290162 A1 4/2010

(Continued)

OTHER PUBLICATIONS

Sanayama et al. (Arthritis & Rheumatology 2014, 66:1421-1431).*
Araki, M., et al., "Efficacy of the anti-IL-6 receptor antibody tocilizumab in neuromyelitis optica," Neurology, 82:1302-1306 (2014).
Araki, M., et al., "Latest Treatments and Prospects for Neuromyelitis Optica," The Medical Frontline, 71(6):1159-1167 (2016).
Hisanaga, K., "Neuro-Behçet disease and neuro-Sweet disease," Clin Neurol., 52:1234-1236, (2012), English abstract.
Ishikawa, S., et al., "[SAT0079] DNA Microarray of SLE Related Genes That Respond to IL-6 Blockade with Tocilizumab an Anti-IL-6 Receptor Monoclonal Antibody," Ann Rheum Dis., 65(Suppl II):474 (2006).

(Continued)

Primary Examiner — Sharon X Wen
(74) Attorney, Agent, or Firm — Nixon & Vanderhye P.C.

(57) ABSTRACT

It has become clear that the therapeutic effect of an IL-6 inhibitor for IL-6- and neutrophil-associated diseases can be predicted using the expression level of neutrophil-associated genes as an indicator. It has also become clear that an IL-6 inhibitor is effective for the treatment of IL-6- and neutrophil-associated diseases in patients with high expression levels of neutrophil-associated genes. The present invention provides a method for selecting cases of IL-6- and neutrophil-associated diseases in which treatment with an IL-6 inhibitor is effective, as well as a method for effectively treating patients with IL-6- and neutrophil-associated diseases and with high expression levels of neutrophil-associated genes.

16 Claims, 2 Drawing Sheets
Specification includes a Sequence Listing.

(56) References Cited

U.S. PATENT DOCUMENTS

| | | |
|---|---|---|
| 6,913,747 B1 | 7/2005 | Co et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |
| 7,291,721 B2 | 11/2007 | Giles-Komar et al. |
| 7,320,792 B2 | 1/2008 | Ito et al. |
| 7,414,024 B2 | 8/2008 | Blay et al. |
| 7,438,907 B2 | 10/2008 | Schuurman et al. |
| 7,479,543 B2 | 1/2009 | Tsuchiya et al. |
| 7,521,052 B2 | 4/2009 | Okuda et al. |
| 7,582,298 B2 | 9/2009 | Stevens |
| 7,745,387 B2 | 6/2010 | Bahlmann et al. |
| 7,759,472 B2 | 7/2010 | Shima et al. |
| 7,781,617 B2 | 8/2010 | Kudou et al. |
| 7,824,674 B2 | 11/2010 | Ito et al. |
| 7,825,109 B2 | 11/2010 | Nakade et al. |
| 7,884,196 B2 | 2/2011 | Lawless |
| 7,935,340 B2 | 5/2011 | Garcia-Martinez et al. |
| 7,955,590 B2 | 6/2011 | Gillies et al. |
| 8,017,121 B2 | 9/2011 | Kishimoto et al. |
| 8,217,147 B2 | 7/2012 | Stavenhagen et al. |
| 8,226,611 B2 | 7/2012 | Chen et al. |
| 8,323,649 B2 | 12/2012 | Garcia-Martinez et al. |
| 8,329,867 B2 | 12/2012 | Lazar et al. |
| 8,367,805 B2 | 2/2013 | Chamberlain et al. |
| 8,398,980 B2 | 3/2013 | Kano et al. |
| 8,470,316 B2 | 6/2013 | Yasunami |
| 8,562,991 B2 | 10/2013 | Igawa et al. |
| 8,580,264 B2 | 11/2013 | Zhang et al. |
| 8,623,355 B2 | 1/2014 | Okada et al. |
| 8,771,686 B2 | 7/2014 | Ishida |
| 8,945,558 B2 | 2/2015 | Kobara |
| 9,017,677 B2 | 4/2015 | Mihara |
| 9,029,515 B2 | 5/2015 | Pons et al. |
| 9,079,949 B1 | 7/2015 | Andrien, Jr. et al. |
| 9,096,651 B2 | 8/2015 | Igawa et al. |
| 9,228,017 B2 | 1/2016 | Igawa et al. |
| 9,260,516 B2 | 2/2016 | Nishimoto et al. |
| 9,539,322 B2 | 1/2017 | Nishimura |
| 9,688,762 B2 | 6/2017 | Igawa et al. |
| 9,725,514 B2 | 8/2017 | Takahashi et al. |
| 9,828,429 B2 | 11/2017 | Igawa et al. |
| 9,868,948 B2 | 1/2018 | Igawa et al. |
| 9,890,377 B2 | 2/2018 | Igawa et al. |
| 10,066,018 B2 | 9/2018 | Igawa et al. |
| 10,253,091 B2 | 4/2019 | Igawa et al. |
| 10,472,623 B2 | 11/2019 | Igawa et al. |
| 10,662,245 B2 | 5/2020 | Igawa et al. |
| 10,697,883 B2 | 6/2020 | Yamamura et al. |
| 10,717,781 B2 | 7/2020 | Mitsunaga et al. |
| 10,774,148 B2 | 9/2020 | Kakehi et al. |
| 10,782,290 B2 | 9/2020 | Yamamura et al. |
| 2001/0001663 A1 | 5/2001 | Kishimoto et al. |
| 2002/0098193 A1 | 7/2002 | Ward |
| 2002/0119150 A1 | 8/2002 | Kirk et al. |
| 2002/0142374 A1 | 10/2002 | Gallo et al. |
| 2002/0164339 A1 | 11/2002 | Do Couto et al. |
| 2002/0187150 A1 | 12/2002 | Mihara et al. |
| 2003/0059937 A1 | 3/2003 | Ruben et al. |
| 2003/0224397 A1 | 12/2003 | Lowman et al. |
| 2004/0018540 A1 | 1/2004 | Yamamura et al. |
| 2004/0028681 A1 | 2/2004 | Ito et al. |
| 2004/0071706 A1 | 4/2004 | Ito et al. |
| 2004/0081651 A1 | 4/2004 | Karpusas et al. |
| 2004/0133357 A1 | 7/2004 | Zhong et al. |
| 2004/0170626 A1 | 9/2004 | Schuurman et al. |
| 2004/0236080 A1 | 11/2004 | Aburatani et al. |
| 2005/0014934 A1 | 1/2005 | Hinton et al. |
| 2005/0095243 A1 | 5/2005 | Chan et al. |
| 2005/0096257 A1 | 5/2005 | Shima et al. |
| 2005/0118163 A1 | 6/2005 | Mizushima et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0158317 A1 | 7/2005 | Blay et al. |
| 2005/0182007 A1 | 8/2005 | McSwiggen et al. |
| 2005/0214278 A1 | 9/2005 | Kakuta et al. |
| 2005/0244403 A1 | 11/2005 | Lazar et al. |
| 2005/0260711 A1 | 11/2005 | Datta et al. |
| 2005/0261229 A1 | 11/2005 | Gillies et al. |
| 2005/0272634 A1 | 12/2005 | Bahlmann et al. |
| 2006/0014156 A1 | 1/2006 | Rabbani et al. |
| 2006/0019342 A1 | 1/2006 | Dall'Acqua et al. |
| 2006/0039902 A1 | 2/2006 | Young et al. |
| 2006/0063228 A1 | 3/2006 | An et al. |
| 2006/0111316 A1 | 5/2006 | Lawless |
| 2006/0134113 A1 | 6/2006 | Mihara |
| 2006/0134709 A1 | 6/2006 | Stavenhagen et al. |
| 2006/0141456 A1 | 6/2006 | Edwards et al. |
| 2006/0153860 A1 | 7/2006 | Cho et al. |
| 2006/0165696 A1 | 7/2006 | Okano et al. |
| 2006/0188502 A1 | 8/2006 | Giles-Komar et al. |
| 2006/0193772 A1 | 8/2006 | Ochiai et al. |
| 2006/0194280 A1 | 8/2006 | Dillon et al. |
| 2006/0251653 A1 | 11/2006 | Okuda et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0059312 A1 | 3/2007 | Baca et al. |
| 2007/0134234 A1 | 6/2007 | Smith et al. |
| 2007/0134242 A1 | 6/2007 | Nishimoto et al. |
| 2007/0148164 A1 | 6/2007 | Farrington et al. |
| 2007/0148169 A1 | 6/2007 | Yoshizaki et al. |
| 2007/0160598 A1 | 7/2007 | Dennis et al. |
| 2007/0167425 A1 | 7/2007 | Nakade et al. |
| 2007/0212357 A1 | 9/2007 | Pons et al. |
| 2007/0269371 A1 | 11/2007 | Krummen et al. |
| 2007/0280945 A1 | 12/2007 | Stevens et al. |
| 2008/0032923 A1 | 2/2008 | Kudou et al. |
| 2008/0075712 A1 | 3/2008 | Hattori et al. |
| 2008/0081041 A1 | 4/2008 | Nemeth |
| 2008/0145367 A1 | 6/2008 | Bove et al. |
| 2008/0166756 A1 | 7/2008 | Tsuchiya et al. |
| 2009/0022719 A1 | 1/2009 | Mihara et al. |
| 2009/0022726 A1 | 1/2009 | Zaki et al. |
| 2009/0028784 A1 | 1/2009 | Garcia-Martinez et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0263392 A1 | 10/2009 | Igawa et al. |
| 2009/0269335 A1 | 10/2009 | Nakashima et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0034811 A1 | 2/2010 | Ishida |
| 2010/0055092 A1 | 3/2010 | Hasegawa et al. |
| 2010/0061986 A1 | 3/2010 | Takahashi et al. |
| 2010/0098730 A1 | 4/2010 | Lowman et al. |
| 2010/0129357 A1 | 5/2010 | Garcia-Martinez et al. |
| 2010/0216187 A1 | 8/2010 | Lasters et al. |
| 2010/0239577 A1 | 9/2010 | Igawa et al. |
| 2010/0247523 A1 | 9/2010 | Kano et al. |
| 2010/0292443 A1 | 11/2010 | Sabbadini et al. |
| 2010/0297697 A1 | 11/2010 | Ambrosius et al. |
| 2010/0298542 A1 | 11/2010 | Igawa et al. |
| 2010/0316636 A1 | 12/2010 | Radin et al. |
| 2011/0044986 A1 | 2/2011 | Biere-Citron et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0150869 A1 | 6/2011 | Mitsunaga et al. |
| 2011/0150888 A1 | 6/2011 | Foltz et al. |
| 2011/0245473 A1 | 10/2011 | Igawa et al. |
| 2012/0045453 A1 | 2/2012 | Chen et al. |
| 2012/0065379 A1 | 3/2012 | Igawa et al. |
| 2012/0071634 A1 | 3/2012 | Igawa et al. |
| 2012/0183539 A1 | 7/2012 | Maeda |
| 2012/0238729 A1 | 9/2012 | Kuramochi et al. |

(56) References Cited

U.S. PATENT DOCUMENTS

| | | |
|---|---|---|
| 2012/0253016 A1 | 10/2012 | Igawa et al. |
| 2012/0301460 A1 | 11/2012 | Bao et al. |
| 2013/0011866 A1 | 1/2013 | Igawa et al. |
| 2013/0101581 A1 | 4/2013 | Kuramochi et al. |
| 2013/0131319 A1 | 5/2013 | Igawa et al. |
| 2013/0202588 A1 | 8/2013 | Nishimura |
| 2013/0303396 A1 | 11/2013 | Igawa et al. |
| 2013/0317203 A1 | 11/2013 | Igawa et al. |
| 2013/0336963 A1 | 12/2013 | Igawa et al. |
| 2014/0105889 A1 | 4/2014 | Igawa et al. |
| 2014/0234340 A1 | 8/2014 | Igawa et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0166666 A1 | 6/2015 | Igawa et al. |
| 2015/0274809 A1 | 10/2015 | Igawa et al. |
| 2015/0284465 A1 | 10/2015 | Igawa et al. |
| 2015/0299313 A1 | 10/2015 | Igawa et al. |
| 2015/0315278 A1 | 11/2015 | Igawa et al. |
| 2015/0353630 A1 | 12/2015 | Igawa et al. |
| 2016/0022812 A1 | 1/2016 | Mitsunaga et al. |
| 2016/0039912 A1 | 2/2016 | Mimoto et al. |
| 2016/0046693 A1 | 2/2016 | Igawa et al. |
| 2016/0139117 A1 | 5/2016 | Yamamura et al. |
| 2016/0159915 A1 | 6/2016 | Igawa et al. |
| 2016/0244526 A1 | 8/2016 | Igawa et al. |
| 2017/0002080 A1 | 1/2017 | Igawa et al. |
| 2017/0022270 A1 | 1/2017 | Igawa et al. |
| 2017/0121412 A1 | 5/2017 | Igawa et al. |
| 2017/0362304 A1 | 12/2017 | Fukuda et al. |
| 2018/0142027 A1 | 5/2018 | Igawa et al. |
| 2018/0148509 A1 | 5/2018 | Kakehi et al. |
| 2018/0149573 A1 | 5/2018 | Yamamura et al. |
| 2018/0258161 A1 | 9/2018 | Igawa et al. |
| 2019/0085085 A1 | 3/2019 | Igawa et al. |
| 2019/0211081 A1 | 7/2019 | Igawa et al. |
| 2020/0231688 A1 | 7/2020 | Igawa et al. |
| 2021/0017286 A1 | 1/2021 | Kakehi et al. |
| 2021/0206862 A1 | 7/2021 | Igawa et al. |
| 2022/0041741 A1 | 2/2022 | Igawa et al. |
| 2022/0204608 A1 | 6/2022 | Honda et al. |
| 2022/0220210 A1 | 7/2022 | Takeshita et al. |
| 2022/0306755 A1 | 9/2022 | Igawa et al. |

FOREIGN PATENT DOCUMENTS

| | | |
|---|---|---|
| CA | 1332367 C | 10/1994 |
| CA | 2203182 A1 | 5/1996 |
| CA | 2443294 A1 | 10/2002 |
| CA | 2523577 A1 | 11/2004 |
| CA | 2531482 A1 | 1/2005 |
| CA | 2549467 A1 | 7/2005 |
| CA | 2560953 A1 | 9/2005 |
| CA | 2625773 A1 | 4/2007 |
| CA | 2626688 A1 | 4/2007 |
| CA | 2647846 A1 | 10/2007 |
| CA | 2648644 A1 | 10/2007 |
| CA | 2700394 A1 | 4/2009 |
| CA | 2700498 A1 | 4/2009 |
| CA | 2700986 A1 | 4/2009 |
| CA | 2203182 C | 11/2009 |
| CA | 2549467 C | 12/2012 |
| CA | 2443294 C | 9/2013 |
| CA | 2700498 C | 1/2016 |
| CA | 2700394 C | 10/2017 |
| CN | 1164194 A | 11/1997 |
| CN | 1297357 A | 5/2001 |
| CN | 1694894 A | 11/2005 |
| CN | 1849135 A | 10/2006 |
| CN | 10374457 C | 3/2008 |
| CN | 100374159 C | 3/2008 |
| CN | 101849006 A | 9/2010 |
| CN | 101874042 A | 10/2010 |
| CN | 101849006 B | 5/2013 |
| CN | 103476793 A | 12/2013 |
| EP | 0182495 A1 | 5/1986 |
| EP | 0361902 A2 | 4/1990 |
| EP | 0361902 B1 | 2/1994 |
| EP | 0329185 B1 | 4/1994 |
| EP | 0628639 A1 | 12/1994 |
| EP | 0721783 A1 | 7/1996 |
| EP | 0783893 A1 | 7/1997 |
| EP | 0791359 A1 | 8/1997 |
| EP | 0811384 A1 | 12/1997 |
| EP | 0628639 B1 | 6/1999 |
| EP | 0931544 A2 | 7/1999 |
| EP | 0983767 A1 | 3/2000 |
| EP | 1004315 A1 | 5/2000 |
| EP | 1074268 A1 | 2/2001 |
| EP | 1108435 A1 | 6/2001 |
| EP | 1197210 A1 | 4/2002 |
| EP | 1334731 A1 | 8/2003 |
| EP | 1374900 A1 | 1/2004 |
| EP | 0721783 B1 | 3/2005 |
| EP | 1510943 A1 | 3/2005 |
| EP | 1562968 A1 | 8/2005 |
| EP | 1197210 B1 | 10/2005 |
| EP | 0811384 B1 | 6/2006 |
| EP | 1690550 A1 | 8/2006 |
| EP | 1701979 A2 | 9/2006 |
| EP | 1707215 A1 | 10/2006 |
| EP | 1712237 A2 | 10/2006 |
| EP | 1728801 A1 | 12/2006 |
| EP | 1733740 A1 | 12/2006 |
| EP | 1773391 A2 | 4/2007 |
| EP | 1601697 B1 | 5/2007 |
| EP | 1847602 A1 | 10/2007 |
| EP | 1870459 A1 | 12/2007 |
| EP | 1074268 B1 | 1/2008 |
| EP | 1334731 B2 | 2/2008 |
| EP | 1004315 B1 | 5/2008 |
| EP | 1941907 A1 | 7/2008 |
| EP | 1941908 A1 | 7/2008 |
| EP | 0983767 B1 | 9/2008 |
| EP | 1967207 A1 | 9/2008 |
| EP | 1967209 A1 | 9/2008 |
| EP | 1977763 A1 | 10/2008 |
| EP | 1990060 A1 | 11/2008 |
| EP | 2006381 A1 | 12/2008 |
| EP | 2009101 A1 | 12/2008 |
| EP | 2025346 A1 | 2/2009 |
| EP | 2031064 A1 | 3/2009 |
| EP | 2123302 A1 | 11/2009 |
| EP | 2174667 A1 | 4/2010 |
| EP | 2194066 A1 | 6/2010 |
| EP | 2196220 A1 | 6/2010 |
| EP | 2196541 A1 | 6/2010 |
| EP | 2202245 A1 | 6/2010 |
| EP | 2206775 A1 | 7/2010 |
| EP | 2236604 A1 | 10/2010 |
| EP | 2275443 A1 | 1/2011 |
| EP | 2305306 A1 | 4/2011 |
| EP | 1069185 B1 | 6/2011 |
| EP | 2330193 A1 | 6/2011 |
| EP | 2409991 A1 | 1/2012 |
| EP | 1707215 B1 | 3/2012 |
| EP | 0783893 B1 | 4/2012 |
| EP | 1967209 B1 | 6/2012 |
| EP | 1690550 B2 | 8/2012 |
| EP | 2578233 A1 | 4/2013 |
| EP | 1562968 B1 | 8/2013 |
| EP | 2639305 A1 | 9/2013 |
| EP | 2196220 B1 | 12/2014 |
| EP | 2330193 B1 | 6/2015 |
| EP | 1941908 B1 | 8/2015 |
| EP | 2123302 B1 | 12/2015 |
| EP | 2275443 B1 | 12/2015 |
| EP | 2305306 B1 | 2/2016 |
| EP | 1941907 B1 | 3/2016 |
| EP | 3009518 A1 | 4/2016 |
| EP | 1967207 B1 | 6/2016 |
| EP | 2206775 B1 | 6/2016 |
| EP | 2202245 B1 | 8/2016 |
| EP | 2174667 B1 | 1/2017 |

(56) References Cited

FOREIGN PATENT DOCUMENTS

| | | | |
|---|---|---|---|
| EP | 2578233 B1 | 4/2017 |
| EP | 3263132 A1 | 1/2018 |
| EP | 3483283 A1 | 5/2019 |
| EP | 3009518 B1 | 8/2020 |
| ES | 2276525 T3 | 6/2007 |
| FR | 2694767 A1 | 2/1994 |
| FR | 2694767 B1 | 10/1994 |
| JP | S61117457 A | 6/1986 |
| JP | S6352890 A | 3/1988 |
| JP | H0228200 A | 1/1990 |
| JP | H02163085 A | 6/1990 |
| JP | H02163096 A | 6/1990 |
| JP | H03500644 A | 2/1991 |
| JP | H06505253 A | 6/1994 |
| JP | H06237772 A | 8/1994 |
| JP | H0746998 A | 2/1995 |
| JP | H0767688 A | 3/1995 |
| JP | H07505609 A | 6/1995 |
| JP | H08208514 A | 8/1996 |
| JP | H09506001 A | 6/1997 |
| JP | H1189582 A | 4/1999 |
| JP | H11180873 A | 7/1999 |
| JP | 2002505086 A | 2/2002 |
| JP | 2002527354 A | 8/2002 |
| JP | 2003525243 A | 8/2003 |
| JP | 2004028926 A | 1/2004 |
| JP | 2004511426 A | 4/2004 |
| JP | 3525221 B2 | 5/2004 |
| JP | 3614183 B2 | 1/2005 |
| JP | 2005501514 A | 1/2005 |
| JP | 2005101105 A | 4/2005 |
| JP | 2005524606 A | 8/2005 |
| JP | 2005281235 A | 10/2005 |
| JP | 2005535341 A | 11/2005 |
| JP | 2006503001 A | 1/2006 |
| JP | 2006512087 A | 4/2006 |
| JP | 2006512325 A | 4/2006 |
| JP | 2006524685 A | 11/2006 |
| JP | 3856734 B2 | 12/2006 |
| JP | 2007525171 A | 9/2007 |
| JP | 2007528691 A | 10/2007 |
| JP | 2008037875 A | 2/2008 |
| JP | 2008037876 A | 2/2008 |
| JP | 2008538931 A | 11/2008 |
| JP | 2008297315 A | 12/2008 |
| JP | 2010505436 A | 2/2010 |
| JP | 4468578 B2 | 5/2010 |
| JP | 2010527615 A | 8/2010 |
| JP | 4609877 B2 | 1/2011 |
| JP | 4727988 B2 | 7/2011 |
| JP | 2012500020 A | 1/2012 |
| JP | 5144499 B2 | 2/2013 |
| JP | 2013518131 A | 5/2013 |
| JP | 2013165716 A | 8/2013 |
| JP | 5334319 B2 | 11/2013 |
| JP | 2013541594 A | 11/2013 |
| JP | 5484060 B2 | 5/2014 |
| JP | 5530635 B2 | 6/2014 |
| JP | 5685535 B2 | 3/2015 |
| JP | 5717624 B2 | 5/2015 |
| JP | 2015130883 A | 7/2015 |
| JP | 5787446 B2 | 9/2015 |
| KR | 20060010765 A | 2/2006 |
| KR | 20070035482 A | 3/2007 |
| KR | 20070068385 A | 6/2007 |
| KR | 20080098504 A | 11/2008 |
| KR | 20100074220 A | 7/2010 |
| KR | 20100074221 A | 7/2010 |
| RU | 2127117 C1 | 3/1999 |
| RU | 2147442 C1 | 4/2000 |
| RU | 2195690 C2 | 12/2002 |
| RU | 2195960 C2 | 1/2003 |
| RU | 2225721 C2 | 3/2004 |
| RU | 2232773 C2 | 7/2004 |
| RU | 2266298 C2 | 12/2005 |
| RU | 2430111 C1 | 9/2011 |
| RU | 2010116152 A | 11/2011 |
| TW | 200803895 A | 1/2008 |
| TW | 201021829 A | 6/2010 |
| TW | 201302219 A1 | 1/2013 |
| WO | WO-8901343 A1 | 2/1989 |
| WO | WO-9112023 A1 | 8/1991 |
| WO | WO-9212729 A1 | 8/1992 |
| WO | WO-9219759 A1 | 11/1992 |
| WO | WO-9308817 A1 | 5/1993 |
| WO | WO-9420488 A1 | 9/1994 |
| WO | WO-9428159 A1 | 12/1994 |
| WO | WO-9509873 A1 | 4/1995 |
| WO | WO-9514710 A1 | 6/1995 |
| WO | WO-9533844 A1 | 12/1995 |
| WO | WO-9611020 A1 | 4/1996 |
| WO | WO-9612503 A1 | 5/1996 |
| WO | WO-9625174 A1 | 8/1996 |
| WO | WO-9627011 A1 | 9/1996 |
| WO | WO-9709351 A1 | 3/1997 |
| WO | WO-9720858 A1 | 6/1997 |
| WO | WO-9803546 A1 | 1/1998 |
| WO | WO-9836061 A2 | 8/1998 |
| WO | WO-9842377 A1 | 10/1998 |
| WO | WO-9908707 A1 | 2/1999 |
| WO | WO-9918212 A1 | 4/1999 |
| WO | WO-9943713 A1 | 9/1999 |
| WO | WO-9947170 A1 | 9/1999 |
| WO | WO-9951743 A1 | 10/1999 |
| WO | WO-9958572 A1 | 11/1999 |
| WO | WO-9960013 A2 | 11/1999 |
| WO | WO-0010607 A1 | 3/2000 |
| WO | WO-0014220 A1 | 3/2000 |
| WO | WO-0105394 A1 | 1/2001 |
| WO | WO-0130854 A2 | 5/2001 |
| WO | WO-0145678 A2 | 6/2001 |
| WO | WO-0164214 A2 | 9/2001 |
| WO | WO-0182899 A2 | 11/2001 |
| WO | WO-0203492 A1 | 1/2002 |
| WO | WO-0234292 A1 | 5/2002 |
| WO | WO-02060919 A2 | 8/2002 |
| WO | WO-02072605 A2 | 9/2002 |
| WO | WO-02080969 A1 | 10/2002 |
| WO | WO-03000883 A1 | 1/2003 |
| WO | WO-03020949 A2 | 3/2003 |
| WO | WO-03048205 A2 | 6/2003 |
| WO | WO-03068259 A1 | 8/2003 |
| WO | WO-03068260 A1 | 8/2003 |
| WO | WO-03105757 A2 | 12/2003 |
| WO | WO-03105861 A1 | 12/2003 |
| WO | WO-2004007701 A1 | 1/2004 |
| WO | WO-2004016740 A2 | 2/2004 |
| WO | WO-2004035752 A2 | 4/2004 |
| WO | WO-2004039826 A1 | 5/2004 |
| WO | WO-2004045507 A2 | 6/2004 |
| WO | WO-2004045512 A2 | 6/2004 |
| WO | WO-2004045520 A2 | 6/2004 |
| WO | WO-2004068931 A2 | 8/2004 |
| WO | WO-2004071404 A2 | 8/2004 |
| WO | WO-2004073741 A1 | 9/2004 |
| WO | WO-2004092219 A2 | 10/2004 |
| WO | WO-2004096273 A1 | 11/2004 |
| WO | WO-2004113387 A2 | 12/2004 |
| WO | WO-2005005604 A2 | 1/2005 |
| WO | WO-2005028514 A1 | 3/2005 |
| WO | WO-2005035753 A1 | 4/2005 |
| WO | WO-2005035754 A1 | 4/2005 |
| WO | WO-2005035756 A1 | 4/2005 |
| WO | WO-2005037315 A1 | 4/2005 |
| WO | WO-2005044848 A1 | 5/2005 |
| WO | WO-2005047327 A2 | 5/2005 |
| WO | WO-2005056606 A2 | 6/2005 |
| WO | WO-2005059106 A2 | 6/2005 |
| WO | WO-2005061000 A1 | 7/2005 |
| WO | WO-2005067620 A2 | 7/2005 |
| WO | WO-2005080429 A2 | 9/2005 |
| WO | WO-2005090405 A1 | 9/2005 |
| WO | WO-2005092925 A2 | 10/2005 |
| WO | WO-2005107800 A1 | 11/2005 |

(56) References Cited

FOREIGN PATENT DOCUMENTS

| | | |
|---|---|---|
| WO | WO-2005112564 A2 | 12/2005 |
| WO | WO-2005123126 A2 | 12/2005 |
| WO | WO-2006004663 A2 | 1/2006 |
| WO | WO-2006009092 A1 | 1/2006 |
| WO | WO-2006019447 A1 | 2/2006 |
| WO | WO-2006023144 A2 | 3/2006 |
| WO | WO-2006030200 A1 | 3/2006 |
| WO | WO-2006030220 A1 | 3/2006 |
| WO | WO-2006044908 A2 | 4/2006 |
| WO | WO-2006047340 A2 | 5/2006 |
| WO | WO-2006047350 A2 | 5/2006 |
| WO | WO-2006050491 A2 | 5/2006 |
| WO | WO-2006066598 A2 | 6/2006 |
| WO | WO-2006067913 A1 | 6/2006 |
| WO | WO-2006070286 A2 | 7/2006 |
| WO | WO-2006071877 A2 | 7/2006 |
| WO | WO-2006072954 A2 | 7/2006 |
| WO | WO-2006075668 A1 | 7/2006 |
| WO | WO-2006106905 A1 | 10/2006 |
| WO | WO-2006109592 A1 | 10/2006 |
| WO | WO-2006119115 A2 | 11/2006 |
| WO | WO-2006121852 A2 | 11/2006 |
| WO | WO-2007024535 A2 | 3/2007 |
| WO | WO-2007043641 A1 | 4/2007 |
| WO | WO-2007046489 A1 | 4/2007 |
| WO | WO-2007058194 A1 | 5/2007 |
| WO | WO-2007060411 A1 | 5/2007 |
| WO | WO-2007061029 A1 | 5/2007 |
| WO | WO-2007067976 A2 | 6/2007 |
| WO | WO-2007074880 A1 | 7/2007 |
| WO | WO-2007076524 A1 | 7/2007 |
| WO | WO-2007076927 A1 | 7/2007 |
| WO | WO-2007086490 A1 | 8/2007 |
| WO | WO-2007092772 A2 | 8/2007 |
| WO | WO-2007108559 A1 | 9/2007 |
| WO | WO-2007114319 A1 | 10/2007 |
| WO | WO-2007114325 A1 | 10/2007 |
| WO | WO-2007116962 A1 | 10/2007 |
| WO | WO-2007137984 A2 | 12/2007 |
| WO | WO-2007142325 A1 | 12/2007 |
| WO | WO-2007143168 A2 | 12/2007 |
| WO | WO-2008020079 A1 | 2/2008 |
| WO | WO-2008043822 A2 | 4/2008 |
| WO | WO-2008060785 A2 | 5/2008 |
| WO | WO-2008090901 A1 | 7/2008 |
| WO | WO-2008092117 A2 | 7/2008 |
| WO | WO-2008144763 A2 | 11/2008 |
| WO | WO-2008145141 A1 | 12/2008 |
| WO | WO-2009006338 A1 | 1/2009 |
| WO | WO-2009010539 A2 | 1/2009 |
| WO | WO-2009014263 A1 | 1/2009 |
| WO | WO-2009036209 A2 | 3/2009 |
| WO | WO-2009041062 A1 | 4/2009 |
| WO | WO-2009041613 A1 | 4/2009 |
| WO | WO-2009041621 A1 | 4/2009 |
| WO | WO-2009041643 A1 | 4/2009 |
| WO | WO-2009041734 A1 | 4/2009 |
| WO | WO-2009044774 A1 | 4/2009 |
| WO | WO-2009052439 A2 | 4/2009 |
| WO | WO-2009072604 A1 | 6/2009 |
| WO | WO-2009100309 A2 | 8/2009 |
| WO | WO-2009125825 A1 | 10/2009 |
| WO | WO-2009139822 A1 | 11/2009 |
| WO | WO-2009148148 A1 | 12/2009 |
| WO | WO-2010021697 A2 | 2/2010 |
| WO | WO-2010035769 A1 | 4/2010 |
| WO | WO-2010065078 A1 | 6/2010 |
| WO | WO-2010106812 A1 | 9/2010 |
| WO | WO-2010107108 A1 | 9/2010 |
| WO | WO-2010107109 A1 | 9/2010 |
| WO | WO-2010107110 A1 | 9/2010 |
| WO | WO-2011013786 A1 | 2/2011 |
| WO | WO-2011094593 A2 | 8/2011 |
| WO | WO-2011111007 A2 | 9/2011 |
| WO | WO-2011149046 A1 | 12/2011 |
| WO | WO-2011149051 A1 | 12/2011 |
| WO | WO-2011154139 A2 | 12/2011 |
| WO | WO-2012063875 A1 | 5/2012 |
| WO | WO-2012064627 A2 | 5/2012 |
| WO | WO-2012073992 A1 | 6/2012 |
| WO | WO-2012118750 A2 | 9/2012 |
| WO | WO-2014028354 A1 | 2/2014 |
| WO | WO-2014144080 A2 | 9/2014 |
| WO | WO-2014144575 A1 | 9/2014 |
| WO | WO-2014200018 A1 | 12/2014 |
| WO | WO-2016027859 A1 | 2/2016 |
| WO | WO-2016104777 A1 | 6/2016 |
| WO | WO-2016136933 A1 | 9/2016 |
| WO | WO-2016186154 A1 | 11/2016 |
| WO | WO-2018008750 A1 | 1/2018 |
| WO | WO-2018203545 A1 | 11/2018 |
| WO | WO2019151418 A1 | 8/2019 |
| WO | WO-2020202839 A1 | 10/2020 |
| WO | WO-2020213665 A1 | 10/2020 |

OTHER PUBLICATIONS

International Search Report dated Jul. 31, 2018 in International Patent Application No. PCT/JP2018/017374.

Jacob, A., et al., "Detrimental role of granulocyte-colony stimulating factor in neuromyelitis optica: clinical case and histological evidence," Mult Scler J., 18(12):1801-1803 (2012).

Nishomoto, N., et al., "Expressions of Immune Response Related Genes Were Normalised After Tocilizumab Treatment in Rheumatoid Arthritis (RA) Patients," Ann Rheum Diseases, 71(Suppl 3):380, Abstract FRI0198 (2013).

Pérez-Sánchez, C., et al., "Diagnostic potential of NETosis-derived products for disease activity, atherosclerosis and therapeutic effectiveness in Rheumatoid Arthritis patients," J Autoimmun., 82:31-40 (2017).

Ruiz-Limón, P., et al., "Tocilizumab improves the proatherothrombotic profile of rheumatoid arthritis patients modulating endothelial dysfunction, NETosis, and inflammation," Transl Res., 183:87-103 (2017).

Saadoun, S., et al., "Neutrophil Protease Inhibition Reduces Neuromyelitis Optica-Immunoglobulin G-Induced Damage in Mouse Brain," Ann Neurol., 71:323-333 (2012).

Tanaka, T., et al., "Therapeutic Targeting of the Interleukin-6 Receptor," Annu Rev Pharmacol Toxicol., 52:199-219 (2012).

Yamamura, T., "Anti-IL-6 receptor antibody therapy against Neuromyelitis Optica (NMO)," The 34th Annual Meeting of the Japanese Society of Neurological Therapeutics, Nov. 4, 2016.

Yamamura, T., "Anti-IL-6 receptor therapy for neuromyelitis optica," Neuro Therapeut., 33(5):S120 (2016).

Yamamura, T., "Treatment failures in NMO are due to specific immunologic mechanisms," 9th Annual International Roundtable Conference on NMO, Los Angeles, Mar. 13-14, 2017.

Abiatari, I., et al., "Consensus Transcriptome Signature of Perineural Invasion in Pancreatic Carcinoma," Molecular Cancer Therapeutics 8:1494-1504 (2009).

Aboud-Pirak, E., et al., "Binding and Endocytosis of a Monoclonal Antibody to a High Molecular Weight Human Milk Fat Globule Membrane-associated Antigen by Cultured MCF-7 Breast Carcinoma Cells," Cancer Research 48(11):3188-3196 (1988).

Actemra (tocilizumab), Highlights of Prescribing Information, as revised in Aug. 2017 (1 page).

Adams, C.W., et al., "Humanization of a Recombinant Monoclonal Antibody to Produce a Therapeutic HER Dimerization Inhibitor, Pertuzumab," Cancer Immunology, Immunotherapy, 55(6):717-727 (2006).

Akira, S. and Kishimoto T., "The Evidence for Interleukin-6 as an Autocrine Growth Factor in Malignancy," Seminars in Cancer Biology 3(1):17-26 (1992).

Akira, S., et al., "Interleukin-6 in Biology and Medicine," Advances in Immunology 54:1-78 (1993).

Algonomics—TripoleR applications [Online], Retrieved from the Internet on Feb. 29, 2012: http://www.algonomics.com/proteinengineering/tripole_applications.php, 2 pages, available online on Feb. 21, 2009.

(56) References Cited

OTHER PUBLICATIONS

Allen, M.J., et al., "Interchain Disulfide Bonding in Human IgG2 Antibodies Probed by Site-Directed Mutagenesis," Biochemistry 48(17):3755-3766 (2009).
Almagro, J.C. and Fransson, J., "Humanization of Antibodies," Frontiers in BioScience 13:1619-1633 (2008).
Almand, B., et al., "Clinical Significance of Defective Dendritic Cell Differentiation in Cancer," Clin Cancer Res., 6:1755-1766 (2000).
Almand, B., et al., "Increased Production of Immature Myeloid Cells in Cancer Patients: A Mechanism of Immunosuppression in Cancer," J Immunol., 166:678-689 (2001).
Alvarez, B., et al.,"Tumor Necrosis Factor-a Exerts Interleukin-6-Dependent and -Independent Effects on Cultured Skeletal Muscle Cells," Biochimica et Biophysica Acta (BBA), 1542(1-3): 66-72 (2002).
Amendment and Reply to Office Action filed Jul. 11, 2013, in U.S. Appl. No. 12/085,065, Okada et al., filed Jun. 1, 2009.
Amendment and Reply to Office Action filed Jun. 11, 2012, in U.S. Appl. No. 12/090,061, Yasunami, filed Mar. 6, 2009.
Amendment and Reply to Office Action filed Jan. 26, 2012, in U.S. Appl. No. 12/680,087, Igawa et al., filed Jan. 3, 2011.
Amendment and Reply to Office Action filed Apr. 5, 2011, in U.S. Appl. No. 12/090,676, Kobara et al., filed Feb. 25, 2009.
Amendment and Reply to Office Action filed Mar. 12, 2013 in U.S. Appl. No. 12/996,162, Mitsunaga et al., filed Mar. 7, 2011.
Amendment and Reply to Office Action filed Feb. 15, 2012 in U.S. Appl. No. 12/161,733, Ishida, filed Mar. 9, 2009.
Amendment and Reply to Office Action filed Jan. 15, 2013 in U.S. Appl. No. 12/524,041, Takahashi et al., filed Sep. 18, 2009.
Amendment and Reply to Office Action filed Sep. 25, 2013 in U.S. Appl. No. 13/387,292, Maeda, filed Apr. 3, 2012.
Amendment and Reply to Restriction Requirement filed Oct. 17, 2012 in U.S. Appl. No. 12/680,112, Igawa et al., filed Jun. 23, 2010.
Amendment and Reply to Office Action dated Aug. 27, 2012 in U.S. Appl. No. 12/680,112, Igawa et al., filed Jun. 23, 2010.
Amendment and Reply to Office Action filed Jul. 2, 2013 in U.S. Appl. No. 12/679,922, Igawa et al., filed Oct. 1, 2010.
Amendment in Reply to Office Action filed Oct. 9, 2012 in U.S. Appl. No. 12/085,065, Okada et al., filed Jun. 1, 2009.
Amendment in Reply to Office Action filed Sep. 11, 2012 in U.S. Appl. No. 12/295,039, Igawa et al., filed Jan. 20, 2009.
Amendment in Reply to Office Action filed Jan. 26, 2012 in U.S. Appl. No. 12/296,193, Nishimoto et al., filed Apr. 15, 2009.
Amendment in Reply to Office Action filed May 14, 2013 in U.S. Appl. No. 13/595,139, Igawa et al., filed Aug. 27, 2012.
Amersham Biosciences, "Affinity Chromatography: Principles and Methods," Edition AD 137:16-18 (2002).
Amersham Biosciences, "Antibody Purification Handbook," Edition 18-1037-46, accessed at http://www.promix.ru/manuf/ge/chrom/lit/Antibody Purification.pdf [online], accessed on Nov. 5, 2015.
Anchin, J.M., et al.,"Recognition of Superpotent Sweetener Ligands by a Library of Monoclonal Antibodies," Journal of Molecular Recognition, 10(5): 235-242 (1997).
Ando, K, et al., "Tocilizumab, a Proposed Therapy for the Cachexia of Interleukin6-expressing Lung Cancer," PLoS One, 9(7):e102436 (2014).
Annual Report 2012, "Integrated Edition Including CSR Report," Chugai Pharmaceutical Co., Ltd., 154 (Mar. 2013).
Ano, S., et al., "Transcription Factors GATA-3 and RORγt Are Important for Determining the Phenotype of Allergic Airway Inflammation in a Murine Model of Asthma," J Immunol., 190:1056-1065 (2013).
Anonymous, "Interleukin 6," Wikipedia, Feb. 22, 2019, XP055598802, accessed at https://protect-us.mimecast.com/s/6UxpCmZ28nsApl8JuGhTki?domain=en.wikiped ia.org, accessed on Jun. 24, 2019, 20 pages.
Martin, A.C.R., Antibodies from www.bioinf.org.uk: Dr. Andrew C.R. Martin's Group, downloaded Jul. 11, 2018, 9 pages.

Anzctr, registered trial, Trial Review, Reg. No. ACTRN12614000123640, Registered Feb. 3, 2014.
Araki, M., et al., "Clinical Improvement in a Patient With Neuromyelitis Optica Following Therapy With the Anti-il-6 Receptor Monoclonal Antibody Tocilizumab," Modern Rheumatology, 23(4):827-831 (2013).
Aricha, R., et al.."Blocking of Il-6 Suppresses Experimental Autoimmune Myasthenia Gravis," Journal of Autoimmunity, 36(2): 135-141 (2011).
Arima, Y., et al., "Regional Neural Activation Defines a Gateway for Autoreactive T Cells to Cross the Blood-Brain Barrier," Cell, 148:447-457 (2012).
Armour, K.L., et al., "Recombinant Human IgG Molecules Lacking Fcgamma Receptor I Binding and Monocyte Triggering Activities," European Journal of Immunology 29(8):2613-2624 (1999).
Armstrong, C.A., et al., "Melanoma-derived Interleukin 6 Inhibits in Vivo Melanoma Growth," The Journal of Investigative Dermatology, 102(3):278-284 (1994).
Ashizawa, T., et al., "Clinical Significance of lnterleukin-6 (IL-6) in the Spread of Gastric Cancer: Role of IL-6 as a Prognostic Factor", Gastric Cancer 8:124-131 (2005).
Audenet, F., et al., "The Evolution of Bladder Cancer Genomics: What Have We Learned and How Can We Use It?," Urologic Oncology 36(7):313-320 (2018).
Balint et al., "Alterations of the Peripheral B Cell Compartment in Pediatric-onset Multiple Sclerosis," Journal of Neurology, 258, S202, Abstract No. P732 (2011).
Balint, R.F., et al., "Antibody Engineering by Parsimonious Mutagenesis," Gene, 137(1):109-118 (1993).
Barkhof, F., et al., "Comparison of MRI Criteria at First Presentation to Predict Conversion to Clinically Definite Multiple Sclerosis", Brain 120:2059-2069 (1997).
Barrabes, S., et al., "Effect of Sialic Acid Content on Glycoprotein Pi Analyzed by Two-Dimensional Electrophoresis," Electrophoresis, 31(17):2903-2912 (2010).
Bartelds, G.M., et al., "Clinical Response to Adalimumab: Relationship to Anti-Adalimumab Antibodies and Serum Adalimumab Concentrations in Rheumatoid Arthritis," Annals of the Rheumatic Diseases, 66(7):921-926 (2007).
Barton-Davis, E.R., et al., "Viral Mediated Expression of Insulin-Like Growth Factor I Blocks the Aging-related Loss of Skeletal Muscle Function," Proceedings of the National Academy of Sciences of the United States of America 95(26):15603-15607 (1998).
Batra, S.K., et al., "Pharmacokinetics and Biodistribution of Genetically Engineered Antibodies," Current Opinion in Biotechnology, 13(6):603-608 (2002).
Bayry, J., et al., "Immuno Affinity Purification of Foot and Mouth Disease Virus Type-Specific Antibodies Using Recombinant Protein Adsorbed to Polystyrene Wells," Journal of Virological Methods 81(1-2):21-30 (1999).
Beck, A., et al., "Strategies and Challenges for the Next Generation of Therapeutic Antibodies," Nature Reviews Immunology 10(5):345-352 (2010).
Beck, J., et al., "Brief Report: Alleviation of Systemic Manifestations of Castleman's Disease by Monoclonal Anti-interleukin-6 Antibody," The New England Journal of Medicine, 330(9):602-605 (1994).
Becker, Y., "Molecular Immunological Approaches to Biotherapy of Human Cancers—A Review, Hypothesis and Implications", Anticancer Research 29:1113-1134 (2006).
Bellomo, R.,"The Cytokine Network in the Critically Ill," Anaesthesia and Intensive Care, 20(3): 288-302 (1992).
Benda, B and KORSGREN, O., "Interleukin-6 in Islet Xenograft Rejection," Transplant international, 14(2):63-71 (2001).
Bender, N.K., et al., "Immunogenicity, Efficacy and Adverse Events of Adalimumab in RA Patients," Rheumatology International, 27(3):269-274 (2007).
Berger, T., et al., "Disruption of the Lcn2 Gene in Mice Suppresses Primary Mammary Tumor Formation but Does Not Decrease Lung Metastasis", Proceedings of the National Academy of Sciences of the United States of America 107:2995-3000 (2010).
Bertagnolli, M.M., et al., "IL-4-Supported Induction of Cytolytic T Lymphocytes Requires IL-2 and IL-6," Cellular Immunology 133(2):327-341 (1991).

(56) References Cited

OTHER PUBLICATIONS

Besada, E., et al.."Potential Patient Benefit of a Subcutaneous Formulation of Tocilizumab for the Treatment of Rheumatoid Arthritis: a Critical Review," Patient Preference and Adherence, 8:1051-1059 (2014).

Besse, B., et al., "Phase 2 Study of Frontline Bortezomib in Patients With Advanced Non-small Cell Lung Cancer," Lung Cancer, 76(1):78-83 (2012).

Bian, H., et al., "Discovery of Promiscuous HLA-II-Restricted T Cell Epitopes With TEPITOPE," Methods 34(4):468-475 (2004).

Binding Data for Rituximab (submitted by the Opponent during EP opposition procedure for EP2708558 and posted by EPO on Jan. 15, 2019), 6 pages.

Binz, H.K., et al., "Engineering Novel Binding Proteins From Nonimmunoglobulin Domains," Nature Biotechnology, 23(10):1257-1268 (2005).

Biswas, P.S., et al., "Involvement of IL-6 in the Paracrine Production of VEGF in Ocular HSV-1 Infection," Experimental Eye Research 82(1):46-54 (2006).

Bogdanovich, S., et al.."Functional Improvement of Dystrophic Muscle by Myostatin Blockade," Nature, 420: 418-421 (2002).

Bonapace, L., et al., "Cessation of CCL2 Inhibition Accelerates Breast Cancer Metastasis by Promoting Angiogenesis," Nature 515(7525):130-133 (2014).

Bond, M., et al., "Synergistic Upregulation of Metalloproteinase-9 by Growth Factors and Inflammatory Cytokines: an Absolute Requirement for Transcription Factor Nf-kappa B," FEBS Letters, 435(1):29-34 (1998).

Borg, A.J., et al., "15-Deoxyspergualin Inhibits Interleukin 6 Production in in Vitro Stimulated Human Lymphocytes", Transplant Immunology 4:133-143 (1996).

Bork, P. and Bairoch, A., "Go Hunting in Sequence Databases But Watch Out for the Traps," Trends in Genetics 12(10):425-427 (1996).

Bork, P., "Powers and Pitfalls in Sequence Analysis: the 70% Hurdle," Genome Research, 10(4): 398-400 (2000).

Borsellino, N., et al., "Blocking Signaling Through the Gp130 Receptor Chain by Interleukin-6 and Oncostatin M Inhibits Pc-3 Cell Growth and Sensitizes the Tumor Cells to Etoposide and Cisplatin-mediated Cytotoxicity," Cancer, 85(1):134-144 (1999).

Branden, C. and Tooze, J., "Recognition of Foreign Molecules by the Immune System," Introduction to Protein Structure, 2nd Edition:299-232 (1999).

Brenner, S.E., "Errors in Genome Annotation," Trends in Genetics 15(4):132-133 (1999).

Bromberg, "The IL-6/Jak/Stat3 Pathway: Targeting Metastatic Breast Cancer Research Update," www.mountainsofhopefoundation.org, 4 pages (2009).

Brown, M., et al., "Tolerance of Single, but Not Multiple, Amino Acid Replacements in Antibody Vh Cdr 2: a Means of Minimizing B Cell Wastage From Somatic Hypermutation?," Journal of Immunology 156(9):3285-3291 (1996).

Brown, N.L., et al., "A Study of the Interactions Between an IgG-Binding Domain Based on the B Domain of Staphylococcal Protein a and Rabbit IgG," Molecular Biotechnology 10(1):9-16 (1998).

Burmeister, W.P., et al.,"Crystal Structure of the Complex of Rat Neonatal Fc Receptor With Fc," Nature, 372: 379-383 (1994).

Burska, A., et al., "Gene expression analysis in RA: towards personalized medicine," Pharmacogenomics J., 14:93-106 (2014).

Cabillic, F., et al., "Interleukin-6 and Vascular Endothelial Growth Factor Release by Renal Cell Carcinoma Cells Impedes Lymphocyte-dendritic Cell Cross-talk," Clinical and Experimental Immunology, 146(3):518-523 (2006).

Campbell, l,L., et al., "Essential Role for Interferon-gamma and Interleukin-6 in Autoimmune Insulin-dependent Diabetes in NOD/Wehi Mice", The Journal of Clinical Investigation 87:739-742 (1991).

Campbell, I.L., et al., "Evidence for IL-6 Production by and Effects on the Pancreatic Beta-Cell," Journal of Immunology 143(4):1188-1191 (1989).

Campo, S., et al.."Comparative Activity of Sant7 and Anti-IL-6, Il-6R Monoclonal Antibodies in a Murine Model of B-cell Lymphoma," Cytokine, 31(5): 368-374 (2005).

Campochiaro, P.A.,"Retinal and Choroidal Neovascularization," Journal of Cellular Physiology, 184(3):301-310 (2000).

Canfield, S.M. and Morrison, S.L., "The Binding Affinity of Human IgG for Its High Affinity Fc Receptor is Determined by Multiple Amino Acids in the CH2 Domain and is Modulated by the Hinge Region," The Journal of Experimental Medicine 173(6):1483-1491 (1991).

Capelo, A. V., et al., "Visceral adiposity is associated with cytokines and decrease in lung function in women with persistent asthma," Rev Port Pneumol., 22(5):255-261 (2016).

Carter, P., "Bispecific Human IgG by Design," The Journal of Immunological Methods, 248(1-2):7-15 (2001).

Ceyhan, G. O., et al., "Neural Invasion in Pancreatic Cancer: A Mutual Tropism Between Neurons and Cancer Cells", Biochemical and Biophysical Research Communications 374:442-447 (2008).

Chang, B.S. and Shenson, S., "Practical Approaches to Protein Formulation Development," Pharmaceutical Biotechnology 13:1-25 (2002).

Chaparro-Riggers, J., et al., "Increasing Serum Half-life and Extending Cholesterol Lowering in Vivo by Engineering Antibody With pH-sensitive Binding in PCSK9," The Journal of biological chemistry 287(14):11090-11097 (2012).

Chappel, M.S., et al., "Identification of a Secondary Fc Gamma RI Binding Site Within a Genetically Engineered Human IgG Antibody," The Journal of Biological Chemistry 268(33):25124-25131 (1993).

Chappel, M.S., et al., "Identification of the Fc Gamma Receptor Class I Binding Site in Human IgG Through the Use of Recombinant IgG1/IgG2 Hybrid and Point-Mutated Antibodies," Proceedings of the National Academy of Sciences of the United States of America 88(20):9036-9040 (1991).

Charge, S.B., and Rudnicki, M.A.."Cellular and Molecular Regulation of Muscle Regeneration," Physiological Reviews, 84(1): 209-238 (2004).

Chau, L.A., et al., "HuM291(Nuvion), a Humanized Fc Receptor-Nonbinding Antibody Against CD3, Anergizes Peripheral Blood T Cells as Partial Agonist of the T Cell Receptor," Transplantation 71(7):941-950 (2001).

Chen, C., et al., "Defective Secretion of an Immunoglobulin Caused by Mutations in the Heavy Chain Complementarity Determining Region 2," The Journal of Experimental Medicine, 180(2):577-586 (1994).

Chen, C., et al., "Generation and Analysis of Random Point Mutations in an Antibody CDR2 Sequence: Many Mutated Antibodies Lose Their Ability to Bind Antigen," The Journal of Experimental Medicine, 176(3):855-866 (1992).

Chen, Y., et al., "Selection and Analysis of an Optimized Anti-VEGF Antibody: Crystal Structure of an Affinity-Matured Fab in Complex With Antigen," Journal of Molecular Biology 293(4):865-881 (1999).

Cheong, Y. C., et al., "Peritoneal healing and adhesion formation/reformation," Hum Reprod Update, 7(6):556-566 (2001).

Chien, N.C., et al., "Significant Structural and Functional Change of an Antigen-binding Site by a Distant Amino Acid Substitution: Proposal of a Structural Mechanism," Proceedings of the National Academy of Sciences of the United States of America, 86(14):5532-5536 (1989).

Chihara, et al., "Autoantibody Producing Cells in Neuromyelitis Optica," Journal of Clinical and Experimental Medicine, 240:534-535 (2012).

Chihara, N., et al., "Interleukin 6 Signaling Promotes Anti-Aquaporin 4 Autoantibody Production from Plasmablasts in Neuromyelitis Optica," Proceedings of the National Academy of Sciences of the United States of America 108(9):3701-3706 (2011).

Chirino, A.J., et al., "Minimizing the Immunogenicity of Protein Therapeutics," Drug Discovery Today, 9(2):82-90 (2004).

(56) References Cited

OTHER PUBLICATIONS

Choi, S.E., et al.,"IL-6 Protects Pancreatic Islet Beta Cells From Pro-inflammatory Cytokines-Induced Cell Death and Functional Impairment in Vitro and in Vivo," Transplant Immunology, 13(1): 43-53 (2004).
Choy, E., "Inhibiting lnterleukin-6 in Rheumatoid Arthritis," Current Rheumatology Reports, 10(5):413-417 (2008).
Christensen, J. R., et al., "Systemic Inflammation in Progressive Multiple Sclerosis Involves Follicular T-Helper, Th17- and Activated B-Cells and Correlates with Progression", PLoS ONE, vol. 8:e57820 (2013).
Chu, G.C., et al., "Accumulation of Succinimide in a Recombinant Monoclonal Antibody in Mildly Acidic Buffers Under Elevated Temperatures," Pharmaceutical Research 24(6):1145-1156 (2007).
Chu, D. K., et al., "Therapeutic potential of anti-IL-6 therapies for granlocytic airway inflammation in asthma," Allergy, Asthma Clin Immunol., 11:14 (2015).
Chugai Pharmaceutical, A Phase I, Multiple-dose Study of SA237, Study JapicCTI—No. 121786; submitted to Clinicaltrials.jp on Jan. 31, 2014; downloaded from clinicaltrials.jp archive on Sep. 5, 2019 as https:/ /www .clinicaltrials.jp/cti -user/trial/Show .jsp, 5 pages.
Chugai Pharmaceutical, A phase I, multiple-dose study of SA237, Study JapicCTI—No. 121786; submitted to Clinicaltrials.jp on Jun. 19, 2012; downloaded from clinicaltrials.jp archive on Sep. 5, 2019 as https://www.clinicaltrials.jp/ctiuser/ trial/Show.jsp, 5 pages.
Chugai Pharmaceutical, A phase I, Multiple-Dose Study of SA237, Study JapicCTI—No. 121786; Submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.
Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)," Study NCT02028884, Version 1, ClinicalTrials.gov, Jan. 6, 2014, accessed at https://clinicaltrials.gov/ct2/history/NCT02028884?V1= View#StudyPageTop, accessed on Sep. 4, 2019, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V 2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V 3=View#StudyPageTop, 6 pages.
Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)" Study NCT02028884, version 4, Submitted to ClinicalTrials.gov on Dec. 8, 2015; Downloaded from ClinicalTrials.gov archive on Sep. 4, 2019 as https://clinicaltrials.gov/ct2/history/NCT02028884?V 4=View#StudyPageTop, 6 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 1, ClinicalTrials.gov, Feb. 25, 2014, accessed at https://clinicaltrials.gov/ct2/history/ NCT02073279?V1=View#StudyPageTop, accessed on Sep. 4, 2019, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V IO=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V 11=View#StudyPageTop, 10 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279? V12=View#StudyPageTop, 10 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 13, ClinicalTrials.gov, Oct. 5, 2015, acccessed at https://clinicaltrials.gov/ct2/history/ NCT02073279?V13=View#StudyPageTop, accessed on Sep. 5, 2019, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V 14=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT02073279?V 2= View#StudyPageTop, 6 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 3; submitted to ClinicalTrials.gov on Dec. 15, 2014; downloaded from ClinicalTrials.gov archive on Sep. 5, 2019 as https:/ /clinicaltrials.gov /ct2/history/ NCT02073279?V3= View#StudyPageTop, 7 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, Version 4; Submitted to ClinicalTrials.gov on Feb. 5, 2015; downloaded from ClinicalTrials.gov archive on Sep. 5, 2019 as https://clinicaltrials.gov/ct2/history/NCT02073279? V4=View#StudyPageTop, 8 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 5, ClinicalTrials.gov, Feb. 6, 2015, accessed at https://clinicaltrials.gov/ct2/history/ NCT02073279?V5=View#StudyPageTop, accessed on Sep. 5, 2019, 8 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V 6=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V 7=View#StudyPageTop, 9 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder

(56) References Cited

OTHER PUBLICATIONS (NMOSD)", Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V8=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 9, ClinicalTrials.gov, Jun. 5, 2015, accessed at https://clinicaltrials.gov/ct2/history/NCT02073279?V9=View#StudyPageTop, accessed on Sep. 5, 2019, 9 pages.

Chung, Y.C., and Chang, Y.F., "Serum Interleukin-6 Levels Reflect the Disease Status of Colorectal Cancer," Journal of Surgical Oncology, 83(4): 222-226 (2003).

Chuntharapai, A. and Kim, K.J., "Generation of Monoclonal Antibodies to Chemokine Receptors," Methods in Enzymology, 288:15-27 (1997).

ClinicalTrials.gov, "A Phase 2a Study to Evaluate the Effects of Sirukumab in Subjects With Severe Poorly Controlled Asthma," ID: NCT02794519, Sponsored by GlaxoSmithKline, Jun. 9, 2016.

Cocco, M., et al., "In Vitro Generation of Long-Lived Human Plasma Cells", Journal of Immunology, 189(12):5773-5785 (2012).

Cole, M.S., et al., "Human IgG2 Variants of Chimeric Anti-CD3 are Nonmitogenic to T Cells," Journal of Immunology 159(7):3613-3621 (1997).

Coloma, M.J., et al., "Position Effects of Variable Region Carbohydrate on the Affinity and in Vivo Behavior of an Anti-(1-6) Dextran Antibody," Journal of Immunology (Baltimore, Md.: 1950), 162(4):2162-2170 (1999).

Comper, W.D., et al., "Charge Selectivity in Kidney Ultrafiltration," Kidney International, 47(5):1242-1251 (1995).

Cordoba, A.J., et al., "Non-Enzymatic Hinge Region Fragmentation of Antibodies in Solution," Journal of Chromatography B 818(2):115-121 (2005).

Costa, L., et al., "Efficacy of Tocilizumab in a Patient with Refractory Psoriatic Arthritis," Clinical Rheumatology 33(9):1355-1357 (2014).

Couto, J.R., et al., "Anti-BA46 Monoclonal Antibody Mc3: Humanization Using a Novel Positional Consensus and in Vivo and in Vitro Characterization," Cancer Research, 55(8):1717-1722 (1995).

Cruse, et al., "Antigens and Immunogens," Atlas of Immunology, CRC Press LLC, excerpt from Chapters, pp. 103 and 109 (2004).

Cuatrecasas, P. and Anfinsen, C.B., "Affinity Chromatography," Methods in Enzymology, 22:345-378 (1971).

Culig, Z., et al., "Interleukin-6 Regulates Androgen Receptor Activity and Prostate Cancer Cell Growth", Molecular and Cellular Endocrinology 197:231-238 (2002).

Dall'Acqua, W.F., et al., "Antibody Humanization by Framework Shuffling," Methods 36(1):43-60 (2005).

Dall'Acqua, W.F., et al., "Increasing the Affinity of a Human IgG1 for the Neonatal Fc Receptor: Biological Consequences," Journal of Immunology 169(9):5171-5180 (2002).

Dall'Acqua, W.F., et al., "Modulation of the Effector Functions of a Human Igg1 Through Engineering of Its Hinge Region," Journal of Immunology 177(2):1129-1138 (2006).

Dall'Acqua, W.F., et al., "Properties of Human IgG1s Engineered for Enhanced Binding to the Neonatal Fc Receptor (FcRn)," The Journal of Biological Chemistry 281(33):23514-23524 (2006).

Damschroder, M.M., et al., "Framework Shuffling of Antibodies to Reduce Immunogenicity and Manipulate Functional and Biophysical Properties," Molecular Immunology, 44(11):3049-3060 (2007).

Dangott, B., et al., "Dietary Creatine Monohydrate Supplementation Increases Satellite Cell Mitotic Activity During Compensatory Hypertrophy," International Journal of Sports Medicine 21(1):13-16 (2000).

Darr, K.C., and Schultz, E.,"Hindlimb Suspension Suppresses Muscle Growth and Satellite Cell Proliferation," Journal of Applied Physiology, 67(5):1827-1834 (1989).

Datta-Mannan, A., et al., "Monoclonal Antibody Clearance. Impact of Modulating the Interaction of IgG With the Neonatal Fc Receptor," The Journal of Biological Chemistry 282(3):1709-1717 (2007).

Davies, G., et al., "The Hgf/sf Antagonist Nk4 Reverses Fibroblast-and Hgf-induced Prostate Tumor Growth and Angiogenesis in Vivo," International Journal of Cancer, 106(3):348-354 (2003).

Davies, J., et al., "Affinity Improvement of Single Antibody VH Domains: Residues in All Three Hypervariable Regions Affect Antigen Binding", Immunotechnology 2:169-179 (1996).

De Groot, A.S., et al., "De-Immunization of Therapeutic Proteins by T-cell Epitope Modification," Developments in Biologicals, 122:171-194 (2005).

De Pascalis, R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology 169(6):3076-3084 (2002).

De Vita, F., et al.,"Serum Levels of Interleukin-6 as a Prognostic Factor in Advanced Non-small Cell Lung Cancer," Oncology Reports, 5(3): 649-652 (1998).

Decision of the EPO Opposition Division for EP2006381 on Jul. 25, 2018.

Decision of the Opposition Division for EP Application No. EP2275443, Munich, Germany, mailed on Apr. 26, 2018.

Declaration by Madhusudan Natarajan, Ph.D. (submitted by the Opponent during EP opposition procedure for EP2708558 and posted by EPO on Jan. 15, 2019).

Declaration of Dr. Anette Henriksen dated Apr. 17, 2019 which was submitted by the Opponent during EPO opposition for EP2006381.

Declaration of Mr. Taichi Kuramochi, dated May 23, 2019, co-inventor of EP2202245 (submitted by the Patentee during EPO opposition procedure for EP2202245).

Declaration of Nimish Gera, Ph.D., CV and Exhibits, dated Sep. 1, 2016.

Deen, W.M., et al., "Structural Determinants of Glomerular Permeability," American Journal of Physiology. Renal Physiology, 281(4):F579-F596 (2001).

Del Rio, G., et al., "An Engineered Penicillin Acylase With Altered Surface Charge is More Stable in Alkaline PH," Annals of the New York Academy of Sciences, 799:61-64 (1996).

Demir, I.E., et al.,"Nerve-cancer Interactions in the Stromal Biology of Pancreatic Cancer," Frontiers in Physiology, 3(97):1-22 (2012).

Deng, B., et al., "An Agonist Murine Monoclonal Antibody to the Human C-mpl Receptor Stimulates Megakaryocytopoiesis," Blood, 92(6):1981-1988 (1998).

Devanaboyina, S.C., et al., "The Effect of pH Dependence of Antibody-Antigen Interactions on Subcellular Trafficking Dynamics", mAbs, 5:851-859 (2013).

Dhiman, N., et al., "Gene Expression Microarrays: A 21st Century Tool for Directed Vaccine Design," Vaccine, 20(1-2):22-30 (2001).

Diaz, R., et al., "Effects of engineering charged amino acids in the $C_H3$ domains on antibody heavy chain dimerization," Philippine Science Letters, 4(1):48-55 (2011).

Dillon, T.M., et al., "Structural and Functional Characterization of Disulfide Isoforms of the Human IgG2 Subclass," The Journal of Biological Chemistry 283(23):16206-16215 (2008).

Ding, W., et al., "The Change of Plasma Interleukin-6 Level and Cardiac Protective Effect of Monoclonal Antibody to IL-6 During Myocardial Infarction Reperfusion," Chinese Journal of Cardiology, 27(1):29-32, (1998) (with English abstract)).

Doerks, T., et al.."Protein Annotation: Detective Work for Function Prediction," Trends in Genetics, 14(6): 248-250 (1998).

Doganci, A., et al., "The IL-6R α chain controls lung CD4+CD25+ Treg development and function during allergic airway inflammation in vivo," J Clin Invest., 115(2):313-325 (2005).

Drake, A.W. and Papalia, G.A., "Chapter 5: Biophysical Considerations for Development of Antibody-Based Therapeutics," Biophysical Considerations for Development of Antibody-Based Therapeutics, 95-97 (2012).

Duluc, D., et al., "Tumor-associated Leukemia Inhibitory Factor and Il-6 Skew Monocyte Differentiation Into Tumor-associated Macrophage-like Cells", Blood, 110:4319-4330 (2007).

(56) References Cited

OTHER PUBLICATIONS

Durkee, K.H., et al., "Immunoaffinity Chromatographic Purification of Russell's Viper Venom Factor X Activator Using Elution in High Concentrations of Magnesium Chloride," Protein Expression and Purification 4(5):405-411 (1993).
Ebos, J. M. L., et al., "Accelerated Metastasis after Short-Term Treatment with a Potent Inhibitor of Tumor Angiogenesis," Cancer Cell, 15(3):232-239 (2009).
Eder, I.E., et al., "Targeting the Androgen Receptor in Hormone-refractory Prostate Cancer—new Concepts," Future Oncology, 1(1): 93-101 (2005).
Ejima, D., et al., "Effective Elution of Antibodies by Arginine and Arginine Derivatives in Affinity Column Chromatography," Analytical Biochemistry, 345(2):250-257 (2005).
Ejima, D., et al., "Effects of Acid Exposure on the Conformation, Stability, and Aggregation of Monoclonal Antibodies," Proteins 66(4):954-962 (2007).
Elliott, S., et al., "Activation of the Erythropoietin (EPO) Receptor by Bivalent Anti-EPO Receptor Antibodies", The Journal of Biological Chemistry 271 (40):24691-24697 (1996).
European Patent Office Register Extract for European Patent No. EP1915397, submitted by opponents in opposition for EP2006381, filed Nov. 1, 2016.
Esty, B., et al., 346: Anti-IL-6 treatment in two pediatric patients with severe persistent asthma with the IL4R$^{576}$ variant, Presentation, AAAAI/WAO Joint Congress, Mar. 2-5, 2018, Orlando, FL, USA, https://aaaai.confex.com/aaaai/wao18/webprogram/Paper34378.html.
EU Clinical Trials Register for SA-307JG, European Medicines Agency, Sponsor: Hoffmann-La Roche Ltd., May 19, 2014.
EU Clinical Trials Register for SA-309JG, European Medicines Agency, Sponsor: F. Hoffmann-La Roche Ltd., Registry No. NCT02073279, Dec. 15, 2016.
European Search Report dated Mar. 16, 2009, for EP Application No. 07740474, Igawa et al., filed Mar. 30, 2007, 5 pages.
European Search Report dated Nov. 25, 2009 for EP Application No. 06832657, Okada et al., filed Nov. 15, 2006, 4 pages.
European Search Report for EP Application No. 06833196, dated Aug. 27, 2009, 5 pages.
European Search Report for EP Application No. 06812073, The Hague, Netherlands, dated Nov. 20, 2009, 5 pages.
European Search Report for EP Application No. 09729337, Munich, Germany, dated Nov. 3, 2011, 3 pages.
European Search Report for EP Patent Application No. 07740494, Munich, Germany dated Sep. 3, 2009, 3 pages.
Ewert, S., et al., "Stability Improvement of Antibodies for Extracellular and Intracellular Applications: CDR Grafting to Stable Frameworks and Structure-based Framework Engineering," Methods, 34(2):184-199 (2004).
Extended European Search Report dated Sep. 8, 2009 for EP Patent Application No. 06833196.6, Nakashima et al., filed Nov. 24, 2006, 9 pages.
Extended European Search Report for EP Application No. 06832657.8, The Hague, Netherlands, dated Dec. 3, 2009, 7 pages.
Extended European Search Report for EP Application No. 08703686.9, The Hague, Netherlands, dated Aug. 24, 2010, 13 pages.
Extended European Search Report for EP Application No. 07741181.7, The Hague, Netherlands, dated Dec. 23, 2009, 6 pages.
Extended European Search Report for EP Patent Application No. 06811729.0, The Hague, Netherlands dated Dec. 23, 2009, 7 pages.
Extended European Search Report for EP Patent Application No. 07707458.1, The Hague, Netherlands dated Dec. 11, 2009, 6 pages.
Extended European Search Report for EP Patent Application No. 06812073.2, The Hague, Netherlands, dated Dec. 7, 2009, 8 pages.
F. Hoffmann-La Roche Ltd., "A Multicenter, Randomized, Addition to Baseline Treatment, Double-blind, Placebo-controlled, Phase 3 Study to Evaluate the Efficacy and Safety of Satralizumab (SA237) in Patients With Neuromyelitis Optica (NMO) and NMO Spectrum Disorder (NMOSD)," Study EudraCT 2013-003752-21, Germany, clinicaltrialsregister.eu, Dec. 20, 2013; downloaded from clinicaltrialsregister.eu, accessed at https://www.clinicaltrialsregister.eu/ctr-search/trial/2013-003752-21/DE, accessed on Sep. 23, 2021, 7 pages.
F. Hoffmann-La Roche Ltd., "A Multicenter, Randomized, Addition to Baseline Treatment, Double-Blind, Placebo-controlled, Phase 3 Study to Evaluate the Efficacy and Safety of Satralizumab (SA237) in Patients With Neuromyelitis Optica (NMO) and NMO Spectrum Disorder (NMOSD)," Study EudraCT 2013-003752-21, Hungary, clinicaltrialsregister.eu, Feb. 25, 2015, accessed at https://www.clinicaltrialsregister.eu/ctr-search/trial/2013-003752-2J/HU, accessed on Sep. 23, 2021, 6 pages.
F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-searchltrial/2013-003752-21/DE, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 ashttps://www.clinicaltrialsregister.eu/ctr-search/trial/2013-003752-21/HU, 6 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctr-search/trial/2013-003752-21/IT, 5 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Jul. 4, 2014; downloaded from clinicaltrialsregister.eu archive on Sep. 23, 2019 ashttps://www.clinicaltrialsregister.eu/ctr-search/trial/2013-003752-21/GB, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/PL, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrinlsnoisteceu/ctr-search/tdal/20l:-003752-21/ES, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 ashttps://www.clinicaltrialsregister.eu/ctr-search/trial/2013-003752-21/GB, 6 pages.
F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum

(56) References Cited

OTHER PUBLICATIONS disorder (NMOSD)," Study EudraCT 2013-003752-21 in the United Kingdom; submitted to clinicaltrialsregister.eu on Oct. 15, 2013; downloaded from clinicaltrialsregister.eu archive on Sep. 23, 2021 https://www.clinicaltrialsregister.eu/ctr-search/trial/2013-003752-21/GB, 6 pages.
F. Hoffmann-La Roche Ltd., "A Multicenter, Randomized, Addition to Baseline Treatment, Double-blind, Placebo-controlled, Phase 3 Study to Evaluate the Efficacy and Safety of Satralizumab (SA237) in Patients With Neuromyelitis Optica (NMO) and NMO Spectrum Disorder (NMOSD)," Study EudraCT 2013-003752-21, Italy, clinicaltrialsregister.eu, Feb. 6, 2014, accessed at https://www.clinicaltrialsregister.eu/ctr-search/trial/2013-003752-21/IT, accessed on Sep. 23, 2021, 5 pages.
F. Hoffmann-La Roche Ltd., "A Multicenter, Randomized, Addition to Baseline Treatment, Double-blind, Placebo-controlled, Phase 3 Study to Evaluate the Efficacy and Safety of Satralizumab (SA237) in Patients With Neuromyelitis Optica (NMO) and NMO Spectrum Disorder (NMOSD)," Study EudraCT 2013-003752-21, Spain, clinicaltrialsregister.eu, Mar. 11, 2015; downloaded from clinicaltrialsregister.eu, accessed at https://www.clinicaltrialsregister.eu/ctr-search/trial/2013-003752-21/ES, accessed on Sep. 23, 2021, 7 pages.
F. Hoffmann-La Roche Ltd., "A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-searchltrial/2015-005431-41/HR, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Croatia; submitted to clinicaltrialsregister.eu on Dec. 15, 2016; downloaded from clinicaltrialsregister.eu archive on May 19, 2021.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctr-search/trial/2015-005431-41/PL, 6 pages.
F. Hoffmann-La Roche Ltd., "Efficacy and Safety Study of Satralizumab (SA237) as Add-on Therapy to Treat Participants With Neuromyelitis Optica (NMO) and NMO Spectrum Disorder (NMOSD)," Study NCT02028884, first posted on clinicaltrialsregister.eu on Jan. 7, 2014 and last updated on Apr. 13, 2021; downloaded from clinicaltrialsregister.eu archive on May 19, 2021, https://clinicaltrials.gov/ct2/show/NCT02028884.
F. Hoffmann-La Roche Ltd., "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, first posted on clinicaltrialsregister.eu on Feb. 27, 2014 and last updated on Mar. 24, 2021; downloaded from clinicaltrialsregister.eu archive on May 19, 2021.
Feaver, R., et al., "The Anti-IL-6 Antibody Sirukumab Inhibits Vascular Inflammation in a Human Surrogate Model of Atherosclerosis," American College of Rheumatology Meeting Abstracts, Abstract 439:S187 (2014).
Feinberg, H., et al., "Mechanism of pH-dependent N-Acetylgalactosamine Binding by a Functional Mimic of the Hepatocyte Asialoglycoprotein Receptor," The Journal of Biological Chemistry, 275(45):35176-35184 (2000).
Ferl, G.Z., et al., "A Predictive Model of Therapeutic Monoclonal Antibody Dynamics and Regulation by the Neonatal Fc Receptor (FcRn)," Annals of Biomedical Engineering 33(11):1640-1652 (2005).
Fiedler, M., et al., "An Engineered in-1 F(Ab) Fragment With Improved Affinity for the Nogo-a Axonal Growth Inhibitor Permits Immunochemical Detection and Shows Enhanced Neutralizing Activity," Protein Engineering, 15(11): 931-941 (2002).
Final Office Action dated Aug. 1, 2013 in U.S. Appl. No. 13/595,139, Igawa et al., filed Aug. 27, 2012.
Final Office Action dated Oct. 15, 2012 in U.S. Appl. No. 12/524,041, Takahashi et al., filed Sep. 18, 2009.
Final Office Action dated Jul. 19, 2018 in U.S. Appl. No. 15/495,026, Igawa et al., filed Apr. 24, 2017.
Final Office Action dated Apr. 9, 2012 in U.S. Appl. No. 12/161,733, Ishida et al., filed Mar. 9, 2009.
Final Office Action dated Apr. 12, 2012 in U.S. Appl. No. 12/295,039, Igawa et al., filed Jan. 20, 2009.
Office Action dated Feb. 5, 2019 in U.S. Appl. No. 15/495,026, Igawa et al., filed Apr. 24, 2017.
Final Office Action dated Jul. 26, 2011 in U.S. Appl. No. 12/296,193, Nishimoto et al., filed Apr. 15, 2009.
Final Office Action dated Jun. 8, 2011, in U.S. Appl. No. 12/090,676, Kobara et al., filed Feb. 25, 2009.
Final Office Action dated Mar. 2, 2018 in U.S. Appl. No. 13/637,415, Igawa et al., filed Feb. 4, 2013.
Final Office Action dated Mar. 20, 2013 in U.S. Appl. No. 12/996,162, Mitsunaga et al., filed Mar. 7, 2011.
Final Office Action dated Nov. 13, 2015 in U.S. Appl. No. 13/637,415, Igawa et al., filed Feb. 4, 2013.
Final Office Action dated Sep. 9, 2019 in U.S. Appl. No. 15/495,026, Igawa et al., filed Apr. 24, 2017.
Final Office Action dated Feb. 19, 2016, U.S. Appl. No. 13/387,292, Maeda, filed Apr. 3, 2012.
Final Office Action dated Jul. 24, 2017, U.S. Appl. No. 13/387,292, Maeda, filed Apr. 3, 2012.
Final Office Action dated Nov. 15, 2013, U.S. Appl. No. 13/387,292, Maeda, filed Apr. 3, 2012.
Final Office Action dated Nov. 25, 2014, U.S. Appl. No. 13/387,292, Maeda, filed Apr. 3, 2012.
Finkel, M.S., et al., "Negative Inotropic Effects of Cytokines on the Heart Mediated by Nitric Oxide," Science, 257(5068):387-389 (1992).
Finkelman, F.D., et al., "Anti-cytokine Antibodies as Carrier Proteins. Prolongation of in Vivo Effects of Exogenous Cytokines by Injection of Cytokine-Anti-cytokine Antibody Complexes," Journal of Immunology 151:1235-1244 (1993).
Fisher, P.A. and Smith, D.E., "Affinity Purification of Antibodies Using Antigens Immobilized on Solid Supports," Biochemical Society Transactions, 16(2):134-138 (1988).
Fisniku, O., et al., "Protective Effects of PG490-88 on Chronic Allograft Rejection by Changing Intragraft Gene Expression Profiles," Transplantation Proceedings 37:1962-1964 (2005).
Foote, J. and Winter, G., "Antibody Framework Residues Affecting the Conformation of the Hypervariable Loops," Journal of Molecular Biology 224(2):487-499 (1992).
Ford, H. R., et al., "Evidence that Production of Interleukin 6 within the Rejecting Allograft Coincides with Cytotoxic T Lymphocyte Development," Transplantation, 51 (3):656-661 (1991).
Preliminary Amendment and Response to Restriction Requirement filed Jun. 29, 2012 in U.S. Appl. No. 12/680,082, Igawa et al., filed Jun. 25, 2010.
Fraunberger, P., et al., "Cytokine and Cytokine-receptor Profiles After Liver and Heart Transplantation," Transplantation Proceedings, 27(3):2023-2027 (1995).
Fredj, S., et al., "Role of Interleukin-6 in Cardiomyocyte/Cardiac Fibroblast Interactions During Myocyte Hypertrophy and Fibroblast Proliferation", Journal of Cellular Physiology 204:428-436 (2005).
Fuchs, M., et al., "Role of Interleukin-6 for LV Remodeling and Survival After Experimental Myocardial Infarction," FASEB Journal 17(14):2118-2120 (2003).
Fujii, I., "Antibody Affinity Maturation by Random Mutagenesis," Methods in Molecular Biology, 248:345-359 (2004).

(56) References Cited

OTHER PUBLICATIONS

Fujita, J., et al.,"Anti-interleukin-6 Receptor Antibody Prevents Muscle Atrophy in Colon-26 Adenocarcinoma-bearing Mice With Modulation of Lysosomal and Atp-ubiquitin-dependent Proteolytic Pathways," International Journal of Cancer, 68(5): 637-643 (1996).
Fujiwara, et al., "Control of Tumor Immunity by B Cells and Th2 Cytokines," Annual Reviews, 1999:257-269 (1999) (with an unverified English translation).
Furukawa, Y., et al., "Cytokine Gene Expression During the Development of Graft Coronary Artery Disease in Mice", Japanese Circulation Journal 63:775-782 (1999).
Furuya, Y., et al., "Interleukin-6 as a Potential Therapeutic Target for Pulmonary Arterial Hypertension," International Journal of Rheumatology, 2010:720305 (2010).
Gao, S. P., et al.."Mutations in the EGFR Kinase Domain Mediate STAT3 Activation via IL-6 Production in Human Lung Adenocarcinomas," The Journal of Clinical Investigation, 117(12):3846-3856 (2007).
Garry, D.J., et al., "Myogenic Stem Cell Function is Impaired in Mice Lacking the Forkhead/winged Helix Protein MNF," Proceedings of the National Academy of Sciences of the United States of America, 97(10):5416-5421 (2000).
Garry, D,J., et al., "Persistent Expression of MNF Identifies Myogenic Stem Cells in Postnatal Muscles," Developmental Biology 188:280-294 (1997).
GE Healthcare, "Biacore, Sensor Surface Handbook," BR-1005-71, Edition AB, Feb. 2005, pp. 1-100.
GenBank Accession No. AAG00910.2, Recombinant IgG2 Heavy Chain, Partial [*Homo sapiens*], May 14, 2001.
Geneseq Accession No. AEM45140, Light Chain Constant Region of Therapeutic Human IgG Antibody, Feb. 22, 2007.
Geneseq Accession No. ARZ17615, Human Antibody IgG2 Heavy Chain Constant Region, SEQ ID No. 36, Aug. 21, 2008.
Gera, N., et al., "Design of pH Sensitive Binding Proteins From the Hyperthermophilic Sso7d Scaffold," PLoS One, 7(11):e48928 (2012).
Gerstner, R.B., et al., "Sequence Plasticity in the Antigen-binding Site of a Therapeutic Anti-HER2 Antibody," Journal of Molecular Biology, 321(5):851-862 (2002).
Gessner, J.E., et al., "The IgG Fc Receptor Family," Annals of Hematology 76(6):231-248 (1998).
Ghetie, V. and Ward, E.S., "Fern: the Mhc Class I-related Receptor That is More Than an IgG Transporter," Immunology Today 18(12):592-598 (1997).
Ghetie, V., et al., "Increasing the Serum Persistence of an IgG Fragment by Random Mutagenesis," Nature Biotechnology 15(7):637-640 (1997).
Ghetie, V., et al., "Multiple Roles for the Major Histocompatibility Complex Class I-Related Receptor FcRn," Annual Review of Immunology, 18:739-766 (2000).
Ghosh, S. and Karin, M., "Missing Pieces in the NF-KB Puzzle," Cell 109:S81-S96 (2002).
Giugliano, G., et al., "Verapamil Inhibits lnterleukin-6 and Vascular Endothelial Growth Factor Production in Primary Cultures of Keloid Fibroblasts," British Journal of Plastic Surgery 56(8):804-809 (2003).
Glick, B.R et al., ed., "Principles and Applications of Recombinant DNA, 3rd Edition," Molecular Biotechnology, 168 (2005).
Gobburu, J.V., et al., "Pharmacokinetics/dynamics of 5c8, a Monoclonal Antibody to CD154 (CD40 Ligand) Suppression of an Immune Response in Monkeys," The Journal of Pharmacology and Experimental Therapeutics, 286(2):925-930 (1998).
Goode, N.P., et al., "The Glomerular Basement Membrane Charge-selectivity Barrier: an Oversimplified Concept," Nephrology Dialysis Transplantation, 11(9):1714-1716 (1996).
Gopferich, A., et al., "Drug Delivery from Bioerodible Polymers," Chapter 15 in Formulation and Delivery of Proteins and Peptides, 567:242-277, eds. Cleland et al. (1994).
Granted claims of European Patent Application No. EP2275443, submitted on May 24, 2019 by the Patentee during EPO Opposition Procedure for EP2202245, 1 page.
Graves, S.S., et al., "Molecular Modeling and Preclinical Evaluation of the Humanized NR-LU-13 Antibody," Clinical Cancer Research, 5(4):899-908 (1999).
Greenberg, A.S., et al.."Interleukin 6 Reduces Lipoprotein Lipase Activity in Adipose Tissue of Mice in Vivo and in 3t3-l1 Adipocytes: a Possible Role for Interleukin 6 in Cancer Cachexia," Cancer Research, 52(15): 4113-4116 (1992).
Greten, F.R., et al., "IKKbeta Links Inflammation and Tumorigenesis in a Mouse Model of Colitis-associated Cancer," Cell, 118(3):285-296 (2004).
Grossniklaus, H.E. and Green, W.R., "Choroidal Neovascularization," American Journal of Ophthalmology 137:496-503 (2004).
Guerne, P.A., et al., "Synovium as a Source of Interleukin 6 in Vitro. Contribution to Local and Systemic Manifestations of Arthritis," The Journal of Clinical Investigation 83(2):585-592 (1989).
Guice, K.S., et al., "Anti-tumor Necrosis Factor Antibody Augments Edema Formation in Caerulein-induced Acute Pancreatitis," The Journal of Surgical Research, 51(6): 495-499 (1991).
Guillen, I., et al., "Cytokine Signaling During Myocardial Infarction: Sequential Appearance of IL-1 Beta and IL-6," The American Journal of Physiology, 269(2 Pt 2):R229-R235 (1995).
Gupta, S. and Suresh, M., "Affinity Chromatography and Co-chromatography of Bispecific Monoclonal Antibody Immunoconjugates," Journal of Biochemical and Biophysical Methods, 51(3):203-216 (2002).
Guyre, P.M., et al., "Increased Potency of Fc-Receptor-Targeted Antigens," Cancer Immunology 45(3-4):146-148 (1997).
Gwechenberger, M., et al., "Cardiac Myocytes Product Interleukin-6 in Culture and in Viable Border Zone ofReperfused Infarctions", Circulation, 99:546-551 (1999).
Habara, T., et al., "The biological effects of antiadhesion agents on activated RAW264.7 macrophages," J Biomed Mater Res., 61(4):628-633 (2002).
Hamers-Casterman, C., et al., "Naturally Occurring Antibodies Devoid of Light Chains," Nature, 363(6428):446-448 (1993).
Hanahan, D and Weinberg, R.A., "Hallmarks of Cancer: the Next Generation," Cell 144(5):646-674, Cell Press, United States (Mar. 2011).
Hanes, J., et al., "Picomolar Affinity Antibodies From a Fully Synthetic Naive Library Selected and Evolved by Ribosome Display," Nature Biotechnology 18(12):1287-1292 (2000).
Hanson, C.V., et al., "Catalytic Antibodies and Their Applications," Biotechnology Letters, 16:631-636 (2005).
Hashizume, M., et al., "Tocilizumab, a Humanized Anti-interleukin-6 Receptor Antibody, Improved Anemia in Monkey Arthritis by Suppressing IL-6-induced Hepcidin Production," Rheumatology International, 30(7):917-923 (2010).
Hashizume, M. and Ohsugi, Y., "Various actions of IL-6: Significance of IL-6 in autoimmune and inflammatory diseases," Folia Pharmacol Jpn., 144:172-177 (2014).
Hatzi, E., et al., "N-myc Oncogene Overexpression Down-Regulates IL-6; Evidence that IL-6 Inhibits Angiogenesis and Suppresses Neuroblastoma Tumor Growth", Oncogene 21:3552-3561 (2002).
He, X.Y., et al., "Humanization and Pharmacokinetics of a Monoclonal Antibody With Specificity for Both E- and P-selectin," Journal of Immunology (Baltimore, Md. : 1950), 160(2):1029-1035 (1998).
Hinton, P.R., et al., "An Engineered Human IgG1 Antibody With Longer Serum Half-life," Journal of Immunology, 176(1):346-356 (2006).
Hinton, P.R., et al., "Engineered Human IgG Antibodies With Longer Serum Half-lives in Primates," The Journal of Biological Chemistry 279(8):6213-6216 (2004).
Hirai, I., et al., "Perineural Invasion in Pancreatic Cancer," Pancreas, 24(1):15-25 (2002).
Hirano et al., "Complementary DNA for a novel human interleukin (BSF-2) that induces Blymphocytes to produce immunoglobulin," Nature, 324: 73-76 (1986).
Hirano, T., et al., "Excessive Production of Interleukin 6/b Cell Stimulatory Factor-2 in Rheumatoid Arthritis," European Journal of Immunology, 18(11):1797-1801 (1988).

(56) References Cited

OTHER PUBLICATIONS

Hirata, Y., et al., "Characterization of IL-6 Receptor Expression by Monoclonal and Polyclonal Antibodies", Journal of Immunology 143:2900-2906 (1989).
Hirata, Y., et al., "Loss of a gp 130 Cardiac Muscle Cell Survival Pathway is a Critical Event in the Onset of Heart Failure During Biomechanical Stress," Cell, 97:189-198 (1999).
Hird, V., et al., "Tumour Localisation With a Radioactively Labelled Reshaped Human Monoclonal Antibody," British Journal of Cancer, 64(5):911-914 (1991).
Hironiwa, N., et al., "Calcium-dependent Antigen Binding as a Novel Modality for Antibody Recycling by Endosomal Antigen Dissociation," MAbs, 8(1):65-73 (2016).
Hirota, H., et al., "Continuous Activation of gp130, a Signal-transducing Receptor Component for Interleukin 6-related Cytokines, Causes Myocardial Hypertrophy in Mice," Proceedings of the National Academy of Sciences of the United States of America, 92(11):4862-4826 (1995).
Hocking, D.C., et al., "Mechanisms of Pulmonary Edema Induced by Tumor Necrosis Factor-α," Circulation Research, 67:68-77, (1990).
Hoffmann, S., et al., "Inhibitory Effects of Verapamil Isomers on the Proliferation of Choroidal Endothelial Cells," Graefe's archive for clinical and experimental ophthalmology, 244(3):376-381 (2006).
Holt, L. J., et al., "Domain Antibodies: Proteins for Therapy", Trends in Biotechnology 21:484-490 (2003).
Holmdahl, L., "The Role of Fibrinolysis in Adhesion Formation," Eur J Surg., Suppl 577:24-31 (1997).
Honda, S., et al., "Marginal Zone B Cells Exacerbate Endotoxic Shock via Interleukin-6 Secretion Induced by Fcα/μR-coupled TLR4 Signalling," Nature Communications 7:11498 (2016).
Hong, D. S., et al.,"Interleukin-6 and Its Receptor in Cancer," Cancer 110:1911-1928 (2007).
Hong, G., et al., "Enhanced Cellular Uptake and Transport of Polyclonal Immunoglobulin G and Fab After Their Cationization," Journal of Drug Targeting, 8(2):67-77 (2000).
Hoogenboom, H.R., "Selecting and Screening Recombinant Antibody Libraries," Nature Biotechnology 23(9):1105-1116 (2005).
Horinaga, M., et al., "Clinical and Pathologic Significance of Activation of Signal Transducer and Activator of Transcription 3 in Prostate Cancer," Urology, 66:671-675 (2005).
Hornick, P. and Rose, M., "Chronic Rejection in the Heart," Methods in Molecular Biology, 333:131-144 (2006).
Hosokawa, T., et al., "The Response to Treatment with Interferon Beta-Ib in Patients with Multiple Sclerosis," Shinkei Chiryo, 25:589-595 (2008).
Hotzel, I., et al., "A Strategy for Risk Mitigation of Antibodies With Fast Clearance," mAbs, 4(6):753-760 (2012).
Houssiau, F.A., et al., "Interleukin-6 in Synovial Fluid and Serum of Patients With Rheumatoid Arthritis and Other Inflammatory Arthritides," Arthritis and Rheumatism 31(6):784-788 (1988).
Houzen, H., et al., "Increased Prevalence, Incidence, and Female Predominance of Multiple Sclerosis in Northern Japan," Journal of the Neurological Sciences, 323(1-2):117-22 (2012).
Huang, C., et al., "Inhibition of STAT3 Activity with AG490 Decreases the Invasion of Human Pancreatic Cancer Cells in Vitro", Cancer Science 97:1417-1423 (2006).
Huang, C., et al., "Inhibitory Effect of AG490 on Invasion and Metastasis of Human Pancreatic Cancer Cells in Vitro," Chinese Journal of Oncology 28(12):890-892 (2006).
Huang, Y.W. and Vitetta, E.S., "A Monoclonal Anti-Human IL-6 Receptor Antibody Inhibits the Proliferation of Human Myeloma Cells," Hybridoma, 12(5):621-630 (1993).
Hudes, G.R., et al., "Preliminary Results of a Phase I Study: A Chimeric Monoclonal Anti IL-6 Antibody CNTO 328 in Combination with Docetaxel in Patients with Hormone Refractory Prostate Cancer," Journal of Clinical Oncology, 25:18S (2007).
Hughes-Jones, N.C., et al., "The Effect of pH and Ionic Strength on the Reaction between Anti-D and Erythrocytes," Immunology, 7:72-81 (1964).
Huizinga, T.W., et al., "Sarilumab, A Fully Human Monoclonal Antibody Against IL-6Rα in Patients with Rheumatoid Arthritis and an Inadequate Response to Methotrexate: Efficacy and Safety Results from the Randomised SARIL-RA-MOBILITY Part A Trial", Annals of the Rheumatic Diseases 73:1626-1634 (2014).
Huse, K., et al., "Purification of Antibodies by Affinity Chromatography," Journal of Biochemical and Biophysical Methods, 51(3):217-231 (2002).
Hwang, W.Y., et al., "Use of Human Germline Genes in a CDR Homology-based Approach to Antibody Humanization," Methods (San Diego, Calif.), 36(1):35-42 (2005).
Idezawa, T., et al., "Interleukin-6 Functions as an Autocrine Invasion Factor of Human Pancreatic Cancer Cells," Yamanashi Medical Journal, 19(2):53-67 (2004).
Idezawa, T., et al., "Interleukin-6 Functions as an Autocrine Invasion Factor of Human Pancreatic Cancer Cells," Yamanashi Medical Journal, 20(2):xxxvi (2005).
Igawa, et al., "Antibody Optimization Technologies for Developing Next Generation Antibody Therapeutics", Bio Industry 28:15-21 (2011).
Igawa, T., et al., "Engineering the Variable Region of Therapeutic IgG Antibodies," MAbs, 3(3):243-252 (2011).
Igawa, T., et al., "Reduced Elimination of IgG Antibodies by Engineering the Variable Region," Protein engineering, design & selection, 23(5):385-92 (2010).
Igawa, T., et al., "Antibody Recycling by Engineered pH-Dependent Antigen Binding Improves the Duration of Antigen Neutralization," Nature Biotechnology, 28(11):1203-1207 (2010).
Igawa, T., et al., "Engineered Monoclonal Antibody With Novel Antigen-sweeping Activity in Vivo," PLoS One, 8(5):e63236 (2013).
Igawa, T., et al., "Reduced Elimination of IgG Antibodies by Engineering the Variable Region," Protein Engineering, Design & Selection, 23(5):385-392 (2010).
Igawa, T., et al., "pH-dependent antigen-binding antibodies as a novel therapeutic modality," Biochim Biophys Acta., 1844(11):1943-1950 (2014).
Iijima, T., et al., "Tocilizumab Improves Systemic Rheumatoid Vasculitis With Necrotizing Crescentic Glomerulonephritis," Modern Rheumatology, 25:138-142 (2015).
International Preliminary Report on Patentability dated May 20, 2008 for International Application No. PCT/JP2006/322726, Okada et al., filed Nov. 15, 2006, 9 pages.
International Preliminary Report on Patentability dated Nov. 30, 2010 for International Application No. PCT/JP2009/057309, Igawa et al., filed Apr. 10, 2009, 6 pages.
International Preliminary Report on Patentability dated Nov. 21, 2017 for International Application No. PCT/JP2016/064818, Yamamura et al., filed May 19, 2016, 5 pages.
International Preliminary Report on Patentability dated Apr. 7, 2010 for International Application No. PCT/JP2008/067499, Igawa et al., filed Sep. 26, 2008, 5 pages.
International Preliminary Report on Patentability dated Feb. 7, 2012 for International Application No. PCT/JP2010/062874, Maeda, filed Jul. 30, 2010, 9 pages.
International Preliminary Report on Patentability dated Jul. 29, 2008 for International Application No. PCT/JP2007/051226, Ishida, filed Jan. 26, 2007, 6 pages.
International Preliminary Report on Patentability dated Oct. 21, 2008 for International Application No. PCT/JP2007/057036, Igawa et al., filed Mar. 30, 2007, 6 pages.
International Preliminary Report on Patentability dated Nov. 17, 2008 for International Application No. PCT/JP2007/057745, Nishimoto et al., filed Apr. 6, 2007, 6 pages.
International Preliminary Report on Patentability dated Jun. 4, 2013 for International Application No. PCT/JP2011/077619, Igawa et al., filed Nov. 30, 2011, 7 pages.
International Preliminary Report on Patentability dated Apr. 22, 2008 for International Application No. PCT/JP2006/320905, Kobara, filed Oct. 20, 2006, 8 pages.
International Preliminary Report on Patentability dated Apr. 7, 2010 for International Application No. PCT/JP2008/067534, Igawa et al., filed Sep. 26, 2008, 7 pages.

(56) References Cited

OTHER PUBLICATIONS

International Preliminary Report on Patentability dated May 10, 2011 for International Application No. PCT/JP2009/066590, Igawa et al., filed Sep. 25, 2009, 5 pages.
International Preliminary Report on Patentability dated Apr. 16, 2008 for International Application No. PCT/JP2006/320441, Yasunami, filed Oct. 13, 2006, 5 pages.
International Preliminary Report on Patentability dated May 27, 2008 for International Application No. PCT/JP2006/323392, Nakashima et al., filed Nov. 24, 2006, 10 pages.
International Preliminary Report on Patentability dated Oct. 21, 2008 for International Application No. PCT/JP2007/057058, Igawa et al., filed Mar. 30, 2007, 11 pages.
International Preliminary Report on Patentability dated Jan. 11, 2011 for International Application No. PCT/JP2009/060314, Mitsunaga et al., filed Jun. 5, 2009, 8 pages.
International Preliminary Report on Patentability dated Aug. 29, 2017 for International Application No. PCT/JP2016/055768, Kakehi et al., filed Feb. 26, 2016, 8 pages.
International Preliminary Report on Patentability with Written Opinion for Application No. PCT/JP2008/050842, Japanese Patent Office, Tokyo dated Jul. 28, 2009, 6 pages.
International Search Report dated May 1, 2007 for Application No. PCT/JP2007/057036, Igawa, T., et al., filed Mar. 30, 2007, 2 pages.
International Search Report dated Aug. 11, 2009 for Application No. PCT/JP2009/060314, Mitsunaga, S., et al., filed Jun. 5, 2009, 3 pages.
International Search Report dated Jan. 16, 2007 for International Application No. PCT/JP2006/320905, Kobara, M. et al., filed Sep. 20, 2006, 4 pages.
International Search Report for Application International Application No. PCT/JP2007/051226, Japanese Patent Office, Japan, dated May 1, 2007, 4 pages.
International Search Report for Application No. PCT/JP2006/322726, Japanese Patent Office, Tokyo dated Jan. 9, 2007, 5 pages.
International Search Report for Application No. PCT/JP2010/062874, Japanese Patent office, Tokyo dated Aug. 31, 2010, 3 pages.
International Search Report for EP Patent Application No. PCT/JP2008/050842, Japanese Patent office, Tokyo dated Feb. 19, 2008, 2 pages.
International Search Report for EP Patent Application No. PCT/JP2009/066590, Japanese Patent office, Tokyo dated Oct. 20, 2009, 3 pages.
International Search Report for EP Patent Application No. PCT/JP2016/055768, Japanese Patent office, Tokyo dated May 17, 2016, 3 pages.
International Search Report for International Application No. PCT/JP2006/320441, Japanese Patent Office, dated Dec. 19, 2006, 3 pages.
International Search Report for International Application No. PCT/JP2006/323392, Japanese Patent Office, Japan, dated Jan. 9, 2007, 4 pages.
International Search Report for International Application No. PCT/JP2007/057058, Japanese Patent Office, dated May 7, 2001, 2 pages.
International Search Report for International Application No. PCT/JP2007/057745, Japanese Patent Office, dated Jul. 10, 2007, 3 pages.
International Search Report for International Application No. PCT/JP2008/067534, Japanese Patent Office, Japan, dated Oct. 21, 2008, 2 pages.
International Search Report for International Application No. PCT/JP2009/057309, Japanese Patent Office, dated Jul. 7, 2009, 3 pages.
International Search Report for International Application No. PCT/JP2011/062209, Japanese Patent Office, dated Jul. 12, 2011, 3 pages.
International Search Report for International Application No. PCT/JP2011/077619, Japanese Patent Office, dated Feb. 28, 2012, 4 pages.
International Search Report for International Application No. PCT/JP2014/065449, Japanese Patent Office, Japan, dated Sep. 22, 2014, 2 pages.
International Search Report for International Application No. PCT/JP2016/064818, Japanese Patent Office, dated Aug. 16, 2016, 2 pages.
Ishii, et al., "FcRn, a Critical Regulator of Antibody Pharmacokinetics," Nihon Yakurigaku Zasshi. Folia Pharmacologica Japonica 136(5):280-284, Nippon Yakuri Gakkai, Japan (2010).
Ito, et al., "Regulation of Damage to Islets Transplanted into the Liver by IL-6 Receptor Antibody," Journal of Japan Surgical Society 107 (special extra issue 2):387, PS-014-5 (2006) (English translation included).
Ito, N., et al., "Induction of Interleukin-6 by Interferon Alfa and Its Abrogation by a Serine Protease Inhibitor in Patients with Chronic Hepatitis C," Hepatology, 23(4):669-675, Wiley, United States (1996).
Ito, W., et al., "The His-probe Method: Effects of Histidine Residues Introduced Into the Complementarity-Determining Regions of Antibodies on Antigen-antibody Interactions at Different Ph Values," FEBS letters, 309(1):85-88 (1992).
Itoh, et al., "Anti-IL-6 Receptor Antibody Down-Regulates Pro-Inflammation Cytokine Production of Gr-1 *CD11b* Cells and Prevents Early Loss of Islet Grafts in the Liver of Mice in Association with Engraftments," Transplantation, 82(Supp. 3), World Transplant Congress, Abstract No. 2838 (2006).
Izawa, et al., "Critical Role of lnterleukin-6 and its Crosstalk with AT1 R Signaling in Acute Rejection of Murine Cardiac Allografts," Circulation Journal, 71 (Suppl. 1):392 (#PE-269), Annual Scientific Meeting of the Japanese Circulation Society, Kobe, Japan (2007).
Izawa, et al., "Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," American Journal of Transplantation, 7(Suppl. 11):426 (#1084), American Transplant Congress, San Francisco (2007).
Jain, M., et al., "Engineering Antibodies for Clinical Applications," Trends in Biotechnology, 25(7):307-316, Elsevier Science Publishers, England (2007).
Janeway, C.A., et al., "Immunobiology, 3rd edition," Garland Press Inc., p. 11 (1997).
Janeway, et al Immunobiology, 5th edition. 2001:Extract from Chapter 3.
Janeway, et al Immunobiology, 5th edition. 2001:Extract from Chapter 4.
Japanese Society of Neurological Therapeutics, "Standard Neurological Therapeutics: Neuromyelitis Optica (NMO)," vol. 30, No. 6, pp. 777-794, 2003 (including a partial English translation).
Jego, G., et al., "Interleukin-6 is a Growth Factor for Nonmalignant Human Plasmablasts," Blood 97(6):1817-1822, American Society of Hematology, United States (Mar. 2001).
Jejurikar et al., "Skeletal Muscle Denervation Increases Satellite Cell Susceptibility to Apoptosis," Plastic and Reconstructive Surgery, 110:160-168 (2002).
Jeron, A., et al., "Systemic Immunosuppression Fails to Suppress Cardiac Cytokine Induction in Pressure Overload Hypertrophy in Rats," Immunobiology, 205(1):51-60, Elsevier, Netherlands (2002).
Johnson, K.A., et al., "Cation Exchange-HPLC and Mass Spectrometry Reveal C-Terminal Amidation of an IgG1 Heavy Chain," Analytical Biochemistry 360(1):75-83, Academic Press, United States (2007).
Jones, S.W., et al., "Disuse Atrophy and Exercise Rehabilitation in Humans Profoundly Affects the Expression of Genes Associated with the Regulation of Skeletal Muscle Mass," FASEB Journal 18(9):1025-1027, Federation of American Societies for Experimental Biology, United States (2004).
Jones, T.D., et al., "Identification and Removal of a Promiscuous CD4+ T Cell Epitope From the C1 Domain of Factor VIII," Journal of Thrombosis and Haemostasis, 3(5):991-1000, Blackwell Pub, England (2005).
Jourdan, M., et al., "An in Vitro Model of Differentiation of Memory B Cells Into Plasmablasts and Plasma Cells Including

(56) References Cited

OTHER PUBLICATIONS

Detailed Phenotypic and Molecular Characterization", Blood 114:5173-5181, American Society of Hematology, New York (2009).

Junghans, R.P. and Anderson, C.L., "The Protection Receptor for IgG Catabolism is the Beta2-Microglobulin-Containing Neonatal Intestinal Transport Receptor," Proceedings of the National Academy of Sciences of the United States of America 93(11):5512-5516, National Academy of Sciences, United States (1996).

Kabat, E.A., et al., "Sequences of Proteins of Immunological Interest," National Institute of Health, Publ'n No. 91-3242, 5th ed., 1:647-660 (1991).

Kai, et al., "Switching Constant Domains Enhances Agonist Activities of Antibodies to a Thrombopoietin Receptor," Nature Biotechnology, 26(2):209-11 (2008).

Kakita, M., et al., "Isolation of a Human Monoclonal Antibody With Strong Neutralizing Activity Against Diphtheria Toxin", Infection and Immunity, 74:3682-3683, American Society for Microbiology, United States (2006).

Kakuron III, "Section 9 Opticospinal Multiple Sclerosis," Tahatsusei Kokasho Chiryo Guideline, 104-109 (2010).

Kallen, K.-J., et al., "New Developments in Il-6 Dependent Biology and Therapy: Where Do We Stand and What Are the Options?," Expert Opinion on Investigational Drugs 8:1327-1349, (1999).

Kamata, N., et al., "Comparison of pH and Ionic Strength Dependence of Interactions between Monoclonal Antibodies and Bovine-Lactoglobulin," Bioscience Biotechnology Biochemistry, 60(1):25-29 (1996).

Kami, K., et al., "Gene Expression of Receptors for IL-6, LIF, and CNTF in Regenerating Skeletal Muscles", Journal of Histochemistry and Cytochemistry 48:1203-1213, SAGE Publications, United States (2000).

Kamohara, H., et al., "IL-6 no Suigan Saibo no Zoshoku-Ten'i Oyobosu Eikyo to Kanshitsu Saibo ni yoru Hatsugen Seigyo Kika," Japanese Journal of Gastroenterological Surgery, 39(7): 1356 (Abstract 2529) (2006).

Kampan, N.C., et al., "Immunotherapeutic Interleukin-6 or Interleukin-6 Receptor Blockade in Cancer: Challenges and Opportunities," Current Medicinal Chemistry 25(36):4785-4806 (2018).

Kan, S., et al., "The Effect of Anti-Cancer Agents on CD4+FoxP3+ Regulatory T Cell," Dai 68 Kai Annual Meeting of the Japan Cancer Association, p. 286, P-0539, (2009).

Kanda, T. and Takahashi, T., "Interleukin-6 and Cardiovascular Diseases," Japanese Heart Journal, 45(2):183-193, Japanese Heart Journal Association, Japan (2004).

Karin, M. and Lin, A., "NF-KB at the Crossroads of Life and Death", Nature Immunology 3:221-227, Nature Publishing Group, England (2002).

Karin, M., et al., "NF-kappaB in Cancer: From Innocent Bystander to Major Culprit," Nature Reviews Cancer 2(4):301-310, Nature Publishing Group, England (2002).

Kashmiri, S.V., et al., "Generation, Characterization, and in Vivo Studies of Humanized Anticarcinoma Antibody CC49," Hybridoma, 14(5):461-473, Mary Ann Liebert, United States (Oct. 1995).

Katayose, Y., et al., "MUC1-specific Targeting Immunotherapy With Bispecific Antibodies: Inhibition of Xenografted Human Bile Duct Carcinoma Growth," Cancer Research, 56(18):4205-4212, American Association for Cancer Research, United States (1996).

Kato, "A Case of Bronchial Asthma Where IL-6 Is Considered to Have Been Involved in Making It Refractory," Shindan to Chiryo, 106(10):1287-1291 (2018).

Kayahara, et al., "The Nature of Neural Invasion by Pancreatic Cancer," Pancreas, 35:218-223 (2007).

Kayahara, M., et al., "Neural Invasion and Lymph Node Metastasis in the Head of the Pancreas Carcinoma," The Japanese Journal of Gastroenterological Surgery 24(3):813-817, The Japanese Society of Gastroenterological Surgery, Japan (1991).

Khawli, L.A., et al., "Improved Tumor Localization and Radioimaging With Chemically Modified Monoclonal Antibodies," Cancer Biotherapy & Radiopharmaceuticals, 11(3):203-215, Mary Ann Liebert, Inc., C1996-, United States (1996).

Kim, I., et al., "Lowering of Pi by Acylation Improves the Renal Uptake of 99m Tc-labeled Anti-Tac DsFv: Effect of Different Acylating Reagents," Nuclear Medicine and Biology, 29(8):795-801, Elsevier, United States (Nov. 2002).

Kim, I.S., et al., "Chemical Modification to Reduce Renal Uptake of Disulfide-bonded Variable Region Fragment of Anti-Tac Monoclonal Antibody Labeled With 99m Tc," Bioconjugate Chemistry, 10(3):447-453, American Chemical Society, c1990-, United States (May-Jun. 1999).

Kim, S., et al., "Carcinoma-Produced Factors Activate Myeloid Cells Through TLR2 to Stimulate Metastasis," Nature, 457(7225):102-106, Nature Publishing Group, England (Jan. 2009).

Kim, S.J., et al., "Antibody Engineering for the Development of Therapeutic Antibodies," Molecules and Cells 20(1):17-29, Korean Society for Molecular and Cellular Biology, Korea (Aug. 2005).

King, D.J., Applications and Engineering of Monoclonal Antibodies, 146-147 (2005).

King, D., "Antibody Engineering: Design for Specific Applications," Applications and Engineering of Monoclonal Antibodies, 27-75, Chapter 2 (1998).

Kishimoto, T., "Interleukin-6 and its Receptor in Autoimmunity," Journal of Autoimmunity, 5(Suppl A):123-132 (1992).

Kishimoto, T., "The Biology of Interleukin-6," Blood, 74(1):1-10, American Society of Hematology, United States (Jul. 1989).

Kitahara, M., et al., "The in Vivo Anti-Tumor Effect of Human Recombinant Interleukin-6", Japanese Journal of Cancer Research 81:1032-1038, Japanese Cancer Association, Japan (Oct. 1990).

Kitazawa, R., et al., "Interleukin-1 Receptor Antagonist and Tumor Necrosis Factor Binding Protein Decrease Osteoclast Formation and Bone Resorption in Ovariectomized Mice," The Journal of Clinical Investigation 94(6):2397-2406, American Society for Clinical Investigation, United States (Dec. 1994).

Klein, B., et al., "Interleukin-6 in Human Multiple Myeloma," Blood 85(4): 863-872. The American Society of Hematology, United States (1995).

Knappik et al., "Fully Synthetic Human Combinatorial Antibody Libraries (HuCAL) Based on Modular Consensus Frameworks and CDRs Randomized with Trinucleotides," Journal of Molecular Biology, 296(1):57-86 (2000).

Knulst, A.C., et al., "Cytokine Detection and Modulation in Acute Graft vs. Host Disease in Mice,"Mediators of Inflammation, 3(1):33-40, Hindawi Publishing Corporation, United States (1994).

Kobara, M., et al., "Antibody Against Interleukin-6 Receptor Attenuates Left Ventricular Remodelling After Myocardial Infarction in Mice", Cardiovascular Research 87:424-430, Oxford Journals, London (Aug. 2010).

Kobara, M., et al., "Inhibition of Interleukin-6 Signaling Attenuates Left Ventricular Remodeling After Myocardian Infarction in Mice," Journal of the American Heart Association, 112(851), (2005).

Kobatake, K., et al., "Kdm6a Deficiency Activates Inflammatory Pathways, Promotes M2 Macrophage Polarization, and Causes Bladder Cancer in Cooperation with p53 Dysfunction," Clinical Cancer Research 26(8):2065-2079 (2020).

Kobayashi, T., et al., "A Monoclonal Antibody Specific for a Distinct Region of Hen Egg-white Lysozyme," Molecular Immunology, 19:619-30 (1982).

Kobayashi, H., et al., "The Pharmacokinetic Characteristics of Glycolated Humanized Anti-tac Fabs Are Determined by Their Isoelectric Points," Cancer Research, 59(2):422-430, American Association for Cancer Research, United States (1999).

Koch, S., et al., "IL-6 activated integrated BATF/IRF4 functions in lymphocytes are T-bet-independent and reversed by subcutaneous immunotherapy," Sci Rep., 3:1754 (2013).

Koide, N., et al., "Establishment of Perineural Invasion Models and Analysis of Gene Expression Revealed an Invariant Chain (CD74) as a Possible Molecule Involved in Perineural Invasion in Pancreatic Cancer," Clinical Cancer Research, 12(8):2419-2426, Denville, United States (Apr. 2006).

Komissarov, A.A., et al., "Site-Specific Mutagenesis of a Recombinant Anti-single-stranded DNA Fab. Role of Heavy Chain Complementarity-determining Region 3 Residues in Antigen Interaction,"

(56) References Cited

OTHER PUBLICATIONS

The Journal of Biological Chemistry, 272(43):26864-26870, American Society for Biochemistry and Molecular Biology, United States (1997).
Kondo, M., et al., "A Case of Overlap Syndrome Successfully Treated with Tocilizumab: A Hopeful Treatment Strategy for Refractory Dermatomyositis?", Rheumatology 53:1907-1908, Oxford University Press, England (Oct. 2014).
Konopatskaya, O., et al., Molecular Vision, Monday, May 1, 2006, 11:15 AM-1:00PM Hall B/C Poster Session Program Number/Board# Range: 1749-1764/B836-B851, 244. Antiangiogenesis: Basic Mechanisms.
Kosaka, H., et al., "Interferon-γ is a therapeutic target molecule for prevention of postoperative adhesion formation," Nat Med., 14(4):437-441 (2008).
Kotake, S., et al., "Interleukin-6 and Soluble Interleukin-6 Receptors in the Synovial Fluids From Rheumatoid Arthritis Patients Are Responsible for Osteoclast-like Cell Formation," Journal of Bone and Mineral Research, 11(1):88-95 (1996).
Kranz, D.M., et al., "Mechanisms of Ligand Binding by Monoclonal Anti-fluorescyl Antibodies," The Journal of Biological Chemistry, 257(12):6987-6995, American Society for Biochemistry and Molecular Biology, United States (Jun. 1982).
Kreutz, F.T., et al., "Efficient Bispecific Monoclonal Antibody Purification Using Gradient Thiophilic Affinity Chromatography," Journal of Chromatography. B, Biomedical Sciences and Applications, 714(2):161-170, Elsevier, Netherlands (Sep. 1998).
Krieckaert, C,L., et al., "Immunogenicity of Biologic Therapies—We Need Tolerance," Nature Reviews. Rheumatology 6:558-559, Nature Pub. Group, United States (Oct. 2010).
Kurdi, M., et al., "Increased Expression of IL-6 and LIF in the Hypertrophied Left Ventricle of TGR(mRen2)27 and SHR rats," Molecular and Cellular Biochemistry 269(1-2):95-101, Springer, Netherlands (Jan. 2005).
Kurek, J.B., et al., "The Role of Leukemia Inhibitory Factor in Skeletal Muscle Regeneration," Muscle Nerve, 20:815-822 (1997).
Kurek, J.B., et al., "Up-regulation of Leukaemia Inhibitory Factor and Interleukin-6 in Transected Sciatic Nerve and Muscle Following Denervation," Neuromuscular Disorders, 6(2):105-114, Pergamon Press, England (Mar. 1996).
Kuroda, D., et al., "Computer-Aided Antibody Design," Protein Engineering, Design & Selection 25:507-521, Oxford University Press, England (Oct. 2012).
Kuroda, K., et al., "Prevention of Cancer Cachexia by a Novel Nuclear Factor kB Inhibitor in Prostate Cancer," Clinical Cancer Research 11(15):5590-5594, American Association for Cancer Research, United States (Aug. 2005).
Latulippe, E., et al., "Comprehensive Gene Expression Analysis of Prostate Cancer Reveals Distinct Transcriptional Programs Associated with Metastatic Disease," Cancer Research 62:4499-4506, American Association for Cancer Research (Aug. 2002).
Laitinen et al., "Brave New (Strept)Avidins in Biotechnology," Trends Biotechnol., 25(6):269-77 (2007).
Lancaster, J.M., et al., "Identification of Genes Associated with Ovarian Cancer Metastasis Using Microarray Expression Analysis," International Journal of Gynecological Cancer, 16(5):1733-1745, Blackwell Scientific Publications, England (Sep.-Oct. 2006).
Lechner, M.G., et al., "Characterization of Cytokine-Induced Myeloid-Derived Suppressor Cells from Normal Human Peripheral Blood Mononuclear Cells," Journal of Immunology 185:2273-2284 (2010).
Lee, C.V., et al., "High-Affinity Human Antibodies From Phage-displayed Synthetic Fab Libraries With a Single Framework Scaffold," Journal of Molecular biology 340(5):1073-1093, Elsevier, England (Jul. 2004).
Lee, S.O., et al., "Interleukin-6 Protects LNCaP Cells From Apoptosis Induced by Androgen Deprivation Through the Stat3 Pathway," The Prostate 60(3):178-186, Wiley-Liss, United States (Aug. 2004).
Leong, S.R., et al., "Adapting Pharmacokinetic Properties of a Humanized Anti-interleukin-8 Antibody for Therapeutic Applications Using Site-specific Pegylation," Cytokine, 16(3):106-119, Elsevier Science Ltd, England (2001).
Ler, L.D., et al., "Loss of Tumor Suppressor KDM6A Amplifies PRC2-Regulated Transcriptional Repression in Bladder Cancer and Can be Targeted Through Inhibition of EZH2," Science Translational Medicine 9(378):eaai8312 (2017).
Li, B., et al., "Construction and Characterization of a Humanized Anti-human Cd3 Monoclonal Antibody 12f6 With Effective Immunoregulation Functions," Immunology 116(4):487-498, Blackwell Scientific Publications, England (Dec. 2005).
Li et al., "Phase II Study of the Proteasome Inhibitor Bortezomib (PS-341, Velcade®) in Chemotherapy-Naive Patients with Advanced Stage in Non-Small Cell Lung Cancer (NSCLC)," Lung Cancer, vol. 68:89-93, 2010.
Lin, Y.S., et al., "Preclinical Pharmacokinetics, Interspecies Scaling, and Tissue Distribution of a Humanized Monoclonal Antibody Against Vascular Endothelial Growth Factor," The Journal of Pharmacology and Experimental Therapeutics, 288(1):371-378, Williams & Wilkins, United States (Jan. 1999).
Lin, Y.-L., et al., "Critical role of IL-6 in dendritic cell-induced allergic inflammation of asthma," J Mol Med., 94:51-59 (2016).
Linder, M., et al., "Design of a pH-dependent Cellulose-Binding Domain," FEBS Letters, 447(1):13-16, Wiley Publishing Company, England (Mar. 1999).
Lindhofer, H., et al., "Preferential Species-restricted Heavy/light Chain Pairing in Rat/mouse Quadromas. Implications for a Single-step Purification of Bispecific Antibodies," Journal of Immunology, 155(1):219-225, American Association of Immunologists, United States (Jul. 1995).
Liu, H., et al., "Heterogeneity of Monoclonal Antibodies," Journal of Pharmaceutical Sciences, 97(7):2426-2447, Elsevier, United States (Jul. 2008).
Lobo, E.D., et al., "Antibody Pharmacokinetics and Pharmacodynamics," Journal of Pharmaceutical Sciences, 93(11):2645-2668, Elsevier, United States (Nov. 2004).
Lotz, M., et al., "B Cell Stimulating Factor 2/interleukin 6 is a Costimulant for Human Thymocytes and T Lymphocytes," Journal of Experimental Medicine 167:1253-1258, (Mar. 1988).
Lucchinetti, C., et al., "Heterogeneity of Multiple Sclerosis Lesions: Implications for the Pathogenesis of Demyelination," Annals of Neurology 47(6):707-717, Wiley-Liss, United States (Jun. 2000).
Lund, J., et al., "Expression and Characterization of Truncated Forms of Humanized L243 IgG1. Architectural Features Can Influence Synthesis of Its Oligosaccharide Chains and Affect Superoxide Production TrIgGered Through Human Fcgamma Receptor I," European Journal of Biochemistry 267(24):7246-7257, Blackwell Science Ltd. on behalf of the Federation of European Biochemical Societies, England (Dec. 2000).
Luo, H., et al., "A Proteasome Inhibitor Effectively Prevents Mouse Heart Allograft Rejection," Transplantation, 72(2):196-202 (2001).
Maccallum, R.M., et al., "Antibody-antigen Interactions: Contact Analysis and Binding Site Topography," Journal of Molecular Biology 262(5):732-745, Academic Press, England (Oct. 1996).
Madhok, R., et al., "Serum Interleukin 6 Levels in Rheumatoid Arthritis: Correlations With Clinical and Laboratory Indices of Disease Activity," Annals of the Rheumatic Diseases, 52(3):232-234, BMJ, England (Mar. 1993).
Maeda, et al., "Essential Roles of Nf-KB Activation for Development of Liver Metastasis in Mice," Gastroenterology, JJO:P-I-P-350, Supplement 2, AASLD Abstracts, p. A-750, Abstract No. 107, (2006).
Maeda, et al., "IKKBeta Couples Hepatocyte Death to Cytokine-driven Compensatory Proliferation That Promotes Chemical Hepatocarcinogenesis," Cell, 121:977-990 (2005).
Maeda, et al., "Role of iKKbeta I NF-KB Activation for Development of Liver Metastasis," Supplement: The 58th Annual Meeting of the American Association for the Study of Liver Diseases, Hepatol., 46:Issue Supplement SI, AASLD Abstracts, p. 518A, abstract No. 630, AASLD (2007).
Maeda, K., et al., "pH-Dependent Receptor/Ligand Dissociation as a Determining Factor for Intracellular Sorting of Ligands for

(56) References Cited

OTHER PUBLICATIONS

Epidermal Growth Factor Receptors in Rat Hepatocytes," Journal of Controlled Release, 82(1):71-82, Elsevier Science Publishers, Netherlands (Jul. 2002).

Maeda, S., et al., "Ikappa B Kinasebeta/nuclear Factor-kappaB Activation Controls the Development of Liver Metastasis by Way of Interleukin-6 Expression," Hepatology 50:1851-1860, American Association for the Study of Liver Diseases, United States, (Dec. 2009).

Maier, J.K.X. and Labute, P., "Assessment of Fully Automated Antibody Homology Modeling Protocols in Molecular Operating Environment," Proteins 82(8):1599-1610, Wiley-Liss, United States (Aug. 2014).

Maini, R.N., et al., "Double-blind Randomized Controlled Clinical Trial of the Interleukin-6 Receptor Antagonist, Tocilizumab, in European Patients With Rheumatoid Arthritis Who Had an Incomplete Response to Methotrexate," Arthritis and Rheumatism, 54(9):2817-2829, Wiley-Blackwell, United States (Sep. 2006).

Manzke, O., et al., "Single-step Purification of Bispecific Monoclonal Antibodies for Immunotherapeutic Use by Hydrophobic Interaction Chromatography," Journal of Immunological Methods, 208(1):65-73, Elsevier, Netherlands (Oct. 1997).

Marshall, S.A, et al., "Rational Design and Engineering of Therapeutic Proteins," Drug Discovery Today, 8(5):212-221, Distributed by Virgin Mailing and Distribution, c1996-, England (2003).

Marten, A., et al., "Bortezomib is Ineffective in an Orthotopic Mouse Model of Pancreatic Adenocarcinoma," Molecular Cancer Therapeutics, 7:3624-3631 (2008).

Martignoni, M.E., et al., "Role of Mononuclear Cells and Inflammatory Cytokines in Pancreatic Cancer-related Cachexia," Clinical Cancer Research, 11(16):5802-5808, Denville, United States (Aug. 2005).

Martin, W.L., et al., "Crystal Structure at 2.8 a of an Fcrn/heterodimeric Fc Complex: Mechanism of Ph-dependent Binding," Molecular Cell, 7(4):867-877, Cell Press, United States (Apr. 2001).

Martinez, T., et al., "Disulfide Connectivity of Human Immunoglobulin G2 Structural Isoforms," Biochemistry 47(28):7496-7508, American Chemical Society, United States (Jul. 2008).

Marvin, J.S and Lowman, H.B., "Redesigning an Antibody Fragment for Faster Association With Its Antigen," Biochemistry, 42(23):7077-7083, American Chemical Society, United States (Jun. 2003).

Marvin, J.S and Zhu, Z., "Recombinant Approaches to Igg-like Bispecific Antibodies," Acta Pharmacologica Sinica, 26(6):649-658, Nature Publishing Group, United States (Jun. 2005).

Massoud, A. H., et al., "An asthma-associated IL4R variant exacerbates airway inflammation by promoting conversion of regulatory T cells to $T^H17$-like cells," Nat Med., 22(9):1013-1022 (2016).

Masui, T., et al., "Expression of IL-6 Receptor in Pancreatic Cancer: Involvement in VEGF Induction," Anticancer Research 22:4093-4100 (2002).

Matsuda, T., et al., "Establishment of an Interleukin 6 (IL 6)/B Cell Stimulatory Factor 2-Dependent Cell Line and Preparation of Anti-IL 6 Monoclonal Antibodies," European Journal of Immunology 18:951-956, Wiley-VCH, Germany (Jun. 1988).

Matsumoto, M., et al., "Interleukin-10-Producing Plasmablasts Exert Regulatory Function in Autoimmune Inflammation," Immunity 41(6):1040-1051, Cell Press, United States (Dec. 2014).

Matsushita, et al., "Lnterleukin-6 soluble lnterleukin-6 Receptor Complex Reduces Infarct Size via Inhibiting Myocardial Apoptosis," Laboratory Investigation, 85:1210-1223 (2005).

Maizaraki, V., et al., "Evaluation of Serum Procalcitonin and Interleukin-6 Levels as Markers of Liver Metastasis," Clinical Biochemistry, 40(5-6):336-342, Elsevier Science, United States (Mar. 2007).

Mauro, A., "Satellite Cell of Skeletal Muscle Fibers," Journal of Biophysical and Biochemical Cytology 9:493-495, Rockefeller Institute for Medical Research, United States (Feb. 1961).

Maxfield, F.R. and McGraw, T.E., "Endocytic Recycling," Nature Reviews Molecular Cell Biology 5(2):121-132, Nature Pub. Group, England (Feb. 2004).

Maynard et al., "Antibody Engineering," Annual Review of Biomedical Engineering, 2:339-76 (2000).

Mccormick, K.M. and Schultz, E., "Role of Satellite Cells in Altering Myosin Expression During Avian Skeletal Muscle Hypertrophy," Developmental dynamics, 199(1):52-63, Wiley, United States (Jan. 1994).

U.S. National Library of Medicine, MedlinePlus, National Institutes of Health, accessed Nov. 22, 2014.

Mellman, I., "The Importance of Being Acid: The Role of Acidification in Intracellular Membrane Traffic," The Journal of Experimental Biology 172:39-45, Company of Biologists Limited, England (Nov. 1992).

Meng, F., et al., "Acquired Resistance to Chemotherapy in Human Cholangiocarcinoma Is Mediated by an Interleukin (il-6) Dependent Activation of the X-Linked Inhibitor of Apoptosis (xiap) Protein," Gastroenterology 128(4):Supplemental 2:A-30, Abstract No. 165 (2005).

Meng, F., et al., "Over-expression of Interleukin-6 Enhances Cell Survival and Transformed Cell Growth in Human Malignant Cholangiocytes," Journal of Hepatology 44:1055-1065, Elsevier B.V., Netherlands (2006).

Merchant, A.M., et al., "An Efficient Route to Human Bispecific IgG," Nature Biotechnology 16(7):677-681, Nature America Publishing, United States (Jul. 1998).

Michalaki et al., "Serum Levels of IL-6 and TNF-a Correlate with Clinicopathological Features and Patient Survival in Patients with Prostate Cancer," British Journal of Cancer 90:2312-2316 (2004).

Mihara, M., et al., "Anti-interleukin 6 Receptor Antibody Inhibits Murine Aa-amyloidosis," The Journal of Rheumatology, 31(6):1132-1138, Journal of Rheumatology Publishing Co, Canada (Jun. 2004).

Mihara, M., et al., "Tocilizumab Inhibits Signal Transduction Mediated by both mIL-6R and sIL-6R, but not by the Receptors of Other Members of IL-6 Cytokine Family," Int. Immunopharmacol 5:1731-1740, Elsevier Science, Netherlands (Nov. 2005).

Miller, D.H., et al., "Differential Diagnosis of Suspected Multiple Sclerosis: A Consensus Approach," Multiple sclerosis 14(9):1157-1174, SAGE Publications, England (Nov. 2008).

Ming, et al., "IL-6 Enhances the Generation of Cytolytic T Lymphocytes in the Allogeneic Mixed Leucocyte Reaction", Clinical and Experimental Immunology, 89(1):148-153 (1992).

Mitsunaga, S., et al., "Detail Histologic Analysis of Nerve Plexus Invasion in Invasive Ductal Carcinoma of the Pancreas and Its Prognostic Impact," The American Journal of Surgical Pathology, 31(11):1636-1644, Wolters Kluwer Health, United States (Nov. 2007).

Mitsunaga, S., et al., "Nerve Invasion Distance is Dependent on Lamimin gamma2 in Tumors of Pancreatic Cancer," International Journal of Cancer 127:805-819, Wiley-Liss, United States (Aug. 2010).

Miyamoto, Y., et al., "lnterleukin-6 Inhibits Radiation Induced Apoptosis in Pancreatic Cancer Cells," Anticancer Research 21(4A):2449-2456, International Institute of Anticancer Research, Greece (Jul.-Aug. 2001).

Mohan, et al., CALBIOCHEM Buffers, "A guide for the preparation and use of buffers in biological systems," by chandra Mohan, Ph.D.,Copyright 2003 EMD Biosciences, Inc.,an Affliate of Merck K GaA, Darmastadt, Germany ,37pages (CALBIOCHEM Buffers Booklet, 2003).

Montero-Julian et al., "Pharmacokinetic Study of Anti-interleukin-6 (Il-6) Therapy With Monoclonal Antibodies: Enhancement ifil-6 Clearance by Cocktails of Anti-il-6 Antibodies," Blood, 85(4):917-924 (1995).

Mori, K., et al., "Novel Models of Cancer-related Anemia in Mice Inoculated With Il-6-producing Tumor Cells," Biomedical Research, 30(1):47-51, Biomedical Research Foundation, Japan (Feb. 2009).

Moss, F.P. and Leblond, C,P., "Satellite Cells as the Source of Nuclei in Muscles of Growing Rats," The Anatomical Record 170:421-435, A.R. Liss, United States (Aug. 1971).

(56) References Cited

OTHER PUBLICATIONS

Motozawa, N., et al., "Unique Circumferential Peripheral Keratitis in Relapsing Polychondritis: A Case Report," Medicine 96(41):e7951, Lippincott Williams & Wilkins, United States (Oct. 2017).

Mozdziak et al., "Hindlimb Suspension Reduces Muscle Regeneration," Journal of Applied Physiology, 78:136-140 (1998).

Mozdziak, P.E., et al., "Muscle Regeneration During Hindlimb Unloading Results in a Reduction in Muscle Size After Reloading," Journal of Applied Physiology, 91(1):183-190, American Physiological Society, United States (Jul. 2001).

Mozdziak, P.E., et al., "Quantitation of Satellite Cell Proliferation in Vivo Using Image Analysis," Biotech. Histochem 69:249-252, Oxford: Taylor & Francis, England (Sep. 1994).

Mozdziak, P.E., et al., "Unloading of Juvenile Muscle Results in a Reduced Muscle Size 9 wk After Reloading," Journal of Applied Physiology 88(1):158-164, American Physiological Society, United States (Jan. 2000).

Mukaida, et al., "Cytokines and Immune Network," Rinsho Kensa 35:447-452 (1991).

Mulhearn, B., et al., "Using the Immunophenotype to Predict Response to Biologic Drugs in Rheumatoid Arthritis," J Pers Med., 9:46 (2019).

Muller, Y.A., et al., "VEGF and the Fab Fragment of a Humanized Neutralizing Antibody: Crystal Structure of the Complex at 2.4 a Resolution and Mutational Analysis of the Interface," Structure, 6(9):1153-1167, Cell Press, United States (Sep. 1998).

Murata, et al., "Development Mechanism and Pathophysiology," Saishin-Igaku 47:49-56, (1992).

Murata, V.M., et al., "Anti-digoxin Fab Variants Generated by Phage Display," Molecular Biotechnology, 54(2):269-277, Humana Press, c1994-, United States (Jun. 2013).

Murphy, "The effect of mechanical stretch on proliferation and differentiation ofC2C12 cells," FASEBJ, 18:A743 (Abstract#476.6) (2004).

Murtaugh, M.L., et al., "A Combinatorial Histidine Scanning Library Approach to EngineerHighly pH-Dependent Protein Switches," Protein Science 20(9):1619-1631, Cold Spring Harbor Laboratory Press, United States (Sep. 2011).

Nagai, et al., "Suppression of Experimental Choroid Neovascularization by Inhibition oflnterleukin-6 Receptor," Inflammation and Regeneration 26:367 (#90), 2006 (English translation included).

Nakamura, et al., "Clinical Characteristics of Multiple Sclerosis with High Peripheral Blood Plasmablast Frequency," Meeting Abstract, 54th Annual Meeting of the Japanese Society of Neurology, Japan (Apr. 2013) (English translation).

Nakamura, et al., "Clinical Features of Multiple Sclerosis with High Plasmablast Frequency in Peripheral Blood," Abstract for Poster Session, Multiple Sclerosis, Keystone Symposia on Molecule and Cellular Biology, Big Sky, Montana, distributed (Jan. 2013).

Nakamura et al., "Clinical Features of Multiple Sclerosis with High Plasmablast Frequency in Peripheral Blood," Abstract, Multiple Sclerosis, Keystone Symposia on Molecule and Cellular Biology, Big Sky, Montana, published online Dec. 11, 2012.

Nakamura et al., "Clinical Features of Multiple Sclerosis with High Plasmablast Frequency in Peripheral Blood," Poster Session, 54th Annual Meeting of the Japanese Society of Neurology, Tokyo, Japan, presented Jun. 1, 2013 (with English translation).

Nakamura et al., "Clinical Features of Multiple Sclerosis with High Plasmablast Frequency in Peripheral Blood," Poster Session, Multiple Sclerosis, Keystone Symposia on Molecular and Cellular Biology, Big Sky, Montana, (Jan. 2013).

Nakamura, et al., "IL-6-dependent Plasmablasts in Pathological Conditions of Relapsing-Remitting Multiple Sclerosis," Japanese Journal of Clinical Immunology 36:345, (2013) W5-5 (with English translation).

Nakamura, M., et al., "Plasmablast in the Pathology of Multiple Sclerosis," Japanese Journal of Clinical Immunology 38(5):403-411, Nihon Rinsho Men'eki Gakkai, Japan (2015 (English Abstract)).

Nakamura, T., "Cancer Prevention by NK 4 to Act as an Inhibitor of Tumor Iinvasion, Metastasis and Angiogenesis," The Basics and Clinical Aspects of Angiogenesis-[II] Angiogenesis and Tumors, 8. Invasion/Metastasis/tumor Suppression of Angiogenesis-Inhibitory Factor AK 4, pp. 57-66, Japanese Association of Medical Sciences (2002).

Nakashima, et al., "Serum Interleukin 6 as a Prognostic Factor in Patients with Prostate Cancer," Clinical Cancer Research 6:2702-2706 (2000).

Narazaki, M., et al., "Therapeutic Effect of Tocilizumab on Two Patients with Polymyositis," Rheumatology, 50(7):1344-1346, Oxford University Press, England (Jul. 2011).

Narhi, L.O., et al., "Effect of Three Elution Buffers on the Recovery and Structure of Monoclonal Antibodies," Analytical Biochemistry 253(2):236-245, Elsevier, United States (Nov. 1997).

Narita, et al., "Gemcitabine Selectively Depletes CDIIb+ Gr-1 + Immature Myeloid Cells in Tumor-Bearing Mice and Enhances Anti-Tumor Immune Response," Society for Fundamental Cancer Immunology Sakai Shoroku 10:49, 2006 (with an unverified English translation).

National Cancer Institute, "SEER Cancer Stat Facts: Pancreas Cancer," https://seer.cancer.gov/statfacts/html/pancreas.html, National Cancer Institute, Bethesda, Maryland, United States, accessed Apr. 25, 2017 (9 pages).

National Cancer Institute, U.S. National Institutes of Health, "Metastatic Cancer: Questions and Answers," accessed Nov. 22, 2014.

Naugler, W.E., et al., "Gender Disparity in Liver Cancer Due to Sex Differences in MyD88-Dependent IL-6 Production," Science 317:121-124, American Association for the Advancement of Science, United States (Jul. 2007).

Negoro, S., et al., "Activation of JAK/STAT Pathway Transduces Cytoprotective Signal in Rat Acute Myocardial Infarction," Cardiovascular Research 47(4):797-805, Oxford Journals, England (Sep. 2000).

Nesterova, et al., "Glypican-3 as a Novel Target for an Antibody-Drug Conjugate," American Association for Cancer Research Abstract No. 656, Los Angeles, CA (2007).

Newman, R., et al., "Modification of the Fc Region of a Primatized IgG Antibody to Human Cd4 Retains Its Ability to Modulate Cd4 Receptors but Does Not Deplete Cd4(+) T Cells in Chimpanzees," Clinical Immunology 98(2):164-174, Academic Press, United States (Feb. 2001).

Ngo, J.T., et al., "Computational Complexity Protein Structure Prediction, and the Levinthal Paradox," The Protein Folding Problem and Tertiary Structure Prediction, pp. 433-440 and 492-495, Merz and LeGrand (eds.), Birkhauser Boston, (1994).

Nishimoto et al., "Clinical Studies in Patients With Castleman's Disease, Crohn's Disease, and Rheumatoid Arthritis in Japan," Clinical Reviews in Allergy & Immunology, 28(3):221-30 (Jun. 2005).

Nishimoto, "Humanized anti-IL-6 Receptor Antibody (Tocilizumab)," Nihon Rinsho, 65(7):1218-26 (2007) (with English translation).

Nishimoto, N., and Kishimoto T., "Humanized Antihuman IL-6 Receptor Antibody, Tocilizumab," Handbook of Experimental Pharmacology 181:151-160, Springer-Verlag, Germany (2008).

Nishimoto, N., and Kishimoto T., "Inhibition of IL-6 for the Treatment of Inflammatory Diseases," Current Opinion in Pharmacology 4:386-391, Elsevier Science, England (Aug. 2004).

Nishimoto, N., "Clinical Studies in Patients With Castleman's Disease, Crohn's Disease, and Rheumatoid Arthritis in Japan," Clinical Reviews in Allergy & Immunology 28(3):221-229, Humana Press, United States (Jun. 2005).

Nishimoto, N., et al., "Anti-Interleukin 6 Receptor Antibody Treatment in Rheumatic Disease," Annals of the Rheumatic Diseases 59 Suppl 1 :i21-i27, BMJ, England (Nov. 2000).

Nishimoto, N., et al., "Humanized Anti-interleukin-6 Receptor Antibody Treatment of Multicentric Castleman Disease," Blood, 106(8):2627-2632, American Society of Hematology, United States (2005).

Nishimoto, N., et al., "Interleukin 6: From Bench to Bedside," Nature Clinical Practice. Rheumatology, 2(11):619-626., Nature Pub. Group, c2005-, United States (Nov. 2006).

Nordlund, H.R., et al., "Introduction of Histidine Residues Into Avidin Subunit Interfaces Allows Ph-dependent Regulation of Qua-

(56) References Cited

OTHER PUBLICATIONS ternary Structure and Biotin Binding," FEBS Letters,555(3):449-454, John Wiley & Sons Limited, England (Dec. 2003).
Notice of Allowance dated Aug. 22, 2011 for U.S. Appl. No. 12/085,065, Okada, M., et al., dated Jun. 1, 2009.
Notice of Allowance dated Feb. 24, 2012 for U.S. Appl. No. 12/680,087, Igawa, T., et al., filed Jan. 3, 2011.
Notice of Allowance dated Jun. 26, 2012 for U.S. Appl. No. 12/680,087, Igawa, T., et al., filed Jan. 3, 2007.
Notice of Allowance dated Aug. 27, 2012 for U.S. Appl. No. 12/090,061, Yasunami, Y., et al., filed Mar. 6, 2009.
Notice of Allowance dated Apr. 15, 2013 in U.S. Appl. No. 12/680,087, Igawa, T., et al., filed Jan. 3, 2011.
Notice of Allowance dated Aug. 2, 2013, in U.S. Appl. No. 12/680,087, Igawa, T., et al., filed Jan. 3, 2011.
Notice of Allowance dated Jan. 11, 2012 in U.S. Appl. No. 12/085,065, Okada, M., filed Jun. 1, 2009.
Notice of Allowance dated Mar. 22, 2013 in U.S. Appl. No. 12/090,061, Yasumami, Y., filed Mar. 6, 2009.
Notice of Allowance dated Nov. 26, 2012, in U.S. Appl. No. 12/680,087, Igawa, T., et al., filed Jan. 3, 2011.
Notice of Allowance dated Sep. 24, 2013, in U.S. Appl. No. 12/085,065, Okada, M., et al., filed Jun. 1, 2009.
Novick, et al., "Monoclonal Antibodies to the Soluble Human IL-6 Receptor: Affinity Purification, ELISA, and Inhibition of Ligand Binding," Hybridoma 10:137-146, (Feb. 1991).
Ober, R.J., et al., "Visualizing the Site and Dynamics of IgG Salvage by the MHC Class I-related Receptor, FcRn," Journal of Immunology 172(4):2021-2029, American Association of Immunologists, United States (Feb. 2004).
Restriction Requirement dated Feb. 2, 2011 in U.S. Appl. No. 12/094,644, Nakashima, et al., filed Feb. 27, 2009.
Office Action dated Aug. 16, 2011, in U.S. Appl. No. 12/161,733, Ishida, et al., filed Mar. 9, 2009.
Final Office Action dated Aug. 2, 2013, in U.S. Appl. No. 12/679,922, Igawa, et al., filed Oct. 1, 2010.
Office Action dated Dec. 21, 2011, in U.S. Appl. No. 12/524,041, Takahashi, et al., filed Sep. 18, 2009.
Restriction Requirement dated Feb. 26, 2019, in U.S. Appl. No. 15/575,027, Yamamura, et al., filed Nov. 17, 2017.
Office Action dated Jan. 12, 2012, in U.S. Appl. No. 12/090,061, Yasunami, et al., filed Mar. 6, 2009.
Restriction Requirement dated Jun. 1, 2012, in U.S. Appl. No. 12/996,162, Mitsunaga, et al., filed Mar. 7, 2011.
Office Action dated Mar. 15, 2013, in U.S. Appl. No. 12/524,041, Takahashi, et al., filed Sep. 18, 2009.
Office Action dated Mar. 26, 2013 in U.S. Appl. No. 13/387,292, Maeda, filed Apr. 3, 2012.
Office Action dated May 22, 2012, in U.S. Appl. No. 12/094,644, Nakashima, et al., filed Feb. 27, 2009.
Office Action dated Nov. 14, 2012, in U.S. Appl. No. 13/595,139, Kawashima, et al., filed Aug. 22, 2012.
Office Action dated Nov. 26, 2010 in U.S. Appl. No. 12/085,065, Okada, et al., filed Jun. 1, 2009.
Office Action dated Oct. 25, 2019 in U.S. Appl. No. 15/575,027, Yamamura, et al., filed Nov. 17, 2017.
Final Office Action dated Jan. 30, 2019 in U.S. Appl. No. 14/897,498, filed Dec. 10, 2015.
Office Action dated Jun. 22, 2018 in U.S. Appl. No. 14/897,498, filed Dec. 10, 2015.
Office Action dated Feb. 29, 2012 in U.S. Appl. No. 12/680,112, Igawa, et al., filed Jun. 23, 2010.
Office Action dated Sep. 12, 2012 in U.S. Appl. No. 12/996,162, Mitsunaga, et al., filed Mar. 7, 2011.
Office Action dated Feb. 23, 2018 in U.S. Appl. No. 15/263,617, Igawa, et al., Sep. 13, 2016.
Office Action dated Dec. 29, 2017 in U.S. Appl. No. 15/495,026, Igawa, et al., filed Apr. 24, 2017.
Office Action dated Sep. 30, 2013 in U.S. Appl. No. 13/524,528, Igawa, et al., filed Jun. 15, 2012.
Office Action dated Oct. 6, 2010 in U.S. Appl. No. 12/090,676, Kobara, et al., filed Feb. 25, 2009.
Office Action dated Dec. 20, 2010 in U.S. Appl. No. 12/296,193, Nishimoto, et al., filed Apr. 15, 2009.
Office Action dated Feb. 14, 2013 in U.S. Appl. No. 12/680,082, Igawa, et al., filed Jun. 25, 2010.
Office Action dated Feb. 4, 2013 in U.S. Appl. No. 12/680,112, Igawa, et al., filed Jun. 23, 2010.
Office Action dated Jan. 3, 2013 in U.S. Appl. No. 12/679,922, Igawa, et al., filed Oct. 1, 2010.
Office Action dated Jul. 2, 2013 in U.S. Appl. No. 13/257,145, Igawa, et al., filed Nov. 22, 2011.
Office Action dated Jun. 28, 2011 in U.S. Appl. No. 12/295,039, Igawa, et al., filed Jan. 20, 2009.
Office Action dated May 13, 2015 in U.S. Appl. No. 13/637,415, Igawa, et al., filed Feb. 4, 2013.
Office Action dated May 23, 2017 in U.S. Appl. No. 13/637,415, Igawa, et al. filed Feb. 4, 2013.
Office Action dated May 3, 2011 in U.S. Appl. No. 12/090,061, Yasunami, et al., filed Mar. 6, 2009.
Office Action dated Nov. 7, 2012 in U.S. Appl. No. 12/936,587, Igawa, et al., filed Jan. 3, 2011.
Office Action dated Oct. 27, 2011 in U.S. Appl. No. 12/680,087, Igawa, et al., filed Jan. 3, 2011.
Office Action dated Sep. 26, 2011 in U.S. Appl. No. 12/094,644, Nakashima, et al., filed Feb. 27, 2009.
Office Action dated Jul. 7, 2015 in U.S. Appl. No. 13/387,292, Maeda, filed Apr. 3, 2012.
Office Action dated May 21, 2014 in U.S. Appl. No. 13/387,292, Maeda, filed Apr. 3, 2012.
Office Action dated Nov. 13, 2017 in U.S. Appl. No. 12/996,162, Mitsunaga, et al., filed Mar. 7, 2011.
Office Action dated Sep. 22, 2016 in U.S. Appl. No. 13/387,292, Maeda, filed Apr. 3, 2012.
Ogata, T., et al., "Anti-IL-6 Receptor Antibody Does Not Ameliorate Radiation Pneumonia in Mice," Experimental and Therapeutic Medicine 4:273-276, Spandidos, Greece (Aug. 2012).
Ogata, T., et al., "Early Administration of IL-6RA Does Not Prevent Radiation-Induced Lung Injury in Mice," Radiation Oncology 5:26, BioMed Central, England (Apr. 2010).
Ohashi, K., et al., "Interferon γ and plasminogen activator inhibitor 1 regulate adhesion formation after partial hepatectomy," BJS, 101:398-407 (2014).
Ohno et al., "Antigen-Binding Specificities of Antibodies Are Primarily Determined by Seven Residues of VH," Proceedings of the National Academy of Sciences U.S.A., 82(9):2945-9 (May 1985).
Ohsugi, et al., "Success Story of Pre-market Approved Pipeline," Pharm. Stage 7:13-18 (2007).
Ohsugi, Y. and Tsuchimoto, N., "Pharmacological and Clinical Profile ofHumanized Anti-human IL-6 Receptor Antibody (Tocilizumab), a Therapeutic Drug for Castleman's Disease," Folia Pharmacologica Japonica, 126(6):419-425, Nippon Yakuri Gakkai, Japan (Dec. 2005) (with English translation).
Ohtsuka, et al., "Relation of Circulating Interleukin-6 to Left Ventricular Remodeling in Patients With Reperfused Anterior Myocardial Infarction," Clinical Cardiology, 27(7):417-420 (2004).
Okabe, "Proprietary Innovative Antibody Engineering Technologies in Chugai Pharmaceutical," pp. 78 (Dec. 2012).
Okada, et al., "IL-6/BSF-2 Functions as a Killer Helper Factor in the in Vitro Induction of Cytotoxic T Cells," Journal of Immunology. 141:1543-1549 (1988).
Okada, S., et al., "Elevated Serum Interleukin-6 Levels in Patients with Pancreatic Cancer," Japanese Journal of Clinical Oncology 28:12-15, Foundation of Clinical Oncology, Tokyo, Japan (Jan. 1998).
Okada, Y., et al., "Experimental Implication of Celiac Ganglionotropic Invasion of Pancreatic-Cancer Cells Bearing C-Ret Proto-Oncogene With Reference to Glial-cell-line-derived Neurotrophic Factor (GDNF)," International Journal of Cancer 81(1):67-73, Wiley-Liss, United States (Mar. 1999).

(56) References Cited

OTHER PUBLICATIONS

Okamoto, et al., "Inhibition of Interleukin-6 Signaling Attenuates Left Ventricular Remodeling After Experimental Myocardial Infarction," Journal of Cardiac Failure, 11(9): P066 (2005).

Okamoto, M., et al., "Interleukin-6 as a Paracrine and Autocrine Growth Factor in Human Prostatic Carcinoma Cells in Vitro," Cancer Research 57:141-146, American Association for Cancer Research, United States (Jan. 1997).

Okazaki, M., et al., "Characterization of Anti-Mouse Interleukin-6 Receptor Antibody," Immunology Letters 84(3):231-240, Elsevier/North-Holland Biomedical Press, Netherlands (Dec. 2002).

Okiyama, et al., "Therapeutic Effects of Interleukin-6 Blockade in a Murine Model of Polymyositis That Does Not Require Interleukin-17A," Arthritis & Rheumatism, 60(8):2505-2512 (2009).

Onda, M., et al., "Lowering the Isoelectric Point of the Fv Portion of Recombinant Immunotoxins Leads to Decreased Nonspecific Animal Toxicity Without Affecting Antitumor Activity," Cancer Research, 61(13):5070-5077, American Association for Cancer Research, United States (Jul. 2001).

Ono, et al., "The Effect of IL-6 on the Des-gamma-carboxy Prothrombin Synthesis in Human Hepatoma Cells," Gastroenterologia Japonica 27:745-750, Springer (1992).

Ono, K., et al., "Cytokine Gene Expression After Myocardial Infarction in Rat Hearts: Possible Implication in Left Ventricular Remodeling," Circulation, 98(2):149-156, Lippincott Williams & Wilkins, United States (Jul. 1998).

Ono, K., et al., "The Humanized Anti-hm1.24 Antibody Effectively Kills Multiple Myeloma Cells by Human Effector Cell-mediated Cytotoxicity," Molecular Immunology, 36(6):387-395, Pergamon Press, England (Apr. 1999).

Originally Filed Claims of European Patent Application No. 13195713.6 (EP Publication No. EP2708558), submitted by the Opponent during EP opposition procedure for EP2708558 and posted by EPO on Jan. 15, 2019), 2 pages.

Originally Filed Description of EP Application No. 13195713.6 (EP Publication No. 2708558) (submitted by the Opponent during EP opposition procedure for EP 2708558 and posted by EPO on Jan. 15, 2019), 153 pages.

Osbourn, J.K., et al., "Generation of a Panel of Related Human scFv Antibodies With High Affinities for Human CEA," Immunotechnology, 2(3):181-96, Elsevier, Netherlands (Sep. 1996).

Ozaki, H., et al., "Effectiveness of Multimodality Treatment for Resectable Pancreatic Cancer," International Journal of Pancreatology 7:195-200, Humana Press, United States (1990).

Ozaki, H., et al., "The Prognostic Significance of Lymph Node Metastasis and Intrapancreatic Perineural Invasion in Pancreatic Cancer After Curative Resection," The Japanese Journal of Surgery 29:16-22, Springer, Japan (1999).

Ozhegov, et al., Tolkovyi Slovar Russkogo iazyka: 2004, p. 292.

Padlan, E.A., et al., "Structure of an Antibody-antigen Complex: Crystal Structure of the HyHEL-10 Fab-Lysozyme Complex," Proceedings of the National Academy of Sciences of the United States of America 86(15):5938-5942, National Academy of Sciences, United States (Aug. 1989).

Paez-Ribes, M., et al., "Antiangiogenic Therapy Elicits Malignant Progression of Tumors to Increased Local Invasion and Distant Metastasis," Cancer Cell, 15(3):220-231 (2009).

Pakula, A.A., et al., "Genetic Analysis of Protein Stability and Function," Annual Review of Genetics, 23:289-310, Annual Reviews, United States (1989).

Palladino et al., "Anti-TNF-Alpha Therapies: the Next Generation," Nature Reviews Drug Discovery, 2(9):736-746 (2003).

Pancook, J.D., et al., "In Vitro Affinity Maturation of Human IgM Antibodies Reactive with Tumor-Associated Antigens," Hybridoma and Hybridomics, 20(5-6):383-396, Mary Ann Liebert, United States (2001).

Pardridge, W.M., et al., "Enhanced Cellular Uptake and in Vivo Biodistribution of a Monoclonal Antibody Following Cationization," Journal of Pharmaceutical Sciences, 84(8):943-948, Elsevier, United States (Aug. 1995).

Pardridge, W.M., et al., "Enhanced Endocytosis in Cultured Human Breast Carcinoma Cells and in Vivo Biodistribution in Rats of a Humanized Monoclonal Antibody After Cationization of the Protein," The Journal of Pharmacology and Experimental Therapeutics, 286(1):548-554, American Society for Pharmacology and Experimental Therapeutics, United States (Jul. 1998).

Park, H., et al., "Interleukin-6 Protects MIN6 Beta Cells from Cytokin-Induced Apoptosis," Annals of the New York Academy of Sciences 1005:242-249, New York Academy of Sciences, United States (Nov. 2003).

Patel, et al., "A Forgotten Cause of Kidney Injury in Chronic Myelomonocytic Leukemia," Am J Kidney Dis, 54(1):159-64 (2009).

Patel, N.S., et al., "Endogenous Interleukin-6 Enhances the Renal Injury, Dysfunction, and Inflammation Caused by Ischemia/Reperfusion," The Journal of Pharmacology and Experimental Therapeutics 312(3):1170-1178, American Society for Pharmacology and Experimental Therapeutics, United States (Mar. 2005).

Patton, A., et al., "An Acid Dissociation Bridging Elisa for Detection of Antibodies Directed Against Therapeutic Proteins in the Presence of Antigen," Journal of Immunological Methods, 304(1-2):189-195, Elsevier, Netherlands (Sep. 2005).

Paul, W. E., "Fundamental Immunology," $5^{th}$ ed., 801-840 (2003).

Paul, W.E., "Transplantation and Graft Rejection," Fundamental Immunology 1124-1125, Third Edition, Raven Press, Ltd (1993).

Paule, B., "Reappraisal of the Concept of Hormone Therapy in Metastatic Prostate Cancer and Implications for Treatment," European Urology 47(6):729-735, Elsevier Science, Switzerland (Jun. 2005).

Pauleikhoff, "Neovascular Age-related Macular Degeneration," Retina, 25:1065-84 (2005).

Pavlinkova, G., et al., "Charge-modified Single Chain Antibody Constructs of Monoclonal Antibody CC49: Generation, Characterization, Pharmacokinetics, and Biodistribution Analysis," Nuclear Medicine and Biology, 26(1):27-34, Elsevier, United States (Jan. 1999).

Pavlou, A.K and Belsey, M.J, "The Therapeutic Antibodies Market to 2008," European Journal of Pharmaceutics and Biopharmaceutics, 59(3):389-396, Elsevier Science, Netherlands (Apr. 2005).

Pejchal, R., et al., "A Conformational Switch in Human Immunodeficiency Virus Gp41 Revealed by the Structures of Overlapping Epitopes Recognized by Neutralizing Antibodies," Journal of Virology, 83(17):8451-8462, American Society For Microbiology, United States (Sep. 2009).

Peters, M. C., "Plasma IL6 levels, metabolic dysfunction, and asthma severity: a cross-sectional analysis of two cohorts," Lancet Respir Med., 4(7):574-584 (2016).

Petkova, S.B., et al., "Enhanced Half-life of Genetically Engineered Human IgG1 Antibodies in a Humanized Fern Mouse Model: Potential Application in Humorally Mediated Autoimmune Disease," International Immunology 18(12):1759-1769, Oxford University Press, England (Dec. 2006).

Philippovich, "Fundamentals of Biochemistry," edition Higher school, Moscow 31 (1969).

Phillips, A.J., "The Challenge of Gene Therapy and DNA Delivery," The Journal of Pharmacy and Pharmacology 53(9):1169-1174, Pharmaceutical Society of Great Britain, England (Sep. 2001).

Pikarsky, E., et al., "NF-KB Functions as a Tumour Promoter in Inflammationassociated Cancer," Nature 431:461-466 (2004).

Pini, A., et al., "Design and Use of a Phage Display Library. Human Antibodies With Subnanomolar Affinity Against a Marker of Angiogenesis Eluted From a Two-dimensional Gel," The Journal of Biological Chemistry, 273(34):21769-21776, American Society for Biochemistry and Molecular Biology, United States (Aug. 1998).

Pirollo, K.F. and Chang, E.H., "Targeted Delivery of Small Interfering RNA: Approaching Effective Cancer Therapies," Cancer Research 68:1247-1250 (2008).

Poduslo, J.F., and Curran, G.L., "Polyamine Modification Increases the Permeability of Proteins at the Blood-nerve and Blood-brain Barriers," Journal of Neurochemistry, 66(4):1599-1609, Wiley on behalf of the International Society for Neurochemistry, England (Apr. 1996).

Pokrovsky, vol. 1 A—Infant, Soviet Encyclopedia, p. 146 (1991) (with English translation).

(56) References Cited

OTHER PUBLICATIONS

Poli, V., et al., "Interleukin-6 Deficient Mice Are Protected From Bone Loss Caused by Estrogen Depletion," The EMBO Journal, 13(5):1189-1196, Wiley Blackwell, England (Mar. 1994).
Polman, et al., "Diagnostic Criteria for Multiple Sclerosis: 2010 Revisions to the McDonald Criteria," Annals of Neurology, 69(2):292-302 (2011).
Pons, J., et al., "Energetic Analysis of an Antigen/antibody Interface: Alanine Scanning Mutagenesis and Double Mutant Cycles on the HyHEL-10/lysozyme Interaction," Protein Science: a Publication of the Protein Society, 8(5):958-968, Cold Spring Harbor Laboratory Press, United States (May 1999).
Porgador, A., et al., "Interleukin 6 Gene Transfection Into Lewis Lung Carcinoma Tumor Cells Suppresses the Malignant Phenotype and Confers Immunotherapeutic Competence Against Parental Metastatic Cells," Cancer Research 52:3679-3686 (1992).
Preliminary Amendment and Response to Restriction Requirement dated Mar. 20, 2013 in U.S. Appl. No. 13/257,145, filed Apr. 22, 2013 by Fish & Richardson P.C., 7 pages.
Presta, L.G., "Engineering of Therapeutic Antibodies to Minimize Immunogenicity and Optimize Function," Advanced Drug Delivery Reviews 58(5-6):640-656 (2006).
Presta, L.G., "Molecular Engineering and Design of Therapeutic Antibodies," Current Opinion in Immunology 20(4):460-470, Elsevier, England (Aug. 2008).
Sigma—H-Y Medium Product Information Sheet (1998) and document establishing that it was published in 1998, 4 pages (submitted by the Opponent during EP opposition procedure for EP2708558 and posted by EPO on Jan. 15, 2019).
Promega Protocols and Applications Guide, 1991, 2nd Edition (submitted by the Opponent during EP opposition procedure for EP2708558 and posted by EPO on Jan. 14, 2019), 3 pages.
Puhakka, M., et al., "Interleukin-6 and Tumor Necrosis Factor Alpha in Relation to Myocardial Infarct Size and Collagen Formation," Journal of Cardiac Failure, 9(4):325-332 (2003).
Q&A de wakaru himan to tounyoubyou, 3(6):982-984 (2004) (with English translation).
Quentmeier, H., et al., "Role of IL-6, IL-2, and IL-4 in the In Vitro Induction of Cytotoxic T Cells," Journal of Immunology 149(10):3316-3320, American Association of Immunologists, United States (Nov. 1992).
Rajpal, A., et al., "A General Method for Greatly Improving the Affinity of Antibodies by Using Combinatorial Libraries," Proceedings of the National Academy of Sciences of the United States of America 102(24):8466-8471 (2005).
Ramzy, D., et al., "Cardiac Allograft Vasculopathy: A Review," Canadian Journal of Surgery, 48(4):319-327 (2005).
Raposo, B., et al., "Epitope-Specific Antibody Response is Controlled by Immunoglobulin V(H) Polymorphisms," Journal of Experimental Medicine 211:405-411, Rockefeller University Press, United States (Mar. 2014).
Raso, "Intracellular Targeting Using Bispecific Antibodies," Methods in Molecular Medicine, vol. 25: Drug Targeting: Strategies, Principles, and Applications, 37-50 (2000).
Raso, V., et al., "Antibodies Capable of Releasing Diphtheria Toxin in Response to the Low pH Found in Endosomes," Journal of Biological Chemistry 272:27618-27622 (Oct. 1997).
Raso, V., et al., "Intracellular Targeting with Low pH-Triggered Bispecific Antibodies," The Journal of Biological Chemistry 272(44):27623-27628, American Society for Biochemistry and Molecular Biology, United States (Oct. 1997).
Rathanaswami, P., et al., "Demonstration of an in Vivo Generated Sub-picomolar Affinity Fully Human Monoclonal Antibody to Interleukin-8," Biochemical and Biophysical Research Communications, 334:1004-1013 (2005).
Reddy, M.P., et al., "Elimination of Fc Receptor-Dependent Effector Functions of a Modified IgG4 Monoclonal Antibody to Human CD4,"Journal of Immunology 164:1925-1933 (2000).
Reed, K. L., et al., "A neurokinin 1 receptor antagonist decreases postoperative peritoneal adhesion formation and increases peritoneal fibrinolytic activity," PNAS, 101(24):9115-9120 (2004).
Reichert, "Antibodies to watch in 2014," mAbs, 6(4): 799-802 (Jul./Aug. 2014).
Reichert, J.M., et al., "Development Trends for Monoclonal Antibody Cancer Therapeutics," Nature Reviews Drug Discovery 6(5):349-356, Nature Pub. Group, England (May 2007).
Reichert, J.M., et al., "Monoclonal Antibody Successes in the Clinic," Nature Biotechnology, 23(9):1073-1078, Nature America Publishing, United States (Sep. 2005).
Reimann, K.A., et al., "A Humanized Form of a CD4-specific Monoclonal Antibody Exhibits Decreased Antigenicity and Prolonged Plasma Half-life in Rhesus Monkeys While Retaining Its Unique Biological and Antiviral Properties," AIDS Research and Human Retroviruses, 13(11):933-943, Mary Ann Liebert, United States (1997).
Reist, C.J., et al., "Human IgG2 Constant Region Enhances in Vivo Stability of Anti-tenascin Antibody 81c6 Compared With Its Murine Parent," Clinical Cancer Research 4(10):2495-2502, The Association, United States (Oct. 1998).
Reply to Non-Final Office Action dated Feb. 14, 2013 filed Aug. 12, 2013, in U.S. Appl. No. 12/680,082, Igawa, T., et al., filed Jun. 25, 2010, 17 pages.
Reply to Restriction Requirement dated Jun. 1, 2012 for U.S. Appl. No. 12/996,162, Mitsunaga, S., et al., filed Jun. 28, 2012.
Reply to Office Action dated Aug. 29, 2011 for U.S. Appl. No. 12/524,041, Takahashi, M., et al., filed Jun. 20, 2012.
Reply to Final Office Action dated Apr. 9, 2012 in U.S. Appl. No. 12/161,733, Ishida, S., et al., filed Oct. 9, 2012, 13 pages.
Reply to Office Action dated Dec. 20, 2010 in U.S. Appl. No. 12/296,193, Nishimoto, N., et al., filed on Jun. 20, 2011.
Reply to Species Election Requirement dated Jun. 25, 2012 in U.S. Appl. No. 12/936,587, Igawa, T., et al., filed Jul. 25, 2012, 1 page.
Reply to Final Office Action dated Jun. 8, 2012 in U.S. Appl. No. 12/090,676, Kobara, M., et al., filed Jun. 29, 2012, 13 pages.
Reply to Restriction Requirement dated Mar. 21, 2013 in U.S. Appl. No. 13/524,528, Igawa, T., et al., filed Sep. 13, 2013, 1 page.
Reply to Office Action dated May 3, 2011 in U.S. Appl. No. 12/090,061, Yasunami, Y., et al., filed Nov. 1, 2011, 11 pages.
Reply to Restriction Requirement dated Oct. 7, 2011 in U.S. Appl. No. 12/680,112, Igawa, T., et al., filed Dec. 6, 2011, 15 pages.
Reply to Restriction Requirement dated Feb. 2, 2011 filed Jul. 25, 2011, in U.S. Appl. No. 12/094,644, Nakashima, J., et al., filed Feb. 27, 2009, 2 pages.
Reply to Restriction Requirement dated Jan. 13, 2011 filed Jul. 7, 2011, in U.S. Appl. No. 12/161,733, Ishida, S., et al., filed Mar. 9, 2009, 1 page.
Reply to Restriction Requirement dated Jan. 31, 2013 filed Mar. 1, 2013, in U.S. Appl. No. 13/387,292, Maeda, S., et al., filed Apr. 3, 2012, 2 pages.
Reply to Office Action dated Jun. 28, 2011 filed Dec. 27, 2011, in U.S. Appl. No. 12/295,039, Igawa, T., et al., filed Jan. 20, 2009, 14 pages.
Reply to Restriction Requirement dated Mar. 20, 2013 filed Apr. 22, 2013, in U.S. Appl. No. 13/257,145, Igawa, T., et al., filed Nov. 22, 2011, 7 pages.
Reply to Office Action dated Nov. 26, 2010 filed May 25, 2011, in U.S. Appl. No. 12/085,065, Okada, M., et al., filed Jun. 1, 2009, 9 pages.
Reply to Restriction Requirement dated Oct. 5, 2010 filed Nov. 2, 2010, in U.S. Appl. No. 12/296,193, Nishimoto, N., et al., filed Apr. 15, 2009, 2 pages.
Reply to Restriction Requirement dated Sep. 14, 2012 filed Nov. 8, 2012, in U.S. Appl. No. 12/680,082, Igawa, T., et al., filed Jun. 25, 2010, 14 pages.
Reply to Office Action dated Sep. 26, 2011 filed Mar. 21, 2012, in U.S. Appl. No. 12/094,644, Nakashima, J., et al., filed Feb. 27, 2009, 9 pages.
Reply to Reconsideration-After Non-Final Reject Office Action dated Mar. 15, 2013 filed Sep. 13, 2013, in U.S. Appl. No. 12/524,041, Takahashi, M., et al., filed Sep. 18, 2009, 6 pages.

(56) References Cited

OTHER PUBLICATIONS

Request for Continued Examination and Information Disclosure Statement dated Sep. 12, 2011, in U.S. Appl. No. 12/085,065, Okada, M., et al., filed Jun. 1, 2009, 1 page.
Response to Restriction Requirement dated Apr. 11, 2011 in U.S. Appl. No. 12/295,039, Igawa, T. et al., filed Jan. 20, 2009, 9 pages.
Response to Restriction Requirement dated Aug. 27, 2010 in U.S. Appl. No. 12/090,061, Fish & Richardson P.C., et al., filed Feb. 24, 2011, 1 page.
Response to Restriction Requirement dated Oct. 2, 2012 in U.S. Appl. No. 12/679,922, Fish & Richardson P.C., et al., filed Nov. 1, 2012, 2 pages.
Response to Restriction Requirement dated Oct. 22, 2010 in U.S. Appl. No. 12/085,065, Okada, M., et al., filed Jun. 1, 2009, 2 pages.
Response to Restriction Requirement filed Aug. 31, 2010, in U.S. Appl. No. 12/090,676, Kobara, M., et al., filed Oct. 20, 2006, U.S. Patent and Trademark Office.
Response to Restriction Requirement for U.S. Appl. No. 12/524,041, filed Oct. 28, 2011, 2 pages.
Restriction Requirement dated Oct. 12, 2010 for U.S. Appl. No. 12/295,039, Igawa, T., et al., filed Jan. 20, 2009.
Restriction Requirement dated Jan. 13, 2011 for U.S. Appl. No. 12/161,733, Ishida, S., et al., filed Mar. 9, 2009.
Restriction Requirement dated Oct. 2, 2012 for U.S. Appl. No. 12/679,922, Igawa, T., et al., filed Oct. 1, 2010.
Restriction Requirement dated Dec. 31, 2014 for U.S. Appl. No. 13/637,415, Igawa, T., et al., filed Feb. 4, 2013.
Restriction Requirement dated Dec. 6, 2011 for U.S. Appl. No. 12/936,587, Igawa, T., et al., filed Jan. 3, 2011.
Restriction Requirement dated Oct. 7, 2011 for U.S. Appl. No. 12/680,112, Tomoyuki Igawa et al., filed Jun. 23, 2010.
Restriction Requirement dated Aug. 27, 2010, in U.S. Appl. No. 12/090,061, Yasunami, Y., et al., filed Mar. 6, 2009.
Restriction Requirement dated Aug. 29, 2011 in U.S. Appl. No. 12/524,041, Takahashi, M., et al., filed Sep. 18, 2009.
Restriction Requirement dated Aug. 31, 2017, in U.S. Appl. No. 15/263,617, Igawa, T., et al., filed Sep. 13, 2016.
Restriction Requirement dated Dec. 1, 2016, in U.S. Appl. No. 13/637,415, Igawa, T., et al., filed Feb. 4, 2013.
Restriction Requirement dated Jan. 31, 2013, in U.S. Appl. No. 13/387,292, Maeda, S., et al., filed Apr. 3, 2012.
Restriction Requirement dated Jun. 25, 2012 in U.S. Appl. No. 12/936,587, Igawa, T., et al., filed Jan. 3, 2011, 5 pages.
Restriction Requirement dated Jun. 6, 2012, in U.S. Appl. No. 12/680,082, Igawa, T., et al., filed Jun. 25, 2010, 12 pages.
Restriction Requirement dated Mar. 12, 2010 in U.S. Appl. No. 12/090,676, Kobara, M., filed Feb. 25, 2009, 4 pages.
Restriction Requirement dated Mar. 20, 2013, in U.S. Appl. No. 13/257,145, Igawa, T., et al., filed Nov. 22, 2011, 11 pages.
Restriction Requirement dated Mar. 21, 2013, in U.S. Appl. No. 13/524,528, Igawa, T., et al., filed Jun. 15, 2012, 7 pages.
Restriction Requirement dated Oct. 5, 2010 in U.S. Appl. No. 12/296,193, Nishimoto, N., et al., filed Apr. 15, 2009, 6 pages.
Restriction Requirement dated Sep. 14, 2012, in U.S. Appl. No. 12/680,082, Igawa, T., et al., filed Jun. 25, 2010, 6 pages.
Restriction Requirement dated Sep. 19, 2012 in U.S. Appl. No. 12/680,112, Igawa, T., et al., filed Jun. 23, 2010, 6 pages.
Restriction Requirement dated Apr. 30, 2010, in U.S. Appl. No. 12/085,065, Okada, et al., filed Jun. 1, 2009.
Results of the phase III international joint clinical trial of Satralizumab on Neuromyelitis Optica Spectrum Disorder at the European Committee for Treatment and Research in Multiple Sclerosis (ECTRIMS) 2018.
Reverberi, R., et al., "Factors Affecting the Antigen-Antibody reaction," Blood Transfusion 5:227-240, SIMTI servizi, Italy (Nov. 2007).
Revez, J. N. M. A., "The Role of the Interleukin-6 Pathway in Asthma," Thesis submitted for degree of Doctor of Philosophy, Univ. of Queensland, 78-115 (2018).

Rich, R.L. and Myszka D.G., "Grading the Commercial Optical Biosensor Literature—Class of 2008: 'The Mighty Binders'," Journal of Molecular Recognition 23(1):1 -64, John Wiley & Sons, England (Jan./Feb. 2010).
Rituximab biologic license application approval, dated Nov. 26, 1997 (submitted by the Opponent during EP opposition procedure for EP2708558 and posted by EPO on Jan. 15, 2019), 2 pages.
Rituximab product information, IDEC Pharmaceuticals Corporation, Nov. 1997, (submitted by the Opponent during EP opposition procedure for EP2708558 and posted by EPO on Jan. 15, 2019, 2 pages Japanese Patent office, Tokyo mailed on Jan. 15, 2019, 2 pages.
Rituximab, Wikipedia (https://de.wikipedia.org/wiki /Rituximab), accessed on Oct. 24, 2018, (submitted by the Opponent during EP opposition procedure for EP 2708558 and posted by EPO on Jan. 15, 2019), 7 pages (with English translation).
Roitt, A., et al., Extract from Chapter 6, Immunology (2000), Moscow, "Mir", pp. 110-111 and English translation of section bridging pp. 110-111.
Rojas, J.R., et al., "Formation, Distribution, and Elimination of Infliximab and Anti-Infliximab Immune Complexes in Cynomolgus Monkeys," The Journal of Pharmacology and Experimental Therapeutics 313(2):578-585, American Society for Pharmacology and Experimental Therapeutics, United States (May 2005).
Roopenian, et al., "FcRn: The Neonatal Fc Receptor Comes of Age," Nature Reviews Immunology, 7(9):715-25 (2007).
Rothe, A., et al., "Ribosome Display for Improved Biotherapeutic Molecules," Expert Opinion on Biological Therapy, 6(2):177-187 (2006).
Rudikoff, S., et al., "Single Amino Acid Substitution Altering Antigen-binding Specificity," Proceedings of the National Academy of Sciences of the United States of America 79(6):1979-1983 (1982).
Ryman, J.T., and Meibohm, B., "Pharmacokinetics of Monoclonal Antibodies," CPT: Pharmacometrics & Systems Pharmacology, 6(9):576-588, Wiley, United States (Sep. 2017).
Saba, A. A., et al., "Effects of Interleukin-6 and its Neutralizing Antibodies on Peritoneal Adhesion Formation and Wound Healing," Am Surg., 62(7):569-572 (1996).
Sacchi, et al., "Treatment With Monoclonal Antibody to a Lewis Lung Carcinoma-Associated Antigen: Different Effects on Primary Tumor and its Metastases," Cancer Treatment Reviews, 69:985-991 (1985).
Sack, U., et al., "Interleukin-6 in Synovial Fluid is Closely Associated With Chronic Synovitis in Rheumatoid Arthritis," Rheumatology International, 13(2):45-51 (1993).
Sada, E., et al., "Effect of Histidine Residues in Antigenic Sites on pH Dependence of Immune-Adsorption Equilibrium," Applied Microbiology and Biotechnology 27:528-532, Springer (Feb. 1988).
"Chugai NMO Clinical Trial Webinar," Sakura Star Study, Dec. 12, 2014, accessed at https://s3.amazonaws.com/gjcf-wp-uploads/wp-content/uploads/2016/05/16162202/12_12_14_Chugai_Webinar_PPT_Complete_Deck_FINAL.pdf, accessed on Sep. 5, 2019, 18 pages.
Salfeld, J. G., "Isotype Selection in Antibody Engineering," Nature Biotechnology, 25(12):1369-1372 (2007).
Salgado, R., et al., "Circulating Interleukin-6 Predicts Survival in Patients with Metastatic Breast Cancer," International Journal of Cancer 103(5):642-646 (2003).
Sal-Man, N and Shai, Y., "Arginine Mutations Within a Transmembrane Domain of Tar, an *Escherichia coli* Aspartate Receptor, Can Drive Homodimer Dissociation and Heterodimer Association in Vivo," The Biochemical Journal, 385(1):29-36, Published by Portland Press on behalf of the Biochemical Society, England (Jan. 2005).
Sanayama, Y., et al., "Prediction of Therapeutic Responses to Tocilizumab in Patients With Rheumatoid Arthritis," Arthritis Rheumatol., 66(6):1421-1431 (2014).
Sansone, et al., "IL-6 Triggers Malignant Features in Mammospheres From Human Ductal Breast Carcinoma and Normal Mammary Gland," Journal of Clinical Investigation, 117(12):3988-4002 (2007).

(56) References Cited

OTHER PUBLICATIONS

Sarkar, C.A., et al., "Rational Cytokine Design for Increased Lifetime and Enhanced Potency Using Ph-activated "Histidine Switching"," Nature Biotechnology, 20(9):908-913, Nature America Publishing (Sep. 2002).

Sarkar, F. H., et al., "Back to the Future: COX-2 Inhibitors for Chemoprevention and Cancer Therapy," Mini-Reviews in Medicinal Chemistry, 7(6):599-608 (2007).

Sato, K., et al., "Reshaping a Human Antibody to Inhibit the Interleukin 6-dependent Tumor Cell Growth," Cancer Research, 53(4):851-856, American Association for Cancer Research, United States (Feb. 15, 1993).

Schaeffer, R.C et al., "The Rat Glomerular Filtration Barrier Does Not Show Negative Charge Selectivity," Microcirculation, 9(5):329-342 (2002).

Schier, et al., "Isolation of Picomolar Affinity Anti-c-erbB-2 Single-chain Fv by Molecular Evolution of the Complementarity Determining Regions in the Center of the Antibody Binding Site," Journal of Molecular Biology 263:551-567, Elsevier, England (Nov. 1996).

Schmitz, U., et al., "Phage Display: a Molecular Tool for the Generation of Antibodies—a Review," Placenta, 21:106-112, Elsevier, Netherlands (Mar.-Apr. 2000).

Schroeder, H.W., Jr., "Similarity and Divergence in the Development and Expression of the Mouse and Human Antibody Repertoires," Developmental and Comparative Immunology 30(1-2):119-135, Elsevier Science, United States (Jan. 2006).

Schroter, C., et al., "A Generic Approach to Engineer Antibody Ph-switches Using Combinatorial Histidine Scanning Libraries and Yeast Display," mAbs 7(1):138-151, Taylor & Francis, United States (Jan.-Feb. 2015).

Schultz, E., "Satellite Cell Proliferative Compartments in Growing Skeletal Muscles," Developmental Biology 175:84-94 (1996).

Schultz, E., et al., "Acute Effects of Hindlimb Unweighting on Satellite Cells of Growing Skeletal Muscle," Journal of Applied Physiology, 76(1):266-70 (1994).

Schultz et al., "Response of Satellite Cells to Focal Skeletal Muscle Injury," Muscle Nerve, 8:217- 222 (1985).

Sebba, A., "Tocilizumab: The First Interleukin-6-Receptor Inhibitor," American Journal of Health-System Pharmacy 65(15):1413-1418 (2008).

Seddon, et al., "Progression of Age-related Macular Degeneration," Arch. Ophthalmol., 123:774-782 (2005).

Segal, D. M., et al., "Bispecific Antibodies in Cancer Therapy," Current Opinion in Immunology, 11:558-562, (1999).

Sequence alignments and modification scheme (Document filed during Oral Proceedings in EPO opposition for EP2006381 and mentioned in minutes of the Oral Proceedings) posted by EPO on Jul. 25, 2018, 3 pages.

Serada, S., et al., "IL-6 Blockade Inhibits the Induction of Myelin Antigen-Specific Th17 Cells and Th1 Cells in Experimental Autoimmune Encephalomyelitis," Proceedings of the National Academy of Sciences 105:9041-9046 (2008).

Shadduck, R.K., et al., "Fractionation of Antibodies to L-cell Colony-Stimulating Factor by Affinity Chromatography," Blood 53(6):1182-1190, American Society of Hematology, United States (Jun. 1979).

Sharifi, J., et al., "Improving Monoclonal Antibody Pharmacokinetics via Chemical Modification," The Quarterly Journal of Nuclear Medicine: Official Publication of the Italian Association of Nuclear Medicine (AIMN) [and] the International Association of Radiopharmacology (IAR), 42(4):242-249, Minerva Medica, c1995-c2003, Italy (Dec. 1998).

Shaul, Y. and Schreiber, G., "Exploring the Charge Space of Protein-protein Association: a Proteomic Study," Proteins, 60(3):341-352, Wiley-Liss, United States (Aug. 2005).

Shewach and Lawrence, "Gemcitabine and Radiosensitization in Human Tumor Cells," Investigational New Drugs 14:257-263 (1996).

Shields, R. L., et al., "High Resolution Mapping of the Binding Site on Human IgG1 for Fc Gamma RI, Fc Gamma RIII, Fc Gamma RIH, and FcRn and Design of Igg1 Variants With Improved Binding to the Fc Gamma R," The Journal of Biological Chemistry, 276(9):6591-6604, American Society for Biochemistry and Molecular Biology, United States (Mar. 2001).

Shima, Y., et al., "Tocilizumab, a Humanized Anti-Interleukin-6 Receptor Antibody, Ameliorated Clinical Symptoms and MRI Findings of a Patient with Ankylosing Spondylitis," Modern Rheumatology, 21(4):436-439 (2011).

Shimazaki, et al., "Hito Kotsuzuishu Model to Ko hito IL-6 Juyotai Kotai No. Ko Shuyo Koka," Rinsho Ketsueki 38:281-284, (1997) (English translation provided).

Shimizu, et al., "IFN-1b May Severely Exacerbate Japanese Optic-spinal Ms in Neuromyelitis Optica Spectrum," Neurology, 75(16):1423-1427 (2010).

Shimizu, H., et al., "KRP-203, a Novel Synthetic Immunosuppressant, Prolongs Graft Survival and Attenuates Chronic Rejection in Rat Skin and Heart Allografts," Circulation, 111(2):222-22 (2005).

Shimizu, H., et al., "Successful Treatment with Tocilizumab for Refractory Scleritis Associated with Relapsing Polychondritis," Scandinavian Journal of Rheumatology 46:418-419 (2017).

Shimizu, K. and Oku, N., "Cancer Anti-Angiogenic Therapy," Biological and Pharmaceutical Bulletin 27(5):599-605 (2004).

Shinriki, S., et al., "Humanized Anti-Interleukin-6 Receptor Antibody Suppresses Tumor Angiogenesis and In vivo Growth of Human Oral Squamous Cell Carcinoma," Clin Cancer Res., 15(17):5426-5434 (2009).

Shire, S.J., et al., "Challenges in the Development of High Protein Concentration Formulations," Journal of Pharmaceutical Sciences 93(6):1390-1402 (2004).

Sideleva, O., et al., "Obesity and Asthma: An Inflammatory Disease of Adipose Tissue Not the Airway," Am J Respir Crit Care Med., 186(7):598-605 (2012).

Sigma-Aldrich, "Product Information: Monoclonal Anti-Flag® M1, Clone M1 Produced in Mouse, Purified Immunoglobulin," Sigma-Aldrich.com, Catalog No. F3040 (2008) [Retrieved on Nov. 5, 2013] Retrieved from the Internet [URL: http://www.sigmaaldrich.com/content/dam/sigmaaldrich/ does/Sigma/Datasheet/f3040dat.pdf].

Silpa-Archa et al., "Outcome of Tocilizumab Treatment in Refractory Ocular Inflammatory Diseases," Acta Ophthalmol., 94:e400-e406 (2016).

Singer et al., Genes & Genomes, 67-69 (1991).

Skolnick, J and Fetrow, J.S., "From Genes to Protein Structure and Function: Novel Applications of Computational Approaches in the Genomic Era," Trends in Biotechnology, 18(1):34-39 (2000).

Skurkovich, S.V., et al., "Anticytokine Therapy—New Approach to the Treatment of Autoimmune and Cytokine-Disturbance Diseases," Oncology and Immunopathology 2:71-80 (2003) (Partial English translation).

Skurkovich, S. V., et al., "Anticytokine Therapy—New Approach to the Treatment of Autoimmune and Cytokine-Disturbance Diseases," Medical Hypotheses 59:770-780 (2002). (in Russian; relevant portions in English).

Sleeman, J. and Steeg, P. S., "Cancer metastasis as a therapeutic target," Eur J Cancer., 46(7):1177-1180 (2010).

Smith, et al., "Anti-Interleukin-6 Monoclonal Antibody Induces Regression of Human Prostate Cancer Xenografts in Nude Mice," Prostate, 48:47-53 (2001).

Smith, T.F., et al., "The Challenges of Genome Sequence Annotation or "the Devil is in the Details"," Nature Biotechnology 15(12):1222-1223 (1997).

Smolen, J.S., et al., "Interleukin-6: a New Therapeutic Target," Arthritis Research & therapy, 8 Suppl 2:S5, BioMed Central, England (Jul. 2006).

Snow, M.H., "Satellite Cell Response in Rat Soleus Muscle Undergoing Hypertrophy Due to Surgical Ablation of Synergists," The Anatomical Record 227(4):437-446 (1990).

Snow, M. H., "Myogenic Cell Formation in Regenerating Rat Skeletal Muscle Injured by Mincing. II. An Autoradiographic Study," The Anatomical Record 188:201-217 (1977).

Sparano, A., et al., "Modulation of Th1 and Th2 cytokine profiles and their association with advanced head and neck squamous cell carcinoma," Otolaryngol Head Neck Surg., 131(5):573-576 (2004).

(56) References Cited

OTHER PUBLICATIONS

Spiess, C., et al., "Bispecific Antibodies With Natural Architecture Produced by Co-culture of Bacteria Expressing Two Distinct Half-antibodies," Nature biotechnology, 31(8):753-758, Nature America Publishing, United States (Aug. 2013).
Srivastava, et al., "Potassium Channel KIR4.1 as an Immune Target in Multiple Sclerosis," The New England Journal of Medicine, 367:115-123 (2012).
Stan, A.C., et al., "In Vivo Inhibition of Angiogenesis and Growth of the Human U-87 Malignant Glial Tumor by Treatment With an Antibody Against Basic Fibroblast Growth Factor," Journal of Neurosurgery, 82(6):1044-1052 (1995).
Stearns, D.J., et al., "The Interaction of a Ca2+-Dependent Monoclonal Antibody with the Protein C Activation Peptide Region. Evidence for Obligatory Ca2+ Binding to Both Antigen and Antibody," Journal of Biological Chemistry 263:826-832, American Society for Biochemistry and Molecular Biology, United States (Jan. 1988).
Steeg, P. S. and Theodorescu, D., "Metastasis: a Therapeutic Target for Cancer," Nature Clinical Practice Oncology 5(4):206-219 (2008).
Steeg, P. S., "Tumor Metastasis: Mechanistic Insights and Clinical Challenges," Nature Medicine 12(8):895-904 (2006).
Stewart, J.D., et al., "Site-directed Mutagenesis of a Catalytic Antibody: an Arginine and a Histidine Residue Play Key Roles," Biochemistry 33:1994-2003, American Chemical Society, United States (Mar. 1994).
Strand, V., et al., "Biologic Therapies in Rheumatology: Lessons Learned, Future Directions," Nature Reviews Drug Discovery 6(1):75-92 (2007).
Strassmann, G., et al., "Evidence for the Involvement of Interleukin 6 in Experimental Cancer Cachexia," The Journal of Clinical Investigation 89(5):1681-1684 (1992).
Studebaker, et al., "Fibroblasts Isolated From Common Sites of Breast Cancer Metastasis Enhance Cancer Cell Growth Rates and Invasiveness in an Interleukin-6-dependent Manner," Cancer Research, 68(21):9087-9095 (2008).
Sugahara, H., er al., "Expression of Interleukin-6 in Human Intrahepatic Biliary Tract and its Pathologic Significance; An Inununohistochemical and In situ Hybridization Study," Juzen Medical Society 105:819-833 (1996).
Summary of information about antibodies in Examples of patent EP2006381 (document submitted in EP opposition and posted by EPO on Apr. 13, 2018).
Sun, W., et al., "Coexpression of Gas6/axl in Human Ovarian Cancers," Oncology, 66(6):450-457, Basel, Switzerland (Jan. 2004).
Supplemental Amendment and Response in U.S. Appl. No. 12/296,193, Nishimoto, et al., filed Mar. 19, 2012.
Supplementary European Search Report for EP Application No. EP06811729, The Hague, Netherlands, dated Nov. 17, 2009, 5 pages.
Supplementary European Search Report for EP Application No. EP07707458, The Hague, Netherlands, dated Nov. 30, 2009, 5 pages.
Suzuki, M., et al., "Anti-inflammatory mechanism of tocilizumab, a humanized anti-IL-6R antibody: effect on the expression of chemokine and adhesion molecule," Rheumatol Int., 30:309-315 (2010).
Suzuki, et al., "Gemcitabine Selectively Eliminates Splenic Gr-1 +/CDIIb+ Myeloid Suppressor Cells in Tumor-Bearing Animals and Enhances Antitumor Immune Activity," Clinical Cancer Research, 11:6713-6721 (2005).
Suzuki, H., et al., "Anti-Murine IL-6 Receptor Antibody Inhibits IL-6 Effects in Vivo," Immunology Letters 30(1):17-21 (1991).
Tabrizi, M.A., et al., "Elimination Mechanisms of Therapeutic Monoclonal Antibodies," Drug Discovery Today, 11(1-2):81-88, Distributed by Virgin Mailing and Distribution, c1996-, England (Jan. 2006).
Taga, T., et al., "Interleukin-6 Triggers the Association of Its Receptor With a Possible Signal Transducer, gp130," Cell, 58(3):573-581 (1989).
Taga, T., et al., "Receptors for B Cell Stimulatory Factor 2" The Journal of Experimental Medicine 166:967-981 (1987).
Takahashi, H., et al., "Antiproteases in Preventing the Invasive Potential of Pancreatic Cancer Cells," Journal of the Pancreas 8(4 Suppl):501-508 (2007).
Takeda, K., et al., "Murine Tumor Cells Metastasizing Selectively in the Liver: Ability to Produce Hepatocyte-Activating Cytokines Interleukin-1 and/or -6," Japanese Journal of Cancer Research 82:1299-1308 (1991).
Takeshita, Y., et al., "The effect of NMO-IgG and anti-IL-6 receptor monoclonal antibody(SA237) for the Blood-Brain Barrier," $60^{th}$ Annual Meeting of the Japanese Society of Neurology, General Subject, Adoption result, Presentation No. 0-08-6, Feb. 18, 2019 [retrieval date Apr. 20, 2020] (see Takeshita 59(S224):0-08-6 2019 for English abstract).
Takeshita, Y., et al., "The effect of NMO-IgG and anti-IL-6 receptor monoclonal antibody(SA237) for the Blood-Brain Barrier," Rinsho Shinkeigaku, 59(S224):0-08-6 (2019), English abstract of Takeshita 2019 (retrieval date Apr. 20, 2020).
Takeshita, Y., et al., "Effects of neuromyelitis optica-IgG at the blood-brain barrier in vitro," Neurol Neuroimmunol Neuroinflamm., 4:e311 (2016).
Takkinen, K., et al., "Affinity and Specificity Maturation by CDR Walking," Antibody Engineering, 38:540-545 (2001).
Tamura, T., et al., "Soluble Interleukin-6 Receptor Triggers Osteoclast Formation by Interleukin 6," Proceedings of the National Academy of Sciences USA 90:11924-11928 (1993).
Tan, P.H., et al., "Engineering the Isoelectric Point of a Renal Cell Carcinoma Targeting Antibody Greatly Enhances ScFv Solubility," Immunotechnology : an International Journal of Immunological Engineering, 4(2):107-114 (1998).
Tanaka, F., et al., "The Anti-Human Tumor Effect and Generation of Human Cytotoxic T Cells in SCID Mice Given Human Peripheral Blood Lymphocytes by the in Vivo Transfer of the lnterleukin-6 Gene Using Adenovirus Vector," Cancer Research 57(7):1335-1343 (1997).
Tantraworasin, A., et al., "Prognostic Factors of Tumor Recurrence in Completely Resected Non-Small Cell Lung Cancer," Cancer Management and Research, 5:77-84 (2013).
Tarditi, L., et al., "Selective High-performance Liquid Chromatographic Purification of Bispecific Monoclonal Antibodies," Journal of Chromatography, 599(1-2):13-20, Elsevier, Netherlands (May 1992).
Teeling, J.L., et al., "The Biological Activity of Human CD20 Monoclonal Antibodies is Linked to Unique Epitopes on CD20," Journal of Immunology 177(1):362-371 (2006).
Ten Kate, C.I., et al., "Effect of Isoelectric Point on Biodistribution and Inflammation: Imaging With Indium-111-labelled IgG," European Journal of Nuclear Medicine, 17(6-8):305-309, Springer Verlag, Germany (1990).
Thies, M.J., et al., "The Alternatively Folded State of the Antibody C(H)3 Domain," Journal of Molecular biology 309(5):1077-1085, Academic Press, England (Jun. 2001).
Third Preliminary Amendment and Response to Restriction Requirement dated Jun. 5, 2012 in U.S. Appl. No. 12/936,587, Igawa, T., et al., filed Jan. 3, 2011, 7 pages.
Tintore, M., et al., "Isolated Demyelinating Syndromes: Comparison of Different MR Imaging Criteria to Predict Conversion to Clinically Definite Multiple Sclerosis," AJNR American Journal of Neuroradiology 21:702-706 (2000).
Tisdale, M.J., "Biology of Cachexia," Journal of the National Cancer Institute 89(23):1763-1773 (1997).
Tobe, et al., "Targeted Disruption of the FGF2 Gene does not Prevent Choroidal Neovascularization in the Murine Model," The American Journal of Pathology, 153:1641-1646 (1998).
Trikha, M., et al., "Targeted Anti-Interleukin-6 Monoclonal Antibody Therapy for Cancer: A Review of the Rationale and Clinical Evidence," Clinical Cancer Research, 9(13):4653-4665, (2003).
Tsubaki, M., et al., "C-terminal Modification of Monoclonal Antibody Drugs: Amidated Species as a General Product-related Substance," International Journal of Biological MacroMolecules 52:139-147, IPC Science and Technology Press, Netherlands (Jan. 2013).

(56) References Cited

OTHER PUBLICATIONS

Tsuchiya, M., "Therapeutic Antibody," Credit Suisse Seminar at Fuji-Gotemba Research Laboratories, p. 21, Shizuoka, Japan (2006) (with English translation).
Tsujinaka, T., et al., "Interleukin 6 Receptor Antibody Inhibits Muscle Atrophy and Modulates Proteolytic Systems in Interleukin 6 Transgenic Mice," The Journal of Clinical Investigation 97(1):244-249 (1996).
Tsurushita, N., et al., "Design of Humanized Antibodies: From Anti-tac to Zenapax," Methods (San Diego, Calif.), 36(1):69-83, Academic Press, United States (May 2005).
Uchida, T., et al., "Increased cerebrospinal fluid metalloproteinase-2 and interleukin-6 are associated with albumin quotient in neuromyelitis optica: Their possible role on blood-brain barrier disruption," Mult Scler J., 23(8):1072-1084 (2017).
Ulich, et al., "Intratracheal Injection of Endotoxin and Cytokines, Ii. Lnterleukin-6 and Transforming Growth Factor Bela Inhibit Acute Inftammation," The American Journal of Pathology, 138(5):1097-1101 (1991).
Unverified English language translation of French Patent FR2694767A1, published Feb. 18, 1994, 12 pages.
Unverified English language translation of TW201021839A1, published Jun. 16, 2010, in the name of Chugai Seiyaku Kabushiki Kaisha.
U.S. National Library of Medicine (NIH) publication (online), MedlinePlus Medical Encyclopedia, "Liver metastases," Accessed Nov. 22, 2014.
Vaccaro, C., et al., "Divergent Activities of an Engineered Antibody in Murine and Human Systems Have Implications for Therapeutic Antibodies," Proceedings of the National Academy of Sciences of the United States of America 103(49):18709-18714, National Academy of Sciences, United States (Dec. 2006).
Vaisitti, T., et al., "Cationization of Monoclonal Antibodies: Another Step Towards the "Magic Bullet"," Journal of Biological Regulators and Homeostatic Agents, 19(3-4):105-112 (2005).
Vajdos, F.F., et al., "Comprehensive Functional Maps of the Antigen-binding Site of an Anti-ErbB2 Antibody Obtained With Shotgun Scanning Mutagenesis," Journal of Molecular Biology, 320(2)1:415-428 (2002).
Valantine, "Cardiac Allograft Vasculopathy After Heart Transplantation: Risk Factors and Management," The Journal of Heart and Lung Transplantation, 23:S187-S193 (2004).
Van Den Abbeele, A.D., et al., "Antigen-binding Site Protection During Radiolabeling Leads to a Higher Immunoreactive Fraction," Journal of Nuclear Medicine, 32(1 ):116-122 (1991).
Van Der Meulen, J., et al., "The H3K27me3 Demethylase UTX in Normal Development and Disease," Epigenetics 9(5):658-668 (2014).
Van Haaften, G., et al., "Somatic Mutations of the Histone H3K27 Demethylase Gene UTX in Human Cancer," Nature Genetics 41(5):521-523 (2009).
Van Walle, I., et al., "Immunogenicity Screening in Protein Drug Development," Expert Opinion on Biological Therapy, 7(3):405-418 (2007).
Vaughn, D.E., et al., "Structural Basis of pH-Dependent Antibody Binding by the Neonatal Fc Receptor", Structure 6:63-73, Cell Press, United States (Jan. 1998).
Venturi, M., et al., "The Monoclonal Antibody 1f6 Identifies a pH-dependent Conformational Change in the Hydrophilic NH(2) terminus of NhaA Na(+)/H(+) Antiporter of *Escherichia coli*," The Journal of Biological Chemistry 275(7):4734-4742, American Society for Biochemistry and Molecular Biology, United States (Feb. 2000).
Verhoeyen, et al., "Monoclonal Antibodies in Clinical Oncology," Edited by AA Epenetos, Chapter 5:37-43, Chapman and Hall (1991).
Verhoeyen, M.E., et al., "Construction of a Reshaped HMFG1 Antibody and Comparison of Its Fine Specificity With That of the Parent Mouse Antibody," Immunology, 78(3):364-370, Blackwell Scientific Publications, England (Mar. 1993).

Vidal, et al., "Making Sense of Antisense," European Journal of Cancer, 41:2812-2818 (2005).
Vincent, J., et al., "5-fluorouracil Selectively Kills Tumor-associated Myeloid-derived Suppressor Cells Resulting in Enhanced T Cell-dependent Antitumor Immunity," Cancer Research, 70(8):3052-3061 (2010).
Wally, J., et al., "Identification of a Novel Substitution in the Constant Region of a Gene Coding for an Amyloidogenic Kappal Light Chain," Biochimica et Biophysica Acta 1454(1):49-56, Elsevier Pub. Co., Netherlands (May 1999).
Wang, et al., "Antibody Structure, Instability, and Formulation," Journal of Pharmaceutical Sciences, 96(1): 1-26 (2007).
Wang, H., et al., "Phase II Study of Panobinostat and Bortezomib in Patients with Pancreatic Cancer Progressing on Gemcitabine-Based Therapy," Anticancer Research 32:1027-1032, International Institute of Anticancer Research, Greece (Mar. 2012).
Wang, Q.C., et al., "Polyethylene Glycol-modified Chimeric Toxin Composed of Transforming Growth Factor Alpha and Pseudomonas Exotoxin," Cancer Research 53(19):4588-4594, American Association for Cancer Research, Chicago (Oct. 1993).
Wang, W., "Instability, Stabilization, and Formulation of Liquid Protein Pharmaceuticals," International Journal of Pharmaceutics 185(2):129-188, Elsevier/North-Holland Biomedical Press, Netherlands (Aug. 1999).
Wang, X.D., et al., "Mechanical Load-dependent Regulation of Satellite Cell and Fiber Size in Rat Soleus Muscle," American Journal of Physiology, 290(4):C981-C989 (2006).
Wang, J., et al., "IL-6 pathway-driven investigation of response to IL-6 receptor inhibition in rheumatoid arthritis," BMJ Open, 3:e003199 (2013).
Wang, J., et al., "Endogenous and Exogenous IL-6 Inhibit Aeroallergen-lnduced Th2 Inflammation," J Immunol., 165:4051-4061 (2000).
Wang, L. and Shilatifard, A., "UTX Mutations in Human Cancer," Cancer Cell 35(2):168-176 (2019).
Ward et al., "A Calcium-binding Monoclonal Antibody That Recognizes a Non-calcium-binding Epitope in the Short Consensus Repeat Units (Sers) of Complement C1r," Molecular Immunology, 29(1):83-93, (Jan. 1992).
Warren, G.L., et al., "Physiological Role of Tumor Necrosis Factor Alpha in Traumatic Muscle Injury," FASEB Journal, 16(12):1630-1632 (2002).
Waubant, et al., "Clinical Characteristics of Responders to Interferon Therapy for Relapsing MS," Neurology 61:184-189 (2003).
Webber, et al., "Heart and lung transplantation in children," Lancet, 368:53-69 (Jul. 2006).
Wei, G., et al., "Keratinocyte Growth Factor Combined with a Sodium Hyaluronate Gel Inhibits Postoperative Intra-Abdominal Adhesions," Int J Mol Sci., 17:1611 (2016).
Wells, J.A., "Additivity of Mutational Effects in Proteins," Biochemistry 29(37):8509-8517 (1990).
Weyand, et al., "Serial Interleukin-6 Blood Levels Early After Cardiac Transplantation", Transplantation Proceedings 24(6):2546 (1992).
Wiens, G.D., et al., "Mutation of a Single Conserved Residue in VH Complementarity-determining Region 2 Results in a Severe Ig Secretion Defect," Journal of Immunology (Baltimore, Md. : 1950), 167(4):2179-2186, Williams & Wilkins, c1950-, United States (Aug. 15, 2001).
Wiens, G.D., et al., "Somatic Mutation in VH Complementarity-determining Region 2 and Framework Region 2: Differential Effects on Antigen Binding and Ig Secretion," Journal of Immunology (Baltimore, Md. : 1950), 159(3):1293-1302, American Association of Immunologists, United States (Aug. 1, 1997).
Wikipedia, "Chaotropic agent," [online], [retrieved on Nov. 2, 2015]. Retrieved from the Internet: https://en.wikipedia.org/wiki/Chaotropicagent.
Wikipedia, "Interleukin 6," Feb. 22, 2019, XP055598802, accessed on https://protect-us.mimecast.com/s/6UxpCmZ28nsApl8JuGhTki?domain=en.wikipedia.org, accessed at Jun. 24, 2019, 20 pages.
Wilansky, S., "Echocardiography in the Assessment of Complications of Myocardial Infarction," Texas Heart Institute Journal 18(4):237-242 (1991).

(56) References Cited

OTHER PUBLICATIONS

Wingerchuk, D.M., et al., "International Consensus Diagnostic Criteria for Neuromyelitis Optica Spectrum Disorders," Neurology 85:177-189 (2015).
Wingerchuk, D.M., et al., "Revised Diagnostic Criteria for Neuromyelitis Optica," Neurology 66(10):1485-1489 (2006).
Wingerchuk, D.M., et al., "The spectrum of neuromyelitis optica," Lancet Neurol., 6:805-815 (2007).
Wojciak et al., "The Crystal Structure of Sphingosine-1-Phosphate in Complex With a Fab Fragment Reveals Metal Bridging of an Antibody and Its Antigen," Proceedings of the National Academy of Sciences of the United States of America, 106(42):17717-17722—2009.
Wong, et al., "Progress in Heart Transplantation," Cardiovascular Pathology, 14:176-180 (2005).
Wright, H. L., et al., "Neutrophil biomarkers predict response to therapy with tumor necrosis factor inhibitors in rheumatoid arthritis," J Leukoc Biol., 101:785-795 (2017).
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Stepwise in Vitro Affinity Maturation Ofvitaxin, an Av-33-specific Humanized Mab," Proceedings of the National Academy of Sciences USA, 95(11):6037-6042 (1998).
Wu, H., et al., "Development of Motavizumab, an Ultra-potent Antibody for the Prevention of Respiratory Syncytial Virus Infection in the Upper and Lower Respiratory Tract," Journal of Molecular Biology 368:652-665 (2007).
Wu, H., et al., "Humanization of a Murine Monoclonal Antibody by Simultaneous Optimization of Framework and CDR Residues," Journal of Molecular Biology 294(1):151-162 (1999).
Wu, H., et al., "Ultra-potent Antibodies Against Respiratory Syncytial Virus: Effects of Binding Kinetics and Binding Valence on Viral Neutralization," Journal of Molecular Biology, 350(1):126-144 (2005).
Wu, C.T., et al., "Predictive Value of CD44 in Muscle-Invasive Bladder Cancer and Its Relationship with IL-6 Signaling," Annals of Surgical Oncology 25(12):3518-3526 (2018).
Wypych, J., et al., "Human IgG2 Antibodies Display Disulfide-mediated Structural Isoforms," The Journal of Biological Chemistry 283(23):16194-16205, American Society for Biochemistry and Molecular Biology, United States (Jun. 2008).
Xiang, J., et al., "Study of B72.3 Combining Sites by Molecular Modeling and Site-directed Mutagenesis," Protein Engineering, 13(5):339-344 (May 2000).
Xing, Y., et al., "The Effect of Interleukin-6 on the Proliferation of Prostate Cancer Cellsin Vitro and the Modulation of This Procedure", Journal of Tongji Medical University 21:225-227, SpringerLink (2001).
Yamakawa, Y., et al., "Astrocytes Promote the Proliferation of Lung Cancer Cells in Brain Metastases via Inflammatory Cytokines, Especially IL-6," Neuroscience 48(213):216, P-22 (2009).
Yamamoto et al., "Molecular Studies of PH-dependent Ligand Interactions With the Low-density Lipoprotein Receptor," Biochemistry, 47(44):11647-11652 (Nov. 2008).
Yamamoto et al., "Regulator Mechanisms for Production of IFN-y and TNF by Antitumor T Cells or Macroophages in the Tumor-Bearing State," Journal of Immunology, 154:2281-2290 (1995).
Yamamura, T., et al., "EPR3103—A double-blind placebo-controlled study of satralizumab (SA237), a recycling anti-IL-6 receptor monoclonal antibody, as add-on therapy for neuromyelitis optica (NMO) and NMO spectrum disorder (NMOSD)," European Journal of Neurology, 25(Supp 2):536 (2018).
Yamasaki, K., et al., "Cloning and Expression of the Human Interleukin-6 (BSF-2/IFN/3 2) Receptor," Science, 241(4867):825-828 (1988).
Yamasaki, Y., et al., "Pharmacokinetic Analysis of in Vivo Disposition of Succinylated Proteins Targeted to Liver Nonparenchymal Cells via Scavenger Receptors: Importance of Molecular Size and Negative Charge Density for in Vivo Recognition by Receptors," The Journal of Pharmacology and Experimental Therapeutics, 301(2):467-477, American Society for Pharmacology and Experimental Therapeutics, United States (May 2002).
Yamauchi-Takihara, K., et al., "Hypoxic Stress Induces Cardiac Myocyte-derived Interleukin-6", Circulation 91:1520-1524 (1995).
Yan, L., "(II) Abdominal discomfort and pain," Theory and Practice of Oncology, C43 Shandong Science and Technology Press, 2 pages (2006).
Yang, K., et al., "Tailoring Structure-function and Pharmacokinetic Properties of Single-chain Fv Proteins by Site-specific PEGylation," Protein Engineering, 16(10):761-770, Oxford University Press, England (Oct. 2003).
Yang, W.P., et al., "CDR Walking Mutagenesis for the Affinity Maturation of a Potent Human Anti-HIV-1 Antibody Into the Picomolar Range," Journal of Molecular Biology, 254(3):392-403, Elsevier, England (Dec. 1995).
Yang, Y.F., et al., "Enhanced Induction of Antitumor T-Cell Responses by Cytotoxic T Lymphocyte-associated Molecule-4 Blockade: The Effect Is Manifested Only at the Restricted Tumor-bearing Stage," Cancer Research 57: 4036-4041 (1997).
Yarilin, A., "Osnovy Immunologii," M.: Meditsina, 1999: pp. 169-172, 354-358/Fundamentals of Immunology. M: Medicina, 1999: pp. 169-172, 354-358.
Yarilin, A., "Osnovy Immunologii," M.: Meditsina, 1999: pp. 172-174/Fundamentals of Immunology. M: Medicina, 1999: pp. 172-174.
Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671, American Association of Immunologists, United States (Jun. 2009).
Yokota, S., et al., "Clinical Study of Tocilizumab in Children With Systemic-Onset Juvenile Idiopathic Arthritis," Clinical Reviews in Allergy & Immunology 28(3):231-238, Humana Press, United States (Jun. 2005).
Yoshio-Hoshino et al., "Establishment of a New Interleukin-6 (IL-6) Receptor Inhibitor Applicable to the Gene Therapy for IL-6-Dependent Tumor," Cancer Research 67:871-875 (2007).
Yue, P., et al., "Cytokine Expression Increases in Nonmyocytes From Rats With Postinfarction Heart Failure," The American Journal of Physiology, 275(1):H250-H258 (1998).
Zaki, M.H., et al., "CNTO 328, A Monoclonal Antibody to IL-6, Inhibits Human Tumor-induced Cachexia in Nude Mice", International Journal of Cancer 111:592-595 (2004).
Zalevsky, J., et al., "Enhanced Antibody Half-life Improves in Vivo Activity," Nature Biotechnology 28(2):157-159, Nature America Publishing, United States (Feb. 2010).
Zangari, M., et al., "Immunomodulatory Drugs in Multiple Myeloma," Expert Opinion on Investigational Drugs 14(11):1411-1418 (2005).
Zhang, G.-J. and Adachi, I., "Serum Interleukin-6 Levels Correlate to Tumor Progression and Prognosis in Metastatic Breast Carcinoma," Anticancer Research, 19:1427-1432 (1999).
Zhou, T., et al., "Interfacial Metal and Antibody Recognition," Proceedings of the National Academy of Sciences of the United States of America, 102(41):14575-14580, National Academy of Sciences, United States (Oct. 2005).
Zhu, X., et al., "MHC Class I-Related Neonatal Fc Receptor for IgG Is Functionally Expressed in Monocytes, Intestinal Macrophages, and Dendritic Cells", Journal of Immunology 166:3266-3276, American Association of Immunologists, United States (Mar. 2001).
Zijun, L, "Tissue Infiltration," Tumor Metastasis, Shanxi Science and Technology Press, 5 pages (2007).
Zuckier, L.S., et al., "Chimeric Human-mouse IgG Antibodies With Shuffled Constant Region Exons Demonstrate That Multiple Domains Contribute to in Vivo Half-life," Cancer Research, 58(17):3905-3908, American Association for Cancer Research, United States (Sep. 1, 1998).
Zwick, M.B., et al., "The Long Third Complementarity-determining Region of the Heavy Chain is Important in the Activity of the

(56) References Cited

OTHER PUBLICATIONS

Broadly Neutralizing Anti-human Immunodeficiency Virus Type 1 Antibody 2F5," Journal of Virology, 78(6):3155-3161, American Society for Microbiology, United States (Mar. 2004).
U.S. Appl. No. 07/364,056, filed Jun. 9, 1989, Mcdonough et al.
U.S. Appl. No. 07/530,580, filed May 30, 1990, Novick et al.
U.S. Appl. No. 07/634,278, filed Dec. 19, 1990, Queen et al.
U.S. Appl. No. 08/137,117, filed Dec. 20, 1993, Tsuchiya et al.
U.S. Appl. No. 08/197,834, filed Feb. 17, 1994, Shimamura et al.
U.S. Appl. No. 08/329,785, filed Oct. 27, 1994, Novick et al.
U.S. Appl. No. 08/357,080, filed Dec. 15, 1994, Kishimoto.
U.S. Appl. No. 08/436,717, filed May 8, 1995, Tsuchiya et al.
U.S. Appl. No. 08/525,539, filed Sep. 14, 1995, Do Couto et al.
U.S. Appl. No. 08/553,501, filed Feb. 20, 1996, Tsuchiya et al.
U.S. Appl. No. 08/817,084, filed Apr. 7, 1997, Kishimoto et al.
U.S. Appl. No. 08/875,927, filed Aug. 13, 1997, Tsujinaka et al.
U.S. Appl. No. 08/882,447, filed Jun. 26, 1997, Barbera-Guillem.
U.S. Appl. No. 09/205,231, filed Dec. 4, 1998, Tsuchiya et al.
U.S. Appl. No. 09/646,188, filed Sep. 14, 2000, Ito et al.
U.S. Appl. No. 09/756,125, filed Jan. 9, 2001, Kishimoto et al.
U.S. Appl. No. 10/030,915, filed May 23, 2002, Isobe et al.
U.S. Appl. No. 10/120,272, filed Apr. 9, 2002, Kirk et al.
U.S. Appl. No. 10/141,766, filed May 10, 2002, Mihara et al.
U.S. Appl. No. 10/280,716, filed Oct. 26, 2002, Giles-Komar et al.
U.S. Appl. No. 10/399,979, filed Apr. 24, 2003, Ito et al.
U.S. Appl. No. 10/496,793, filed Nov. 30, 2004, Blay et al.
U.S. Appl. No. 10/522,426, filed Mar. 25, 2005, Bahlmann et al.
U.S. Appl. No. 10/546,149, filed Aug. 22, 2005, Okano et al.
U.S. Appl. No. 10/554,407, filed Oct. 24, 2005, Okuda et al.
U.S. Appl. No. 10/569,831, filed Feb. 28, 2006, Nakade et al.
U.S. Appl. No. 10/573,528, filed Mar. 24, 2006, Ochiai et al.
U.S. Appl. No. 10/575,455, filed Aug. 9, 2006, Nishimoto et al.
U.S. Appl. No. 10/593,786, filed Aug. 26, 2008, Kano et al.
U.S. Appl. No. 10/607,050, filed Jun. 27, 2003, Yamamura et al.
U.S. Appl. No. 10/677,227, filed Oct. 3, 2003, Ito et al.
U.S. Appl. No. 10/714,353, filed Nov. 14, 2003, Schuurman et al.
U.S. Appl. No. 10/922,675, filed Aug. 20, 2004, Mcswiggen et al.
U.S. Appl. No. 10/926,806, filed Aug. 26, 2004, Shima et al.
U.S. Appl. No. 11/089,426, filed Mar. 24, 2005, Gillies et al.
U.S. Appl. No. 11/197,488, filed Aug. 5, 2005, Young et al.
U.S. Appl. No. 11/244,142, filed Oct. 6, 2005, Lawless.
U.S. Appl. No. 11/340,412, filed Jan. 25, 2006, Mihara.
U.S. Appl. No. 11/514,217, filed Sep. 1, 2006, Yoshizaki et al.
U.S. Appl. No. 11/585,172, filed Oct. 24, 2006, Kishimoto et al.
U.S. Appl. No. 11/608,342, filed Dec. 8, 2006, Zaki, M., et al.
U.S. Appl. No. 11/631,128, filed Feb. 20, 2007, Kudou et al.
U.S. Appl. No. 11/809,482, filed Jun. 1, 2007, Stevens et al.
U.S. Appl. No. 11/858,418, filed Sep. 20, 2007, Nemeth.
U.S. Appl. No. 12/085,065, filed Jan. 6, 2009, Okada et al., related application.
U.S. Appl. No. 12/090,061, filed Jun. 3, 2009, Yasunami, related application.
U.S. Appl. No. 12/090,676, filed Feb. 25, 2009, Kobara, related application.
U.S. Appl. No. 12/094,644, filed Feb. 27, 2009, Nakashima et al., related application.
U.S. Appl. No. 12/153,612, filed May 21, 2008, Garcia-Martinez et al.
U.S. Appl. No. 12/159,778, filed Jun. 30, 2008, Morichika et al.
U.S. Appl. No. 12/161,733, filed Sep. 3, 2009, Ishida., related application.
U.S. Appl. No. 12/232,341, filed Sep. 16, 2008, Mihara et al.
U.S. Appl. No. 12/295,039, filed Jan. 20, 2009, Igawa.
U.S. Appl. No. 12/296,193, filed Apr. 15, 2009, Nishimoto et al., related application.
U.S. Appl. No. 12/502,581, filed Jul. 14, 2009, Garcia-Martinez et al.
U.S. Appl. No. 12/524,041, filed Sep. 18, 2009, Takahashi et al., related application.
U.S. Appl. No. 12/679,922, filed Oct. 1, 2010, Igawa et al.
U.S. Appl. No. 12/680,082, filed Jun. 25, 2010, Igawa et al.
U.S. Appl. No. 12/680,087, filed Mar. 1, 2011, Igawa et al., related application.
U.S. Appl. No. 12/680,112, filed Jun. 23, 2010, Igawa et al., related application.
U.S. Appl. No. 12/780,006, filed May 14, 2010, Radin et al.
U.S. Appl. No. 12/860,112, filed Aug. 20, 2010, Chen et al.
U.S. Appl. No. 12/936,587, filed Mar. 1, 2011, Igawa et al.
U.S. Appl. No. 12/996,162, filed Jul. 3, 2011, Mitsunaga et al., related application.
U.S. Appl. No. 13/257,145, filed Nov. 22, 2011, Igawa et al.
U.S. Appl. No. 13/283,177, filed Oct. 27, 2011, Chen et al.
U.S. Appl. No. 13/290,366, filed Nov. 7, 2011, Zhang et al.
U.S. Appl. No. 13/387,292, filed Mar. 4, 2012, Maeda et al., related application.
U.S. Appl. No. 13/524,528, filed Jun. 15, 2012, Igawa et al., related application.
U.S. Appl. No. 13/595,139, filed Aug. 27, 2012, Igawa et al.
U.S. Appl. No. 13/700,355, filed Feb. 4, 2013, Nishimura, related application.
U.S. Appl. No. 13/889,484, filed Aug. 5, 2013, Igawa et al.
U.S. Appl. No. 13/889,512, filed Aug. 5, 2013, Igawa et al.
U.S. Appl. No. 13/959,489, filed May 8, 2013, Igawa et al., related application.
U.S. Appl. No. 13/990,158, filed Mar. 28, 2014, Igawa et al.
U.S. Appl. No. 14/520,423, filed Oct. 22, 2014, Igawa et al., related application.
U.S. Appl. No. 14/680,250, filed Jul. 4, 2015, Igawa et al.
U.S. Appl. No. 14/741,786, filed Jun. 17, 2015, Igawa et al.
U.S. Appl. No. 14/878,163, filed Oct. 8, 2015, Mitsunaga, et al.
U.S. Appl. No. 14/897,498, filed Oct. 12, 2015, Yamamura et al., related application.
U.S. Appl. No. 14/962,293, filed Aug. 12, 2015, Igawa et al.
U.S. Appl. No. 15/263,617, filed Sep. 13, 2016, Igawa et al., related application.
U.S. Appl. No. 15/503,441, filed Feb. 13, 2017, Fukuda et al.
U.S. Appl. No. 15/553,609, filed Aug. 25, 2017, Igawa et al., related application.
U.S. Appl. No. 15/575,027, filed Nov. 17, 2017, Yamamura et al., related application.
U.S. Appl. No. 15/614,842, filed Jun. 6, 2017, Igawa et al.
U.S. Appl. No. 15/725,692, filed May 10, 2017, Igawa et al.
U.S. Appl. No. 15/877,894, filed Jan. 23, 2018, Maeda, related application.
U.S. Appl. No. 15/952,945, filed Apr. 13, 2018, Igawa et al.
U.S. Appl. No. 15/952,951, filed Apr. 13, 2018, Igawa et al.
U.S. Appl. No. 15/988,348, filed May 24, 2018, Igawa et al.
U.S. Appl. No. 16/041,976, filed Jul. 23, 2018, Igawa et al., related application.
U.S. Appl. No. 16/298,032, filed Nov. 3, 2019, Igawa et al.
U.S. Appl. No. 16/361,498, filed Mar. 22, 2019, Igawa et al.
U.S. Appl. No. 16/756,404, 371(c) date Apr. 15, 2020, Fujimoto et al., related application.
U.S. Appl. No. 16/838,415, filed Apr. 2, 2020, Igawa et al., related application.
U.S. Appl. No. 16/963,311, 371(c) date Jul. 20, 2020, Mato, related application.
U.S. Appl. No. 16/983,115, filed Aug. 3, 2020, Kakehi et al., related application.
U.S. Appl. No. 17/097,298, filed Nov. 13, 2020, Igawa et al., related application.
U.S. Appl. No. 17/437,448, filed Sep. 9, 2021, Takeshita et al., related application.
U.S. Appl. No. 17/509,128, filed Oct. 25, 2021, Igawa et al., related application.
U.S. Appl. No. 17/601,831, filed Oct. 6, 2021, Honda et al., related application.
U.S. Appl. No. 17/829,641, filed Jun. 1, 2022, Igawa et al., related application.
U.S. Appl. No. 12/085,065, filed Jan. 6, 2009, Okada et al.
U.S. Appl. No. 12/090,061, filed Jun. 3, 2009, Yasunami.
U.S. Appl. No. 12/090,676, filed Feb. 25, 2009, Kobara.
U.S. Appl. No. 12/094,644, filed Feb. 27, 2009, Nakashima et al.

(56) References Cited

OTHER PUBLICATIONS

U.S. Appl. No. 12/161,733, filed Sep. 3, 2009, Ishida.
U.S. Appl. No. 12/296,193, filed Apr. 15, 2009, Nishimoto et al.
U.S. Appl. No. 12/524,041, filed Sep. 18, 2009, Takahashi et al.
U.S. Appl. No. 12/680,087, filed Mar. 1, 2011, Igawa et al.
U.S. Appl. No. 12/680,112, filed Jun. 23, 2010, Igawa et al.
U.S. Appl. No. 12/996,162, filed Jul. 3, 2011, Mitsunaga et al.
U.S. Appl. No. 13/387,292, filed Mar. 4, 2012, Maeda et al.
U.S. Appl. No. 13/524,528, filed Jun. 15, 2012, Igawa et al.
U.S. Appl. No. 13/700,355, filed Feb. 4, 2013, Nishimura.
U.S. Appl. No. 13/959,489, filed May 8, 2013, Igawa et al.
U.S. Appl. No. 14/520,423, filed Oct. 22, 2014, Igawa et al.
U.S. Appl. No. 14/897,498, filed Oct. 12, 2015, Yamamura et al.
U.S. Appl. No. 15/263,617, filed Sep. 13, 2016, Igawa et al.
U.S. Appl. No. 15/553,609, filed Aug. 25, 2017, Igawa et al.
U.S. Appl. No. 15/575,027, filed Nov. 17, 2017, Yamamura et al.
U.S. Appl. No. 15/877,894, filed Jan. 23, 2018, Maeda.
U.S. Appl. No. 16/041,976, filed Jul. 23, 2018, Igawa et al.,.
U.S. Appl. No. 16/756,404, 371(c) date Apr. 15, 2020, Fujimoto et al.
U.S. Appl. No. 16/838,415, filed Apr. 2, 2020, Igawa et al.
U.S. Appl. No. 16/963,311, 371(c) date Jul. 20, 2020, Mato.
U.S. Appl. No. 16/983,115, filed Aug. 3, 2020, Kakehi et al.
U.S. Appl. No. 17/097,298, filed Nov. 13, 2020, Igawa et al.
U.S. Appl. No. 17/437,448, filed Sep. 9, 2021, Takeshita et al.
U.S. Appl. No. 17/509,128, filed Oct. 25, 2021, Igawa et al.
U.S. Appl. No. 17/601,831, filed Oct. 6, 2021, Honda et al.
U.S. Appl. No. 17/829,641, filed Jun. 1, 2022, Igawa et al.
Notice of Allowance dated Aug. 22, 2011 for U.S. Appl. No. 12/085,065, Okada, M., et al., Jun. 1, 2009.
Office Action dated Feb. 23, 2018 in U.S. Appl. No. 15/263,617, Igawa, et al., dated Sep. 13, 2016.
Abdalla, A. M. E., et al., "Current Challenges of Cancer Anti-angiogenic Therapy and the Promise of Nanotherapeutics," Theranostics, 8(2):533-548 (2018).
Airoldi, I., et al., "IL-12 Can Target Human Lung Adenocarcinoma Cells and Normal Bronchial Epithelial Cells Surrounding Tumor Lesions," PLoS One, 4(7): e6119 (2009).
Hashizume, M., et al., "IL-6 plays an essential role in neutrophilia under inflammation," Cytokine, 54:92-99 (2011).
Rikiishi, H., et al., "The roles of cytokine in organ-specific tumor metastasis," Hum Cell., 6(1):21-28 (1993).
Shang, G.-S., et al., "IL-6 and TNF-α promote metastasis of lung cancer by inducing epithelial- mesenchymal transition," Oncol Lett., 13:4657-4660 (2017).
Snow, M. H., "Myogenic Cell Formation in Regenerating Rat Skeletal Muscle Injured by Mincing," Anat Rec., 188:181-200 (1977).
Sumida, K., et al., "Anti-IL-6 receptor mAb eliminates myeloid-derived suppressor cells and inhibits tumor growth by enhancing T-cell responses," Eur J Immunol., 42:2060-2072 (2012).
Takizawa, H., et al., "Growth Inhibition of Human Lung Cancer Cell Lines by Interleukin 6 in Vitro: A Possible Role in Tumor Growth via an Autocrine Mechanism," Cancer Res., 53:4175-4181 (1993).
Weber, G. F., "Why does cancer therapy lack effective anti-metastasis drugs?" Cancer Lett., 328:207-211 (2013).
U.S. Appl. No. 18/096,066, filed Jan. 12, 2023, Igawa et al., related application.

* cited by examiner

METHOD FOR PREDICTING AND EVALUATING THERAPEUTIC EFFECT IN DISEASES RELATED TO IL-6 AND NEUTROPHILS

CROSS-REFERENCE TO RELATED APPLICATIONS

This application is a U.S. National Phase of PCT Application No. PCT/JP2018/017374, filed May 1, 2018, which claims the benefit of Japanese Patent Application No. 2017-091600, filed May 2, 2017, each of which is incorporated herein by reference in its entirety.

REFERENCE TO SEQUENCE LISTING SUBMITTED ELECTRONICALLY

The content of the electronically submitted sequence listing (Name: 6663-0124_Sequence_Listing.txt; Size: 43.7 kilobytes; and Date of Creation: Oct. 25, 2019) filed with the application is incorporated herein by reference in its entirety.

TECHNICAL FIELD

The present invention relates to methods for predicting the therapeutic effect of an IL-6 inhibitor in patients with IL-6- and neutrophil-associated diseases (may be referred to as neutrophil-associated diseases hereinbelow). The present invention also relates to methods for determining the therapeutic effect of an IL-6 inhibitor in patients with neutrophil-associated diseases. Furthermore, the present invention relates to agents for treating neutrophil-associated diseases comprising an IL-6 inhibitor, and particularly to agents for treating neutrophil-associated diseases which are administered to patients with high expression levels of neutrophil-associated genes. In addition, the present invention also relates to methods for treating neutrophil-associated diseases, and the methods are characterized in that an IL-6 inhibitor is administered to patients with high expression levels of neutrophil-associated genes.

BACKGROUND ART

Diseases in which IL-6 is associated with their pathological conditions (IL-6-associated diseases), such as neuromyelitis optica (NMO), rheumatoid arthritis, and juvenile idiopathic arthritis, are known as diseases that are treatable with interleukin-6 (IL-6) inhibitors (Non-patent Documents 1 and 2). As IL-6 inhibitors, ingredients such as the following are utilized (Patent Document 1):
Anti-IL-6 antibodies,
Anti-IL-6 receptor (IL-6R) antibodies,
Signal transducer and activator of transcription 3 (STAT3) inhibitors, and
Janus kinase-1 (JAK1) inhibitors.

Among these known IL-6 inhibitors, for example, tocilizumab (TCZ; generic name), an anti-IL-6R antibody, has been approved as a therapeutic drug for Castleman's disease, rheumatoid arthritis, and juvenile idiopathic arthritis.

Meanwhile it is known that one of the actions of tocilizumab is to decrease or increase the number of neutrophils. Neutrophils have been reported to be associated with the pathological condition of neuromyelitis optica (NMO) (Non-patent Documents 3 and 4). In addition to NMO, Neuro-Sweet disease, stroke, cerebral infarction, and such are known as diseases in which IL-6 and neutrophils are associated with their pathological conditions (IL-6- and neutrophil-associated diseases; Non-patent Document 5). However, it is not known how tocilizumab affects the viability and function of neutrophils, and further elucidation of the mechanism of action of IL-6 inhibitors, represented by anti-IL-6R antibodies, is desired.

CITATION LIST

Patent Document

[Patent Document 1] WO2010/035769

Non-Patent Document

[Non-patent Document 1] Neurology 2014; 82; 1302-1306
[Non-patent Document 2] Annu. Rev. Pharmacol. Toxicol. 2012.52:199-219
[Non-patent Document 3] Multiple Sclerosis Journal, 18(12), 1801-1803, 2012
[Non-patent Document 4] ANN NEUROL 2012; 71: 323-333
[Non-patent Document 5] Clinical Neurology 2012; 52:1234-1236

SUMMARY OF THE INVENTION

Problems to be Solved by the Invention

An objective of the present invention is to provide a new strategy for treating neutrophil-associated diseases by elucidating the mechanism of action of IL-6 inhibitors.

Means for Solving the Problems

The present inventors conducted intense research to solve the above-mentioned problems. Specifically, they first administered tocilizumab, an IL-6 inhibitor, to neuromyelitis optica patients as subjects, and analyzed by DNA microarray genes that were highly expressed compared to healthy individuals prior to administration and that reduced expression after administration. The results revealed that among the genes with greater fluctuation in expression level, the top nine genes are related to the granule content of neutrophils. It has not been known until now that inhibiting IL-6R alters genes associated with neutrophils (referred to as neutrophil-associated genes hereinbelow). Based on this finding, the present inventors have found that the expression levels of the neutrophil-associated genes can be used as an indicator for predicting or determining the therapeutic effect of IL-6 inhibitors for neutrophil-associated diseases. The present inventors have also found that IL-6 inhibitors are useful for the treatment of neutrophil-associated diseases.

The present invention is based on such findings and specifically relates to the following inventions.
[1] A method for predicting the therapeutic effect of an IL-6 inhibitor in a patient with an IL-6- and neutrophil-associated disease, comprising:
(i) measuring the expression level of a neutrophil-associated gene in a sample obtained from the patient with an IL-6- and neutrophil-associated disease, and
(ii) comparing the expression level measured in step (i) with a control, wherein the therapeutic effect of the IL-6 inhibitor is indicated to be high when the expression level is higher than the control.
[2] The method of [1], wherein the control is the expression level of the neutrophil-associated gene in a sample obtained from a healthy individual.

[3] The method of [1], wherein in step (ii), the therapeutic effect of the IL-6 inhibitor is indicated to be high when the expression level measured in step (i) is five times or higher than the expression level of the neutrophil-associated gene in a sample obtained from a healthy individual.

[4] The method of [1], wherein in step (ii), the therapeutic effect of the IL-6 inhibitor is indicated to be high when the expression level measured in step (i) is ten times or higher than the expression level of the neutrophil-associated gene in a sample obtained from a healthy individual.

[5] A method for determining the therapeutic effect of an IL-6 inhibitor in a patient with an IL-6- and neutrophil-associated disease, comprising:
  (i) measuring the expression level of a neutrophil-associated gene in a sample obtained from the patient with an IL-6- and neutrophil-associated disease who has been administered with the IL-6 inhibitor, and
  (ii) comparing the expression level measured in step (i) with a control, wherein the therapeutic effect of the IL-6 inhibitor is indicated to be high when the expression level is lower than the control.

[6] The method of [5], wherein the control is the expression level of the neutrophil-associated gene in a sample obtained from the patient prior to administration of the IL-6 inhibitor.

[7] The method of [5], wherein in step (ii), the therapeutic effect of the IL-6 inhibitor is indicated to be high when the expression level measured in step (i) is less than 0.5 times the expression level of the neutrophil-associated gene in a sample obtained from the patient prior to administration of the IL-6 inhibitor.

[8] The method of [5], wherein in step (ii), the therapeutic effect of the IL-6 inhibitor is indicated to be high when the expression level measured in step (i) is less than 0.2 times the expression level of the neutrophil-associated gene in a sample obtained from the patient prior to administration of the IL-6 inhibitor.

[9] The method of any one of [1] to [8], wherein the neutrophil-associated gene is at least one gene selected from the group consisting of CTSG (cathepsin G), DEFA4 (defensin, alpha 4, corticostatin), AZU1 (azurocidin 1), BPI (bactericidal/permeability-increasing protein), ELANE (elastase, neutrophil expressed), LTF (lactotransferrin), DEFA3 (defensin, alpha 3, neutrophil-specific), LCN2 (lipocalin 2), and CAMP (cathelicidin antimicrobial peptide).

[10] The method of any one of [1] to [9], wherein the neutrophil-associated gene is at least one gene selected from the group consisting of CTSG (cathepsin G), DEFA4 (defensin, alpha 4, corticostatin), and AZU1 (azurocidin 1).

[11] The method of any one of [1] to [10], wherein the IL-6 inhibitor is an anti-IL-6 receptor antibody.

[12] Use of a neutrophil-associated gene in predicting or determining the therapeutic effect of an IL-6 inhibitor for an IL-6- and neutrophil-associated disease.

[13] A therapeutic agent comprising an IL-6 inhibitor as an active ingredient, which is for administration to a patient in whom treatment with the IL-6 inhibitor has been indicated to be highly effective by the method of [1].

[14] A therapeutic agent comprising an IL-6 inhibitor as an active ingredient, which is for continued administration to a patient in whom treatment with the IL-6 inhibitor has been indicated to be highly effective by the method of [5].

[15] The therapeutic agent of [13] or [14], wherein the IL-6 inhibitor is an anti-IL-6 receptor antibody.

[16] The therapeutic agent of [15], wherein the anti-IL-6 receptor antibody is a chimeric antibody, a humanized antibody, or a human antibody.

[17] The therapeutic agent of [13], which is characterized in that it is administered to a patient in whom treatment with the IL-6 inhibitor has been judged to be highly effective by the method of any one of [1] to [11].

[18] A method for treating an IL-6- and neutrophil-associated disease, comprising administering an IL-6 inhibitor to a patient suffering from the IL-6- and neutrophil-associated disease, wherein a sample obtained from the patient shows high expression level of a neutrophil-associated gene.

[19] A method for treating an IL-6- and neutrophil-associated disease, comprising administering an IL-6 inhibitor to a patient in whom treatment with the IL-6 inhibitor has been judged to be highly effective by the method of any one of [1] to [11].

[20] An IL-6 inhibitor for use in the treatment of an IL-6- and neutrophil-associated disease, which is administered to a patient suffering from the IL-6- and neutrophil-associated disease, wherein a sample obtained from the patient shows high expression level of a neutrophil-associated gene.

[21] Use of an IL-6 inhibitor in the production of an agent for treating an IL-6- and neutrophil-associated disease, wherein the therapeutic agent is administered to a patient suffering from the IL-6- and neutrophil-associated disease, and wherein a sample obtained from the patient shows high expression level of a neutrophil-associated gene.

[22] Use of an IL-6 inhibitor in the treatment of an IL-6- and neutrophil-associated disease, which is characterized in that the expression level of a neutrophil-associated gene in a sample obtained from a patient receiving the treatment is high.

[23] A method for the manufacture of an agent for treating an IL-6- and neutrophil-associated disease comprising an IL-6 inhibitor as an active ingredient, wherein the therapeutic agent is administered to a patient suffering from the IL-6- and neutrophil-associated disease, and wherein a sample obtained from the patient shows high expression level of a neutrophil-associated gene.

[24] A kit for predicting or determining the therapeutic effect of an IL-6 inhibitor in a patient suffering from an IL-6- and neutrophil-associated disease, which is characterized in that it comprises a reagent for measuring the expression level of a neutrophil-associated gene.

[25] A reagent for detecting a neutrophil-associated gene for use in predicting or determining the therapeutic effect of an IL-6 inhibitor in a patient suffering from an IL-6- and neutrophil-associated disease.

[26] Use of a reagent for detecting a neutrophil-associated gene in the manufacture of an agent for predicting or determining the therapeutic effect of an IL-6 inhibitor in a patient suffering from an IL-6- and neutrophil-associated disease.

[27] Use of a reagent for detecting a neutrophil-associated gene in predicting or determining the therapeutic effect of an IL-6 inhibitor in a patient suffering from an IL-6- and neutrophil-associated disease.

[28] A method for detecting a marker for predicting or a marker for determining the therapeutic effect of an IL-6 inhibitor in a patient suffering from an IL-6- and neutrophil-associated disease, comprising measuring the expression level of a neutrophil-associated gene in a sample obtained from the patient.

[29] A method for classifying a patient suffering from an IL-6- and neutrophil-associated disease, comprising determining that a patient suffering from an IL-6- and neutrophil-associated disease, the expression level of a neutrophil-associated gene in a sample obtained from the patient being high, can be treated with high efficacy with an IL-6 inhibitor.

[30] The method, use, therapeutic agent, or kit of any one of [1] to [29], wherein the IL-6- and neutrophil-associated disease is neuromyelitis optica, Neuro-Sweet disease, stroke, or cerebral infarction.

[31] The method, use, therapeutic agent, or kit of any one of [1] to [30], wherein the IL-6- and neutrophil-associated disease is neuromyelitis optica.

Effects of the Invention

The present invention provides a method for predicting and determining the therapeutic effect of an IL-6 inhibitor in a neutrophil-associated disease using the expression level of a neutrophil-associated gene as an indicator. The method of the present invention allows one to avoid administering an IL-6 inhibitor to patients for whom therapeutic effect of the IL-6 inhibitor cannot be expected or patients who will be forced to experience severe side effects with an IL-6 inhibitor, and allows one to select the appropriate treatment regimen. In addition, the present invention shows that an IL-6 inhibitor is efficacious in treating a patient with a neutrophil-associated disease who has elevated level of expression of a neutrophil-associated gene. Thus, the present invention provides an agent and a method for treating a neutrophil-associated disease with high expression level of a neutrophil-associated gene.

MODE FOR CARRYING OUT THE INVENTION

Figure 1:
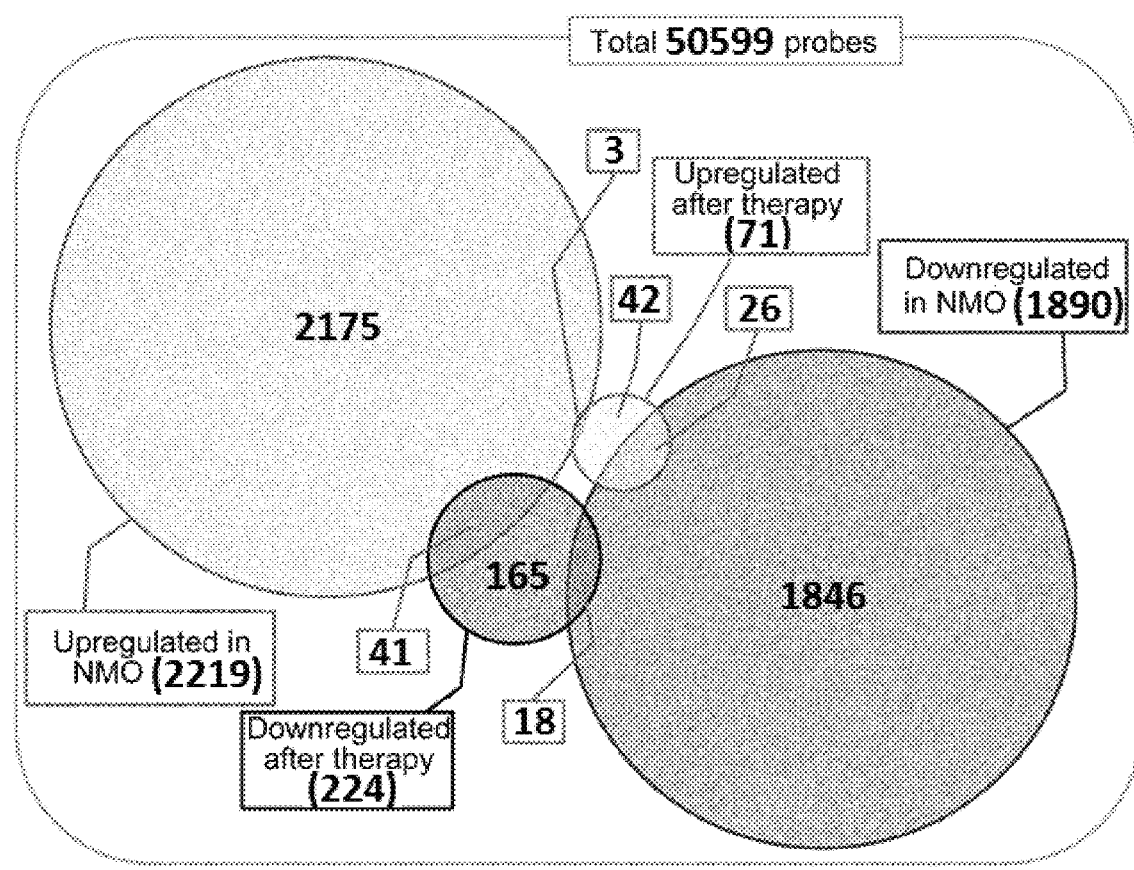
FIG. 1 is a Venn diagram showing the number of differentially expressed probes in each category.

The present invention will be described in detail below.

The present invention relates to genetic markers for predicting and/or determining the therapeutic effect of an IL-6 inhibitor in a patient with a neutrophil-associated disease (markers for determining whether or not treatment with an IL-6 inhibitor for a neutrophil-associated disease can be applied; also referred to as genetic markers of the present invention hereafter). In other words, the present invention relates to use of the genetic markers of the present invention in predicting or determining the therapeutic effect of an IL-6 inhibitor for a neutrophil-associated disease. The genetic markers of the present invention can be used to predict and/or determine that a patient with neutrophil-associated disease can be treated with high efficacy with an IL-6 inhibitor. Thus, the genetic markers of the present invention (or the marker genes of the present invention) can also be referred to as neutrophil-associated genes, genes associated with neutrophils and IL-6, or neutrophil/IL-6 associated genes. Genetic markers of the present invention may include, for example, the following genes:

CTSG (cathepsin G),
DEFA4 (defensin, alpha 4, corticostatin),
AZU1 (azurocidin 1),
BPI (bactericidal/permeability-increasing protein),
ELANE (elastase, neutrophil expressed),
LTF (lactotransferrin),
DEFA3 (defensin, alpha 3, neutrophil-specific),
LCN2 (lipocalin 2), and
CAMP (cathelicidin antimicrobial peptide).

One marker may be selected and used from among the markers listed herein as a marker of the present invention, and two or more markers may be selected and used in combination. That is, the neutrophil-associated gene in the present invention may be at least one gene selected from the group consisting of CTSG, DEFA4, AZU1, BPI, ELANE, LTF, DEFA3, LCN2, and CAMP. These neutrophil-associated genes can be any one, or two or more, preferably three or more, more preferably five or more, and all nine of them in a preferred embodiment.

The nucleic acid sequence and amino acid sequence of each of the marker genes listed here as examples of neutrophil-associated genes in humans are known as below.

|  | Nucleic acid sequence | Amino acid sequence |
| --- | --- | --- |
| CTSG (cathespin G; NM_001911) | SEQ ID NO: 1 | SEQ ID NO: 2 |
| DEFA4 (defensin, alpha 4, corticostatin; NM_001925) | SEQ ID NO: 3 | SEQ ID NO: 4 |
| AZU1 (azurocidin 1; NM_001700) | SEQ ID NO: 5 | SEQ ID NO: 6 |
| BPI (bactericidal/permeability-increasing protein; NM_001725) | SEQ ID NO: 7 | SEQ ID NO: 8 |
| ELANE (elastase, neutrophil expressed; NM_001972) | SEQ ID NO: 9 | SEQ ID NO: 10 |
| LTF (lactotransferrin; NM_002343) | SEQ ID NO: 11 | SEQ ID NO: 12 |
| DEFA3 (defensin, alpha 3, neutrophil-specific; NM_005217) | SEQ ID NO: 13 | SEQ ID NO: 14 |
| LCN2 (lipocalin 2; NM_005564) | SEQ ID NO: 15 | SEQ ID NO: 16 |
| CAMP (cathelicidin antimicrobial peptide; NM_004345) | SEQ ID NO: 17 | SEQ ID NO: 18 |

The structures of the homologs of various neutrophil-associated genes in non-human species, used as genetic markers, have also been revealed. Therefore, homologs of each gene can be selected depending on the animal species for evaluation in non-human model animals.

Diseases for which the therapeutic effect of an IL-6 inhibitor can be predicted/determined using the genetic markers of the present invention as indicators are diseases in which neutrophils are associated with their clinical conditions and diseases in which IL-6 is associated with theirs clinical conditions (referred to as "IL-6- and neutrophil-associated diseases" or "neutrophil/IL-6-associated diseases", and hereafter sometimes referred to as neutrophil-associated diseases). The diseases are characterized by high expression levels of genetic markers of the present invention (or neutrophil-associated genes, genes associated with neutrophils and IL-6, neutrophil/IL-6-associated genes). Examples of such diseases include, but are not limited to, neuromyelitis optica (NMO), Neuro-Sweet disease, stroke, cerebral infarction, and such. In the present invention, the term "neuromyelitis optica" includes neuromyelitis optica spectrum disorders.

Markers in the present invention refer to specific chemical substances in a living body that can also be rephrased as biomarkers, and they can be objectively measured and evaluated as indicators of normal biological processes, pathogenic processes, or pharmacological responsiveness to treatments. Markers are useful for assessment of the presence of, progression of, or susceptibility to a disease, for evaluation or prediction of the effect, optimal dosage, or safety of a drug, for prediction of prognosis, and such. Markers in the present invention are specified by their gene names. It is preferable to measure the marker genes as polypeptides or polynucleotides, and it is particularly preferable to measure them as polynucleotides.

The present invention relates to methods for predicting the therapeutic effect of an IL-6 inhibitor in a patient with a neutrophil-associated disease, which comprise measuring the expression level of a neutrophil-associated gene in a sample obtained from the patient suffering from a neutrophil-associated disease. The neutrophil-associated gene is preferably at least one gene selected from the group consisting of CTSG, DEFA4, AZU1, BPI, ELANE, LTF, DEFA3, LCN2, and CAMP.

In the above methods for predicting therapeutic effect of the present invention, the therapeutic effect of an IL-6 inhibitor for a neutrophil-associated disease is predicted to be high when the expression level of a genetic marker of the present invention in a patient with the neutrophil-associated disease is high. Thus, the methods of the present invention may further comprise a step of predicting that the therapeutic effect of an IL-6 inhibitor is high for a patient, a sample obtained from whom has a high expression level of a genetic marker of the present invention.

The present invention also relates to methods for determining the therapeutic effect of an IL-6 inhibitor in a patient with a neutrophil-associated disease, which comprise measuring the expression level of a neutrophil-associated gene in a sample obtained from the patient suffering from a neutrophil-associated disease who has been administered with the IL-6 inhibitor. The neutrophil-associated gene is preferably at least one gene selected from the group consisting of CTSG, DEFA4, AZU1, BPI, ELANE, LTF, DEFA3, LCN2, and CAMP.

In the above methods for determining therapeutic effect of the present invention, when the expression level of a genetic marker of the present invention in a patient with neutrophil-associated disease is reduced by administration of an IL-6 inhibitor, the therapeutic effect of the IL-6 inhibitor is determined to be high in this patient. The biological sample used to measure the expression level of a genetic marker of the present invention for determining the therapeutic effect of an IL-6 inhibitor is not particularly limited as long as it is a sample taken from a patient who has been administered with the IL-6 inhibitor and can be used in the determination. The sample is, for example, a sample obtained from a patient one month, two months, several months, one year, two years, or several years after administration of the IL-6 inhibitor.

The present invention relates to a method for predicting the therapeutic effect of an IL-6 inhibitor in a patient with a neutrophil-associated disease, which comprises
(i) measuring the expression level of a neutrophil-associated gene in a sample obtained from the patient with a neutrophil-associated disease, and
(ii) comparing the expression level measured in step (i) with a control, wherein the therapeutic effect of the IL-6 inhibitor is indicated to be high when the expression level is higher than the control.

Alternatively, the present invention can further comprise after (ii), a step of
(iii) administering the IL-6 inhibitor to the patient with a neutrophil-associated disease in whom treatment with the IL-6 inhibitor has been indicated to be highly effective.

That is, the present invention relates to a method for treating a neutrophil-associated disease comprising the steps of (i)-(iii).

Alternatively, the present invention relates to the use of a reagent for detecting the expression level of a neutrophil-associated gene in the manufacture of an agent for predicting or determining the therapeutic effect of an IL-6 inhibitor for a neutrophil-associated disease.

Alternatively, the present invention relates to the use of a reagent for detecting the expression level of a neutrophil-associated gene in predicting or determining the therapeutic effect of an IL-6 inhibitor for a neutrophil-associated disease.

Alternatively, the present invention relates to the use of a reagent for detecting the expression level of a neutrophil-associated gene in predicting or determining the therapeutic effect of an IL-6 inhibitor for a neutrophil-associated disease, wherein
(i) the expression level of a neutrophil-associated gene in a sample obtained from a patient with the neutrophil-associated disease is measured,
(ii) a high expression level of the neutrophil-associated gene compared with that of a healthy individual, or a low expression level of the neutrophil-associated gene in the patient after administration of the IL-6 inhibitor compared with that in the patient before administration of the IL-6 inhibitor indicates that the therapeutic effect of the IL-6 inhibitor is high, and
(iii) the IL-6 inhibitor is administered to the patient with the neutrophil-associated disease in whom treatment with the IL-6 inhibitor has been indicated to be highly effective.

The present invention also relates to the use of an IL-6 inhibitor in the treatment of a neutrophil-associated disease, wherein
(i) the expression level of a neutrophil-associated gene in a sample obtained from a patient with the neutrophil-associated disease is measured,
(ii) a high expression level of the neutrophil-associated gene compared with that of a healthy individual, or a low expression level of the neutrophil-associated gene in the patient after administration of the IL-6 inhibitor compared with that in the patient before administration of the IL-6 inhibitor indicates that the therapeutic effect of the IL-6 inhibitor is high, and
(iii) the IL-6 inhibitor is administered to the patient with the neutrophil-associated disease in whom treatment with the IL-6 inhibitor has been indicated to be highly effective.

Alternatively, the present invention relates to the use of a reagent for detecting the expression level of a neutrophil-associated gene in the manufacture of an agent for predicting or determining the therapeutic effect of an IL-6 inhibitor for a neutrophil-associated disease, wherein (i) the expression level of a neutrophil-associated gene in a sample obtained from a patient with the neutrophil-associated disease is measured,
(ii) a high expression level of the neutrophil-associated gene compared with that of a healthy individual, or a low expression level of the neutrophil-associated gene in the patient after administration of the IL-6 inhibitor compared with that in the patient before administration of the IL-6 inhibitor indicates that the therapeutic effect of the IL-6 inhibitor is high, and
(iii) the IL-6 inhibitor is administered to the patient with the neutrophil-associated disease in whom treatment with the IL-6 inhibitor has been indicated to be highly effective.

The present invention also relates to the use of an IL-6 inhibitor in the manufacture of an agent for treating a neutrophil-associated disease, wherein
(i) the expression level of a neutrophil-associated gene in a sample obtained from a patient with the neutrophil-associated disease is measured,
(ii) a high expression level of the neutrophil-associated gene compared with that of a healthy individual, or a low expression level of the neutrophil-associated gene in the patient after administration of the IL-6 inhibitor compared with that in the patient before administration of the IL-6 inhibitor indicates that the therapeutic effect of the IL-6 inhibitor is high, and
(iii) the IL-6 inhibitor is administered to the patient with the neutrophil-associated disease in whom treatment with the IL-6 inhibitor has been indicated to be highly effective.

Alternatively, the invention relates to a method for detecting a marker for predicting or determining the therapeutic effect of an IL-6 inhibitor for a neutrophil-associated disease, which comprises measuring the expression level of a neutrophil-associated gene in a sample obtained from a patient with the neutrophil-associated disease.

Alternatively, the invention relates to an IL-6 inhibitor or an agent for treating a neutrophil-associated disease, for use in the administration to a patient with a neutrophil-associated disease in whom treatment with the IL-6 inhibitor has been indicated to be highly effective by a method comprising the steps below, or for use in the treatment of a neutrophil-associated disease for which treatment with the IL-6 inhibitor has been indicated to be highly effective by a method comprising the steps below:
(i) measuring the expression level of a neutrophil-associated gene in a sample obtained from the patient with a neutrophil-associated disease, and
(ii) indicating that the therapeutic effect of the IL-6 inhibitor is high when the expression level of the neutrophil-associated gene is high compared with that of a healthy individual or when the expression level of the neutrophil-associated gene in the patient after administration of the IL-6 inhibitor is low compared with that in the patient before administration of the IL-6 inhibitor.

Alternatively, the present invention can further comprise after (ii), a step of
(iii) administering an IL-6 inhibitor or an agent for treating a neutrophil-associated disease to the patient with a neutrophil-associated disease in whom treatment with the IL-6 inhibitor has been indicated to be highly effective.

Alternatively, the present invention relates to an agent for treating a neutrophil-associated disease comprising an IL-6 inhibitor as an active ingredient, wherein
(i) the expression level of a neutrophil-associated gene in a sample obtained from a patient with the neutrophil-associated disease is measured,
(ii) a high expression level of the neutrophil-associated gene compared with that of a healthy individual, or a low expression level of the neutrophil-associated gene in the patient after administration of the IL-6 inhibitor compared with that in the patient before administration of the IL-6 inhibitor indicates that the therapeutic effect of the IL-6 inhibitor is high, and
(iii) the agent for treating a neutrophil-associated disease is for administration to a patient with the neutrophil-associated disease in whom treatment with the IL-6 inhibitor has been indicated to be highly effective.

Alternatively, the present invention relates to an agent for predicting or determining the therapeutic effect of an IL-6 inhibitor for a neutrophil-associated disease, comprising a reagent for detecting the expression level of a neutrophil-associated gene, wherein
(i) the expression level of a neutrophil-associated gene in a sample obtained from a patient with the neutrophil-associated disease is measured,
(ii) a high expression level of the neutrophil-associated gene compared with that of a healthy individual, or a low expression level of the neutrophil-associated gene in the patient after administration of the IL-6 inhibitor compared with that in the patient before administration of the IL-6 inhibitor indicates that the therapeutic effect of the IL-6 inhibitor is high, and
(iii) the predictor or determinant is for administering the IL-6 inhibitor to the patient with the neutrophil-associated disease in whom treatment with the IL-6 inhibitor has been indicated to be highly effective.

In the present invention, as the reagent for detecting the expression level of a neutrophil-associated gene, a reagent for detecting an mRNA encoding the gene to be detected or a translation product thereof (i.e., a protein) can be used. The translation product can be detected by using the amount of the protein or its biological activity as an indicator. Specifically, oligonucleotides that specifically bind to mRNA are among the typical detection reagents. Oligonucleotides can detect mRNA by their specific binding. In a known technique such as PCR, the mRNA to be detected can be amplified, and the mRNA can be detected using the amplification product as an indicator. Alternatively, antibodies that specifically bind to a protein which is a translation product are preferred detection reagents. Antibodies are useful for immunoassays and Western blot analysis. These detection reagents may be appropriately labelled or conjugated to a solid phase and applied to various assay formats.

Alternatively, the present invention also provides a kit for detecting a marker for predicting or determining therapeutic effect in a neutrophil-associated disease, comprising:
(i) a reagent for detecting the expression level of a neutrophil-associated gene in a sample, and
(ii) a positive control sample for the expression level of the neutrophil-associated gene.

The positive control sample is not particularly limited as long as the amount of the marker contained in a sample is preliminarily specified, and it can be appropriately prepared depending on the form of the marker measured by the kit. For example, when the form of the marker is a polypeptide, a sample containing polypeptides that are the same as the marker and have been isolated, purified, and quantified, is preferred as a positive control sample.

The kit of the present invention is a kit for detecting a marker for predicting or determining therapeutic effect in a neutrophil-associated disease, wherein (i) the expression level of a neutrophil-associated gene in a sample obtained from a patient with the neutrophil-associated disease is measured,
(ii) a high expression level of the neutrophil-associated gene compared with that of a healthy individual, or a low expression level of the neutrophil-associated gene in the patient after administration of the IL-6 inhibitor compared with that in the patient before administration of the IL-6 inhibitor indicates that the therapeutic effect of the IL-6 inhibitor is high, and
(iii) the kit is for administering the IL-6 inhibitor to the patient with the neutrophil-associated disease in whom treatment with the IL-6 inhibitor has been indicated to be highly effective.

In the present invention, a positive control sample is a sample comprising at least one transcription product (mRNA) or translation product (protein) of a neutrophil-associated gene in an amount that provides a level detected in a group of patients in whom treatment with an IL-6 inhibitor was highly effective. It is preferable that the positive control sample is the same as the sample actually taken from the patient for measurement. Therefore, when the target is a blood sample such as whole blood, the preferred positive control sample is also a blood sample. Blood samples include whole blood, serum, and plasma. The positive control can be liquid or lyophilized. In the case of a liquid sample, it may be concentrated.

The method for predicting the therapeutic effect of an IL-6 inhibitor in a patient suffering from a neutrophil-associated disease of the present invention can be rephrased as a method for evaluating the efficacy of an IL-6 inhibitor treatment in a patient suffering from a neutrophil-associated disease. It can also be rephrased as a method for selecting a patient who is suitable for an IL-6 inhibitor treatment from among patients suffering from neutrophil-associated diseases. Alternatively, it can also be rephrased as a method for detecting a marker for predicting the therapeutic effect of an IL-6 inhibitor or a marker for evaluating efficacy of the treatment in a patient suffering from a neutrophil-associated disease, or a marker for selecting a patient suitable for the treatment. These methods can be performed in vitro using samples obtained from patients.

In the present invention, the method for predicting the therapeutic effect can be rephrased as a method for predicting prognosis, a method for determining whether or not the treatment is applicable, a method for diagnosing the therapeutic effect, a method for deciding whether or not to continue the treatment, and such.

Also, in the present invention, the expression "the therapeutic effect is indicated to be high" can be rephrased as "the therapeutic effect is judged/determined to be high".

Also, "a patient with a neutrophil-associated disease in whom treatment with an IL-6 inhibitor has been indicated to be highly effective" in the present invention can be rephrased as "a patient suitable for IL-6 inhibitor therapy", "a patient responsive to IL-6 inhibitor therapy", or such. Therefore, the present invention relates to a method for identifying a patient suitable for treatment of a neutrophil-associated disease with an IL-6 inhibitor, comprising:
(i) measuring the expression level of a neutrophil-associated gene in a sample obtained from a patient with the neutrophil-associated disease, and
(ii) indicating that the therapeutic effect of the IL-6 inhibitor is high when the expression level of the neutrophil-associated gene is high compared to that in a healthy individual, or when the expression level of the neutrophil-associated gene is low in the patient after administration of the IL-6 inhibitor compared with that in the patient before administration of the IL-6 inhibitor.

The patient from whom the sample is obtained in the present invention may be any patient suffering from a neutrophil-associated disease. It may be a patient who has not yet been treated for a neutrophil-associated disease or a patient who is already receiving treatment. In the case of a patient already receiving treatment with an IL-6 inhibitor, the present invention provides a method for monitoring the responsiveness of the patient to an IL-6 inhibitor treatment, or a method for deciding whether or not to continue an IL-6 inhibitor treatment for the patient.

In the present invention, a high expression level of a marker means that the measured value of the marker is higher than the predetermined value set for that marker, and a low expression level of a marker means that the measured value of the marker is below the predetermined value set for that marker. Thus, in the present method for predicting therapeutic effect, when the expression level of a marker measured in a sample obtained from a patient is higher than the predetermined value set for the marker, the therapeutic effect of an IL-6 inhibitor is indicated to be high for the patient. In one embodiment, the method for predicting therapeutic effect of the present invention may include a step of comparing the expression level of a marker measured in a sample obtained from a patient with the predetermined value set for the marker, and a step of determining that the therapeutic effect of an IL-6 inhibitor is high for the patient when the measured expression level is higher than the predetermined value. Meanwhile, in the present method for determining therapeutic effect, when the expression level of a marker measured in a sample obtained from a patient who has been administered with an IL-6 inhibitor is lower than the predetermined value set for the marker, the therapeutic effect of the IL-6 inhibitor is indicated to be high for the patient. In one embodiment, the method for determining therapeutic effect of the present invention may include a step of comparing the expression level of a marker measured in a sample obtained from a patient who has been administered with an IL-6 inhibitor with the predetermined value set for the marker, and a step of determining that the therapeutic effect of the IL-6 inhibitor is high for the patient when the measured expression level is lower than the predetermined value.

The predetermined value in the present invention refers to a value determined in advance on the basis of some scientific evidence, and it may be any value as long as the value can be used as a baseline to determine whether the therapeutic effect of an IL-6 inhibitor is high or low in a patient suffering from a neutrophil-associated disease. A predetermined value in the present invention may be set for each marker.

The predetermined value in the present invention can be set from, for example, the measured value (control value) of a marker in a sample obtained from a healthy individual (control sample). Since it has already been found from the present research results that the measured value of a marker of the present invention is increased in a patient suffering from a neutrophil-associated disease compared to that in a healthy individual, a possible means may be setting the average value of the measured values of the marker in samples obtained from multiple healthy individuals as it is as the predetermined value, and another possible means may be adding a value of 1.0, 1.5, 2.0, 2.5, or 3.0 times the standard deviation to the average value of the measured values and setting it as the predetermined value. Alternatively, a value of 1.2, 1.5, 2.0, 2.5, 3.0, 3.5, 4.0 times or higher of the average value of the measured values of the marker in samples obtained from multiple healthy individuals may be set as the predetermined value. Thus, in one embodiment of the present method for predicting therapeutic effect, a higher expression level of the marker measured in a sample obtained from a patient suffering from a neutrophil-associated disease (e.g., 1.2, 1.5, 2.0, 2.5, 3.0, 3.5, 4.0 times or higher, preferably 5.0 times or more, and more preferably 10 times or more compared to the control) compared to the expression level of the marker measured in a sample obtained from a healthy individual (control sample) indicates that the therapeutic effect of an IL-6 inhibitor is high in the patient.

The predetermined value in the present invention can be set from, for example, the measured value (control value) of a marker in a sample obtained from a patient prior to administration of an IL-6 inhibitor (control sample). It has already been found from the present research results that the measured value of a marker of the present invention is decreased after administration of an IL-6 inhibitor in patients suffering from a neutrophil-associated disease compared to that prior to administration of the IL-6 inhibitor. Thus, in one embodiment, the measured value of a marker in a sample obtained from a patient prior to administration of an IL-6 inhibitor, or the average value of the measured values of the marker in samples obtained from multiple patients may be set as it is as the predetermined value. In another embodiment, a value obtained by adding a value of 1.0, 1.5, 2.0, 2.5, or 3.0 times the standard deviation to the average value of the measured values may be set as the predetermined value. Alternatively, a value of 0.9, 0.8, 0.7, 0.6, 0.5, 0.4 times or less of the measured values of a marker in samples obtained from multiple healthy individuals (or their average value) may be set as the predetermined value. Thus, in one embodiment of the present method for determining therapeutic effect, a lower expression level of a marker measured in a sample obtained from a patient after the administration of an IL-6 inhibitor (e.g., 0.9, 0.8, 0.7, 0.6, 0.5, 0.4 times or less, preferably less than 0.5 times, and even preferably less than 0.2 times of the control) compared to the expression level of the marker measured in a sample obtained from the patient prior to administration of the IL-6 inhibitor (control sample) indicates that the IL-6 inhibitor has a high therapeutic effect in this patient.

The predetermined value in the present invention may also be set based on the results of clinical trials and such, in which multiple patients suffering from a neutrophil-associated disease were treated with an IL-6 inhibitor. When there are differences in the therapeutic effect of an IL-6 inhibitor between the group of patients in which the measured value of a marker is higher than a baseline value and the group of patients in which the measured value is lower than the baseline value, the baseline value may be used as the predetermined value in the present invention. In such a case, it is preferred that there is a statistically significant difference in therapeutic effect between the two groups. For example, in one embodiment of the present method for predicting therapeutic effect, it is indicated that the therapeutic effect of an IL-6 inhibitor is high for a patient when the expression level of a marker measured in a sample obtained from that patient, suffering from a neutrophil-associated disease, is higher compared with the expression level of the marker measured in sample(s) obtained from another patient(s) suffering from a neutrophil-associated disease for whom therapeutic effect of the IL-6 inhibitor was low. Meanwhile, in one embodiment of the present method for determining therapeutic effect, it is indicated that the therapeutic effect of an IL-6 inhibitor is high for a patient when the expression level of a marker measured in a sample obtained from that patient, suffering from a neutrophil-associated disease, is lower compared to the expression level of the marker measured in sample(s) obtained after administration of the IL-6 inhibitor from another patient(s) suffering from a neutrophil-associated disease for whom therapeutic effect of the IL-6 inhibitor was high.

The measured value and predetermined value of a marker in the present invention implies a measurement result of the expression level of a marker which has been expressed as numeric values in some way, and the value obtained from the measurement (e.g., color development intensity, etc.) may be used as it is, or a positive control sample with a known amount of the contained marker may be separately prepared and a value obtained by converting the measurement result in comparison therewith (e.g., concentration) may be used. Alternatively, the values obtained as described above may be made into scores by separating them into certain ranges (e.g., grades 1, 2, 3) and such values may be used.

Measurement of the expression level of a marker can be performed by selecting an appropriate method depending on the form of the marker or the type of sample in which the expression level of the marker is to be measured. When the form of the marker is a polypeptide, the expression level can be assessed by immunological techniques using antibodies that specifically bind the polypeptide. Immunological techniques may include, for example, enzyme-linked immunosorbent assay (ELISA, EIA), fluorescence immunoassay (FIA), radioimmunoassay (RIA), luminescent immunoassay (LIA), electrochemiluminescence (ECL), Western blotting, surface plasmon resonance, antibody array-based methods, immunohistochemical staining, fluorescence-activated cell sorting (FACS), immunochromatography, immunoprecipitation, immunonephelometry, latex-agglutination, and such.

On the other hand, when the form of the marker is a polynucleotide, it is preferable to perform measurements by genetic engineering techniques using oligonucleotides that specifically bind to the polynucleotide, and such techniques can include, for example, polymerase chain reaction (PCR), reverse-transcription PCR (RT-PCR), real-time quantitative PCR (Q-PCR), Northern blotting, and hybridization (including methods using oligonucleotide arrays such as DNA microarrays).

Measurement of the expression level of a neutrophil-associated gene in the present invention includes both polypeptide measurement and polynucleotide measurement. The expression level of a gene can generally be assessed by quantifying the expression product of the gene. Thus, the polypeptide measured in the present invention can be a protein normally encoded by a gene. A protein can be a protein that underwent posttranslational modification or a fragment of a protein, as long as it can reflect the quantitative level in a biological sample. Meanwhile, when measuring polynucleotides, it is common to measure mRNAs as an expression product of a gene. The expression levels of mRNA can also be compared per cell by correction for the expression level of a housekeeping gene.

A sample in the present invention can be rephrased as a biological sample and refers to an organ, tissue, cell, body fluid, or a mixture thereof contained in a living body. Specific examples may include skin, respiratory tract, intestinal tract, urogenital tract, nerve, tumor, bone marrow, blood cells, blood (whole blood, plasma, serum), lymph, cerebrospinal fluid, intraperitoneal fluid, synovial fluid, intrapulmonary fluid, saliva, sputum, urine, and such. Also included in the samples of the present invention are those obtained by washing them or those obtained by culturing them ex vivo. A preferred sample in the present invention is blood, and a particularly preferred sample is plasma or serum.

Alternatively, when the form of the marker is a polynucleotide, whole blood or blood cell fraction can be used as a sample. From these blood-derived samples, the level of expression of a neutrophil-associated gene in the blood can be determined. Methods of extracting mRNA from whole blood and assessing its expression levels are known. In the present invention, comparison of the expression levels of neutrophil-associated genes in blood is a preferred method for marker evaluation. Thus, in a preferred embodiment of the present invention, neutrophil-associated genes can be used as blood markers.

For example, the PAXgene Blood RNA System (QIAGEN) is a combination of blood collection tubes that stabilize blood RNA after blood collection and a general-purpose kit consisting of columns and such for RNA extraction. The expression levels of neutrophil-associated genes in the blood can be readily assessed by utilizing such commercially available tools for RNA analysis.

In the present invention, samples obtained from patients and such may be processed by methods such as enrichment, refining, extraction, isolation, or physical/chemical treatment before measurement of the expression levels of the markers. For example, blood cells or plasma components may be isolated from a blood sample, and DNA or RNA may be extracted from a tissue/cell sample. Alternatively, unwanted components may be denatured/removed with heating or chemical reagents. Such processing is performed mainly for the purpose of improving the stability of the marker, the sensitivity and specificity of measuring its expression level, and such.

Using the expression level of a neutrophil-associated gene as an indicator, the present invention predicts or determines the therapeutic effect of an IL-6 inhibitor for a neutrophil-associated disease. In the present invention, the "IL-6 inhibitor" is not limited as long as the IL-6 inhibitor is capable of blocking IL-6 signal transduction and inhibiting the biological activity of IL-6. Specific examples of the IL-6 inhibitor can include, but are not limited to, a substance that binds to IL-6, a substance that binds to an IL-6 receptor, and a substance that binds to gp130. Other examples of the IL-6 inhibitor can include, but are not limited to, a substance that inhibits phosphorylation of STAT3, which is important for the intracellular signaling of IL-6, for example, AG490. The IL-6 inhibitor includes, without being particularly limited, an anti-IL-6 antibody, an anti-IL-6 receptor antibody, an anti-gp130 antibody, an IL-6 variant, a soluble IL-6 receptor variant, a partial IL-6 peptide, a partial IL-6 receptor peptide, and a low-molecular weight compound exhibiting activity similar thereto.

Examples of the preferred embodiment of the IL-6 inhibitor can include an IL-6 receptor inhibitor, particularly an anti-IL-6 receptor antibody.

The origin of the antibody used in the present invention is not particularly limited, and the antibody can be derived from preferably a mammal, more preferably a human.

The antibody used in the present invention can be obtained as a polyclonal or monoclonal antibody by use of an approach known in the art. The antibody used in the present invention is particularly preferably a mammal-derived monoclonal antibody. The mammal-derived monoclonal antibody includes an antibody produced by a hybridoma, and an antibody produced by a host transformed with an expression vector containing an antibody gene by a genetic engineering approach. Usually, this antibody blocks the transmission of the biological activity of IL-6 into a cell through its binding to IL-6, an IL-6 receptor, gp130, or the like.

Basically, the monoclonal antibody-producing hybridoma can be prepared by use of a technique known in the art as follows: an IL-6 receptor, IL-6, gp130, or the like is used as a sensitizing antigen in immunization according to an ordinary immunization method, and the resulting immunocytes are fused with parent cells known in the art by an ordinary cell fusion method, and the fused cells are screened for monoclonal antibody-producing cells by an ordinary screening method to prepare monoclonal antibody-producing hybridomas.

Specifically, the monoclonal antibody can be prepared as follows: in the case of preparing, for example, an anti-IL-6 receptor antibody, a human IL-6 receptor or mouse IL-6 receptor to be used as a sensitizing antigen is obtained by using the nucleotide sequence of the IL-6 receptor gene and/or the amino acid sequence of the IL-6 receptor protein disclosed in European Patent Application Publication No. EP 325474 or disclosed in JP-A (Kokai) H3-155795, respectively.

There are two types of IL-6 receptor proteins: a protein expressed on the cell membrane, and a protein dissociated from the cell membrane (soluble IL-6 receptor) (Yasukawa, K. et al., J. Biochem. (1990) 108, 673-676). The soluble IL-6 receptor is constituted by substantially the extracellular region of the IL-6 receptor bound with the cell membrane, and differs from the membrane-bound IL-6 receptor in that the soluble IL-6 receptor lacks the transmembrane region or lacks the transmembrane region and the intracellular region. Any IL-6 receptor may be used as the IL-6 receptor protein as long as the IL-6 receptor may be used as a sensitizing antigen in the preparation of an anti-IL-6 receptor antibody used in the present invention.

The gene sequence of the IL-6 receptor is inserted to an expression vector system known in the art, and appropriate host cells are transformed therewith. Then, the IL-6 receptor protein of interest is purified by a method known in the art from the inside of the host cells or from a culture supernatant thereof. This purified IL-6 receptor protein can be used as the sensitizing antigen. Alternatively, cells expressing the IL-6 receptor or a fusion protein of the IL-6 receptor protein with another protein may be used as the sensitizing antigen.

Likewise, in the case of using IL-6 as a sensitizing antigen in antibody obtainment, human IL-6 is obtained by using the nucleotide sequence of the IL-6 gene and/or the amino acid sequence of the IL-6 protein disclosed in Eur. J. Biochem (1987) 168, 543-550, J. Immunol. (1988)140, 1534-1541, or Agr. Biol. Chem. (1990) 54, 2685-2688. Also, the nucleotide sequence of the gp130 gene and/or the amino acid sequence of the gp130 protein disclosed in EP 411946 can be used as a sensitizing antigen for obtaining an anti-gp130 antibody.

The mammal to be immunized with the sensitizing antigen is not particularly limited and is preferably selected in consideration with compatibility with the parent cells for use in cell fusion. In general, a rodent, for example, a mouse, a rat, or a hamster is used.

The animal is immunized with the sensitizing antigen according to a method known in the art. For example, a general method involves intraperitoneally or subcutaneously injecting the sensitizing antigen to the mammal. Specifically, the sensitizing antigen diluted or suspended in an appropriate volume of phosphate-buffered saline (PBS), saline, or the like is mixed, if desired, with an appropriate amount of a usual adjuvant, for example, a complete Freund's adjuvant.

After emulsification, several shots of the emulsion are each preferably administered to the mammal every 4 to 21 days. Also, an appropriate carrier can be used in the immunization with the sensitizing antigen.

After such immunization and confirmation of a rise in desired antibody level in serum, immunocytes are collected from the mammal and subjected to cell fusion. Preferred examples of the immunocytes that are subjected to cell fusion particularly include spleen cells.

Mammalian myeloma cells for use as partner parent cells to be fused with the immunocytes have already been known in the art, and various cell lines, for example, P3X63Ag8.653 (Kearney, J. F. et al., J. Immunol. (1979) 123, 1548-1550), P3X63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S. J. Exp. Med. (1978) 148, 313-323), and 8210 (Galfre, G. et al., Nature (1979) 277, 131-133) are appropriately used.

Basically, the cell fusion between the immunocytes and the myeloma cells can be carried out according to a method known in the art, for example, the method of Milstein et al. (Kohler. G. and Milstein, C., Methods Enzymol. (1981) 73, 3-46).

More specifically, the cell fusion is carried out, for example, in a usual nutrient medium in the presence of a cell fusion promoter. For example, polyethylene glycol (PEG) or hemagglutinating virus of Japan (HVJ) is used as the fusion promoter. An auxiliary such as dimethyl sulfoxide can be further added thereto and used, if desired, for enhancing fusion efficiency.

The ratio between the immunocytes and the myeloma cells used is preferably set to, for example, 1:1 to 10:1 (immunocytes: myeloma cells). For example, an RPMI1640 medium or a MEM medium suitable for the growth of the myeloma cell lines mentioned above or a usual medium for use in this kind of cell culture can be used in the cell fusion and may be used in combination with a serum supplement such as fetal calf serum (FCS).

For the cell fusion, predetermined amounts of the immunocytes and the myeloma cells are well mixed in the medium. A PEG solution, for example, a solution of PEG having an average molecular weight of about 1000 to 6000, preheated to approximately 37° C. is usually added to the mixture at a concentration of 30 to 60% (w/v) and mixed therewith to form the fusion cells (hybridomas) of interest. Subsequently, the cell fusion agent and the like unfavorable for the growth of the hybridomas can be removed by repeating the operation of sequentially adding an appropriate medium and removing a supernatant by centrifugation.

The hybridomas thus obtained are cultured in a usual selective medium, for example, a HAT medium (medium containing hypoxanthine, aminopterin, and thymidine) for selection. This culture in the HAT medium is continued for a period (usually, several days to several weeks) sufficient for killing cells (non-fused cells) other than the hybridomas of interest. Subsequently, hybridomas producing the antibody of interest are screened for and cloned by an ordinary limiting dilution method.

In addition to obtaining such hybridomas by immunizing a non-human animal with an antigen, a desired human antibody having binding activity against a desired antigen or against cells expressing the antigen may be obtained by sensitizing in vitro human lymphocytes with the desired antigen protein or cells expressing the antigen and fusing the sensitized B lymphocytes with human myeloma cells, for example, with U266 (see JP-A (Kokai) H1-59878). Alternatively, the antigen or cells expressing the antigen may be administered to a transgenic animal having a human antibody gene repertoire, and the desired human antibody can be obtained according to the method mentioned above (see International Patent Application Publication Nos. WO93/12227, WO92/03918, WO94/02602, WO94/25585, WO96/34096, and WO96/33735).

The monoclonal antibody-producing hybridomas thus prepared can be passaged in a usual medium and can also be preserved for a long period in liquid nitrogen.

The monoclonal antibody is obtained from the hybridomas by employing, for example, a method which involves culturing the hybridomas according to an ordinary method and obtaining the antibody as a culture supernatant thereof, or a method which involves administering the hybridomas to mammals compatible therewith and, after growth, obtaining the antibody as ascitic fluid thereof. The former method is suitable for obtaining a highly pure antibody, while the latter method is suitable for the large-scale production of the antibody.

For example, hybridomas producing an anti-IL-6 receptor antibody can be prepared by a method disclosed in JP-A (Kokai) H3-139293. This preparation can be carried out by a method which involves intraperitoneally injecting PM-1 antibody-producing hybridomas to BALB/c mice to obtain ascitic fluid, and purifying the PM-1 antibody from the ascitic fluid, or a method which involves culturing the hybridomas in an appropriate medium, for example, an RPMI1640 medium containing 10% fetal calf serum and 5% BM-Condimed H1 (manufactured by Boehringer Mannheim), a Hybridoma SFM medium (manufactured by Gibco BRL/Life Technologies, Inc.), or a PFHM-II medium (manufactured by Gibco BRL/Life Technologies, Inc.) and purifying the PM-1 antibody from the culture supernatant.

In the present invention, a recombinant antibody produced by use of a gene recombination technique which involves cloning an antibody gene from hybridomas, incorporating the antibody gene into an appropriate vector, and transferring this vector to a host can be used as the monoclonal antibody (see e.g., Borrebaeck C. A. K. and Larrick J. W. THERAPEUTIC MONOCLONAL ANTIBODIES, Published in the United Kingdom by MACMILLAN PUBLISHERS LTD, 1990).

Specifically, mRNAs encoding the variable (V) regions of the antibody are isolated from cells, for example, hybridomas, producing the antibody of interest. For the mRNA isolation, total RNA is prepared by a method known in the art, for example, a guanidine ultracentrifugation method (Chirgwin, J. M. et al., Biochemistry (1979) 18, 5294-5299) or an AGPC method (Chomczynski, P. et al., Anal. Biochem. (1987) 162, 156-159), and the mRNAs are prepared using mRNA Purification Kit (manufactured by Pharmacia Corp.) or the like. Alternatively, the mRNAs can be directly prepared by use of QuickPrep mRNA Purification Kit (manufactured by Pharmacia Corp.).

Antibody V region cDNAs are synthesized from the obtained mRNAs using reverse transcriptase. The cDNA synthesis can be carried out using AMV Reverse Transcriptase First-strand cDNA Synthesis Kit or the like. Also, 5'-Ampli FINDER RACE Kit (manufactured by Clontech Laboratories, Inc.) and a PCR-based 5'-RACE method (Frohman, M. A. et al., Proc. Natl. Acad. Sci. USA (1988) 85, 8998-9002; and Belyaysky, A. et al., Nucleic Acids Res. (1989) 17, 2919-2932) can be used in the cDNA synthesis and amplification. The DNA fragments of interest are purified from the obtained PCR products and ligated with vector DNAs. Recombinant vectors are thereby prepared and transferred to *E. coli* or the like. Colonies are selected, and desired recombinant vectors are prepared. The nucleotide sequences of the DNAs of interest are confirmed by a method known in the art, for example, a deoxy method.

If DNAs encoding the V regions of the antibody of interest are obtained, these DNAs are linked to DNAs encoding constant regions (C regions) of a desired antibody, and these linked DNAs are incorporated into expression vectors. Alternatively, the DNAs encoding the antibody V regions may be incorporated into expression vectors containing the DNAs of the antibody C regions.

For the production of the antibody used in the present invention, the antibody gene is incorporated into an expression vector such that the antibody gene is expressed under the control of expression control regions, for example, an enhancer and a promoter, as mentioned later. Next, host cells are transformed with this expression vector, and the antibody can be expressed.

In the present invention, a recombinant antibody that has been artificially engineered for the purpose of, for example, reducing the heterologous antigenicity against humans, for example, a chimeric antibody or a humanized antibody, can be used. Such an engineered antibody can be produced by use of a known method.

A chimeric antibody is obtained by linking the antibody V region-encoding DNAs obtained as described above to human antibody C region-encoding DNAs, and incorporating the linked DNAs into expression vectors, which are then introduced into a host, followed by production of the antibody (see EP125023 and WO92-19759). A chimeric antibody useful in the present invention can be obtained by use of this known method.

The humanized antibody is also called reshaped human antibody or antibody made into human type antibody, and is obtained by grafting the complementarity-determining regions (CDRs) of a non-human mammalian antibody, for example, a mouse antibody, to the complementarity-determining regions of a human antibody. A general gene recombination approach therefor is also known (see EP125023 and WO92-19759).

Specifically, DNA sequences designed so as to link mouse antibody CDRs and human antibody framework regions (FRs) are synthesized by PCR using several prepared oligonucleotides having overlapping terminal portions. The obtained DNAs are linked to DNAs encoding human antibody C regions. Subsequently, the linked DNAs are incorporated into expression vectors, which are then transferred to a host, followed by the production of the antibody to obtain the humanized antibody (see EP239400 and WO92-19759).

The human antibody FRs to be connected via CDRs are selected such that the complementarity-determining regions form a favorable antigen-binding site. If necessary, amino acids in the framework regions of the antibody variable regions may be substituted such that the complementarity-determining regions of the resulting reshaped human antibody form an appropriate antigen-binding site (Sato, K. et al., Cancer Res. (1993) 53, 851-856).

Usually, human antibody C regions are used for the chimeric antibody or the humanized antibody. Examples of the human antibody heavy chain C region include Cγ. For example, Cγ1, Cγ2, Cγ3, or Cγ4 can be used. Examples of the human antibody light chain C region can include x and X. These human antibody C regions may be modified in order to improve the stability of the antibody or the stability of production thereof.

A chimeric antibody is composed of the variable regions of a non-human mammal-derived antibody and human antibody-derived C regions. A humanized antibody is composed of the complementarity-determining regions of a non-human mammal-derived antibody and human antibody-derived framework regions and C regions. These antibodies exhibit reduced antigenicity in human bodies and as such, are useful as antibodies for use as pharmaceuticals.

Preferable specific examples of the humanized antibody used in the present invention include humanized PM-1 antibodies (see WO92-19759).

In addition to the aforementioned methods for obtaining a human antibody, a technique of obtaining a human antibody by panning using a human antibody library is also known. For example, human antibody variable regions are expressed as a single-chain antibody (scFv) on the surface of phages by a phage display method, and a phage binding to the antigen may be selected. The gene of the selected phage can be analyzed to determine DNA sequences encoding the variable regions of the human antibody binding to the antigen. If the DNA sequence of scFv binding to the antigen is revealed, an appropriate expression vector containing this sequence can be prepared to obtain the human antibody. These methods have already been well known. See WO92/01047, WO92/20791, WO93/06213, WO93/11236, WO93/19172, WO95/01438, and WO95/15388.

The antibody gene constructed as described above can be expressed by a method known in the art. In the case of using mammalian cells, the antibody gene can be expressed by use of a DNA in which a routinely used useful promoter, the antibody gene to be expressed, and a poly-A signal 3'-downstream thereof are functionally linked, or by use of a vector containing the DNA. Examples of the promoter/enhancer can include human cytomegalovirus immediate early promoter/enhancer.

Alternatively, a promoter/enhancer of a virus such as retrovirus, polyoma virus, adenovirus, or simian virus 40 (SV40), a mammalian cell-derived promoter/enhancer such as human elongation factor 1α (HEF1α), or the like can be used as the promoter/enhancer for the antibody expression used in the present invention.

In the case of using, for example, the SV40 promoter/enhancer, the antibody expression can be readily carried out according to the method of Mulligan et al. (Mulligan, R. C. et al., Nature (1979) 277, 108-114). In the case of using the HEF1a promoter/enhancer, the antibody expression can be readily carried out according to the method of Mizushima et al. (Mizushima, S. and Nagata, S. Nucleic Acids Res. (1990) 18, 5322).

In the case of using prokaryotic cells as the host, bacterial cells can be used in the production system. *E. coli* and *Bacillus subtilis* are known as the bacterial cells.

For *E. Coli*, a routinely used useful promoter, a signal sequence for antibody secretion, and the antibody gene to be expressed can be functionally linked and expressed. Examples of the promoter can include lacZ promoter and araB promoter. In the case of using the lacZ promoter, the method of Ward et al. (Ward, E. S. et al., Nature (1989) 341, 544-546; and Ward, E. S. et al. FASEB J. (1992) 6, 2422-2427) can be followed. In the case of using the araB promoter, the method of Better et al. (Better, M. et al. Science (1988) 240, 1041-1043) can be followed.

In the case of production in the periplasm of *E. coli*, pelB signal sequence (Lei, S. P. et al., J. Bacteriol. (1987) 169, 4379-4383) can be used as the signal sequence for antibody secretion. The antibodies produced in the periplasm are separated and then used after appropriate refolding of the antibody structure (see e.g., WO96/30394).

A replication origin derived from SV40, polyoma virus, adenovirus, bovine papillomavirus (BPV), or the like can be used. The expression vector can contain a selective marker such as aminoglycoside phosphotransferase (APH) gene, thymidine kinase (TK) gene, *E. coli* xanthine guanine phosphoribosyltransferase (Ecogpt) gene, or dihydrofolate reductase (dhfr) gene in order to amplify the number of gene copies in the host cell system.

For the production of the antibody used in the present invention, an arbitrary production system can be used. There are in vitro and in vivo production systems for antibody production. Examples of the in vitro production system include a production system using eukaryotic cells and a production system using prokaryotic cells.

In the case of using eukaryotic cells as the host, animal cells, plant cells, or fungal cells can be used in the production system. (1) Mammalian cells, for example, CHO, COS, myeloma, baby hamster kidney (BHK), HeLa, and Vero, (2) amphibian cells, for example, *Xenopus oocytes*, or (3) insect cells, for example, sf9, sf21, and Tn5 are known as the animal cells. *Nicotiana tabacum*-derived cells are known as the plant cells and can be callus-cultured. Yeasts of, for example, the genus *Saccharomyces* (e.g., *Saccharomyces cerevisiae*) or filamentous fungi of, for example, the genus *Aspergillus* (e.g., *Aspergillus niger*) are known as the fungal cells.

The antibody gene of interest is transferred to these cells by transformation, and the transformed cells are cultured in vitro to obtain the antibody. This culture is carried out according to a method known in the art. For example, DMEM, MEM, RPMI1640, or IMDM can be used as a medium and may be used in combination with a serum supplement such as fetal calf serum (FCS). Alternatively, the cells thus harboring the antibody gene may be transferred to the peritoneal cavity or the like of an animal so that the antibody is produced in vivo.

On the other hand, examples of the in vivo production system include a production system using an animal and a production system using a plant. When an animal is used, a mammal, an insect, or the like can be used in the production system.

A goat, a pig, sheep, a mouse, cattle, or the like can be used as the mammal (Vicki Glaser, SPECTRUM Biotechnology Applications, 1993). A silkworm can be used as the insect. In the case of using the plant, for example, tobacco can be used.

The antibody gene is introduced into such an animal or a plant, and the antibody is produced in the body of the animal or the plant and recovered. For example, the antibody gene is prepared as a fusion gene by inserting the gene midway into a gene encoding a protein specifically produced in milk, such as goat β casein. A DNA fragment that contains the fusion gene having the inserted antibody gene is injected into a goat embryo, and this embryo is introduced into a female goat. The desired antibody is obtained from milk produced by a transgenic goat born from the embryo-recipient goat, or progeny thereof. Hormones may be appropriately used for the transgenic goat in order to increase the amount of the milk containing the desired antibody produced by the transgenic goat (Ebert, K. M. et al., Bio/Technology (1994) 12, 699-702).

In the case of using a silkworm, a silkworm is infected with baculovirus having an insert of the antibody gene of interest, and the desired antibody is obtained from the body fluid of this silkworm (Maeda, S. et al., Nature (1985) 315, 592-594). In the case of using tobacco, the antibody gene of interest is inserted to a vector for expression in plants, for example, pMON530, and this vector is introduced into a bacterium such as *Agrobacterium tumefaciens*. Tobacco, for example, *Nicotiana tabacum*, is infected with this bacterium, and the desired antibody is obtained from the leaf of this tobacco (Julian, K.-C. Ma et al., Eur. J. Immunol. (1994)24, 131-138).

In the case of producing an antibody in the in vitro or in vivo production system as mentioned above, an antibody heavy chain (H chain)-encoding DNA and an antibody light chain (L chain)-encoding DNA may be incorporated into separate expression vectors, and the host can be co-transformed with these expression vectors. Alternatively, the H chain-encoding DNA and the L chain-encoding DNA may be incorporated into a single expression vector, and the host can be transformed with this expression vector (see WO94-11523).

The antibody used in the present invention may be a fragment of the antibody or a modified form of the antibody as long as the fragment or the modified form can be suitably used in the present invention. Examples of the antibody fragment include Fab, F(ab')2, Fv, and single-chain Fv (scFv) containing H and L chain Fvs linked through an appropriate linker.

Specifically, the antibody fragment is formed by the treatment of the antibody with an enzyme, for example, papain or pepsin, or is expressed in appropriate host cells after construction of a gene encoding the antibody fragment and subsequent transfer of this gene to an expression vector (see e.g., Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 497-515; Lamoyi, E., Methods in Enzymology (1989) 121, 652-663; Rousseaux, J. et al., Methods in Enzymology (1989) 121, 663-66; and Bird, R. E. et al., TIBTECH (1991) 9, 132-137).

An scFv is obtained by linking the H chain V region and the L chain V region of an antibody. In this scFv, the H chain V region and the L chain V region are linked via a linker, preferably a peptide linker (Huston, J. S. et al., Proc. Natl. Acad. Sci. U.S.A. (1988) 85, 5879-5883). The H chain V region and the L chain V region in the scFv may be derived from any of the above-described antibodies according to the present invention. For example, an arbitrary single-chain peptide composed of 12 to 19 amino acid residues is used as the peptide linker for linking the V regions.

A DNA encoding the scFv is obtained by using a DNA encoding the H chain or the H chain V region of the aforementioned antibody and a DNA encoding the L chain or the L chain V region of the antibody as templates, and amplifying from each of those sequences a DNA portion encoding the desired amino acid sequence by PCR using a primer pair defining the two ends thereof, followed by further amplification using a DNA encoding the peptide linker portion and a primer pair that is designed such that each of the two ends of the peptide linker is linked to the H chain and the L chain, respectively.

Once the scFv-encoding DNA is prepared, an expression vector containing the DNA, and a host transformed with the expression vector can be obtained according to routine methods. Also, the scFv can be obtained according to a routine method using the host.

These antibody fragments can be produced through obtainment and expression of their genes and production by the host in the same way as above. The "antibody" according to the present invention also encompasses these antibody fragments.

Antibodies bound with various molecules such as polyethylene glycol (PEG) may be used as modified forms of antibody. The "antibody" according to the present invention also encompasses these modified forms of the antibody. Such a modified form of the antibody can be obtained by chemical modification of the obtained antibody. These methods have already been established in the art.

The antibody produced and expressed as described above can be separated from the inside or outside of the cells or from the host and purified to homogeneity. The separation and purification of the antibody used in the present invention can be carried out by affinity chromatography. Examples of columns for use in the affinity chromatography include protein A columns and protein G columns. Examples of carriers for use in the protein A columns include Hyper D, POROS, and Sepharose F. F. Any of other ordinary separation and purification methods for use in proteins can be used without limitation.

For example, the antibody used in the present invention can be separated and purified by appropriately selecting or combining chromatography other than the affinity chromatography, filters, ultrafiltration, salting out, and/or dialysis. Examples of the chromatography include ion-exchange chromatography, hydrophobic chromatography, and gel filtration. These chromatography techniques are applicable to high-performance liquid chromatography (HPLC). Alternatively, reverse-phase HPLC may be used.

The concentration of the antibody thus obtained can be measured by, for example, absorbance measurement or ELISA. Specifically, in the case of measuring the concentration by the absorbance measurement, the absorbance is measured at 280 nm after appropriate dilution of the antibody with PBS(−), and the concentration is calculated assuming that 1 mg/ml is 1.35 OD. Alternatively, the concentration can be measured by ELISA as follows: 100 µl of goat anti-human IgG (manufactured by TAG) diluted to 1 µg/ml with a 0.1 M bicarbonate buffer solution (pH 9.6) is added to a 96-well plate (manufactured by Nunc/Thermo Fisher Scientific, Inc.) and incubated overnight at 4° C. to immobilize the antibody thereon. After blocking, 100 µl of an appropriately diluted antibody used in the present invention or a sample containing the antibody, or a preparation human IgG (manufactured by Cappel Laboratories, Inc.) is added thereto and incubated at room temperature for 1 hour.

After washing, 100 µl of alkaline phosphatase-labeled anti-human IgG (manufactured by BioSource International, Inc.) diluted 5000-fold is added thereto and incubated at room temperature for 1 hour. After washing, a substrate solution is added thereto and incubated. Then, the absorbance is measured at 405 nm using MICROPLATE READER Model 3550 (manufactured by Bio-Rad Laboratories, Inc.) to calculate the concentration of the antibody of interest.

Specific examples of the anti-IL-6 antibody can include, but are not particularly limited to, MH166 (Matsuda, T. et al., Eur. J. Immunol. (1998) 18, 951-956) and SK2 antibody (Sato K et al., Academic proceedings of the 21st General Meeting of the Japanese Society for Immunology (1991) 21, 166).

Specific examples of the anti-IL-6 receptor antibody include, but are not particularly limited to, MR16-1 antibody (Tamura, T. et al. Proc. Natl. Acad. Sci. USA (1993) 90, 11924-11928), PM-1 antibody (Hirata, Y. et al., J. Immunol. (1989) 143, 2900-2906), AUK12-20 antibody, AUK64-7 antibody, and AUK146-15 antibody (WO92-19759).

Among them, preferred examples of the monoclonal antibody against the human IL-6 receptor include, but are not limited to, the PM-1 antibody, and preferred examples of the monoclonal antibody against the mouse IL-6 receptor include, but are not limited to, the MR16-1 antibody. Preferred examples of the humanized anti-IL-6 receptor antibody can include, but are not limited to, an antibody comprising a heavy chain variable region having the sequence of SEQ ID NO: 19 and a light chain variable region having the sequence of SEQ ID NO: 20, an antibody comprising a heavy chain having the sequence of SEQ ID NO: 21 and a light chain having the sequence of SEQ ID NO: 22, a humanized PM-1 antibody (Tocilizumab, MRA), and SA237. Other preferred examples of the humanized anti-IL-6 receptor antibody can include, but are not limited to, antibodies described in WO2009/041621 and WO2010/035769. Examples of other preferred embodiments of the anti-IL-6 receptor antibody can include, but are not limited to, an anti-IL-6 receptor antibody that recognizes the same epitope as that recognized by the humanized PM-1 antibody (Tocilizumab, MRA) and an anti-IL-6 receptor antibody that recognizes the same epitope as that recognized by SA237.

Specific examples of the anti-gp130 antibody include, but are not particularly limited to, AM64 antibody (JP-A (Kokai) H3-219894), 4B11 antibody, 2H4 antibody (U.S. Pat. No. 5,571,513), and B-P8 antibody (JP-A (Kokai) H8-291199).

The IL-6 variant used in the present invention is a substance that has binding activity with the IL-6 receptor and does not transduce the biological activity of IL-6. Thus, the IL-6 variant blocks the signal transduction of IL-6 because it competes with IL-6 for binding to the IL-6 receptor but does not transduce the biological activity of IL-6.

An IL-6 variant is prepared by introducing mutations into IL-6 through substitution of amino acid residues in the amino acid sequence of IL-6. The origin of IL-6 on which the IL-6 variant is based is not limited and is preferably human IL-6 in consideration of antigenicity, etc. Specifically, the secondary structure of the amino acid sequence of IL-6 is predicted by use of a molecular modeling program known in the art, for example, WHATIF (Vriend et al., J. Mol. Graphics (1990) 8, 52-56), and the influence of amino acid residues to be substituted on the whole structure is evaluated. After determination of appropriate amino acid residues to be substituted, a vector containing a nucleotide sequence encoding the human IL-6 gene is used as a template, and a conventional PCR method is performed to introduce mutations such that the amino acids are substituted, and thereby a gene encoding the IL-6 variant is obtained. This gene is incorporated into an appropriate expression vector according to the need, and the IL-6 variant can be obtained according to the aforementioned expression, production, and purification methods for the recombinant antibody.

Specific examples of the IL-6 variant can include IL-6 variants disclosed in Brakenhoff et al., J. Biol. Chem. (1994) 269, 86-93, Savino et al., EMBO J. (1994) 13, 1357-1367, WO96-18648, and WO96-17869.

A partial IL-6 receptor peptide is a peptide having a portion or the whole of the amino acid sequence of a region involved in the binding of the IL-6 receptor to IL-6 in the amino acid sequence of the IL-6 receptor. Such a peptide is composed of usually 10 to 80, preferably 20 to 50, more preferably 20 to 40 amino acid residues.

The partial IL-6 receptor peptide can be prepared by identifying the region involved in the binding of the IL-6 receptor to IL-6 in the amino acid sequence of the IL-6 receptor and producing the peptide by a conventionally known method, for example, a genetic engineering approach or a peptide synthesis method on the basis of a portion or the whole of the amino acid sequence of the identified region.

For the preparation of the partial IL-6 receptor peptide by the genetic engineering approach, a DNA sequence encoding the desired peptide is incorporated into an expression vector, and the partial IL-6 receptor peptide can be obtained according to the aforementioned expression, production, and purification methods for the recombinant antibody.

For the preparation of the partial IL-6 receptor peptide by the peptide synthesis method, a method conventionally used in peptide synthesis, for example, a solid-phase synthesis method or a liquid-phase synthesis method can be used.

Specifically, the peptide synthesis can be carried out according to methods described in Zoku Iyakuhin no Kaihatsu (Development of Pharmaceuticals, Second Series, in English), Vol. 14, Peptide Synthesis, edited by Haruaki Yajima, Hirokawa Shoten Co., Ltd. (1991). The solid-phase synthesis method used is a method which involves, for example, coupling an amino acid corresponding to the C terminus of a peptide to be synthesized to a support insoluble in an organic solvent, and elongating a peptide chain by alternately repeating the reaction of condensing one amino acid at a time (its $\alpha$-amino group and side chain functional groups have been protected with appropriate protective groups) in a direction from the C terminus toward the N terminus and the reaction of eliminating the protective group of the $\alpha$-amino group of the amino acid or peptide bound onto the resin. The solid-phase peptide synthesis method is broadly divided into Boc and Fmoc methods depending on the types of the protective groups used.

After such synthesis of the peptide of interest, deprotection reaction and cleavage reaction of the peptide chain from the support are carried out. In the cleavage reaction of the peptide chain, usually, hydrogen fluoride or trifluoromethanesulfonic acid can be used for the Boc method, and TFA can be used for the Fmoc method. In the Boc method, the protected peptide resin is treated, for example, in the presence of anisole in hydrogen fluoride. Subsequently, protective group elimination and cleavage from the support are carried out to recover the peptide. This peptide is freeze-dried to obtain a crude peptide. On the other hand, in the Fmoc method, for example, deprotection reaction and cleavage reaction of the peptide chain from the support can be carried out by the same operation as above in TFA.

The obtained crude peptide can be separated and purified by application to HPLC. The peptide can be eluted under the optimum conditions by use of a water-acetonitrile mixed solvent conventionally used in protein purification. A fraction corresponding to a peak in the obtained profile of chromatography is separated and then freeze-dried. The peptide fraction thus purified is identified by, for example, mass spectrometric molecular weight analysis, amino acid composition analysis, or amino acid sequence analysis.

The present invention also relates to an agent for treating neutrophil-associated diseases with high expression level of a neutrophil-associated gene comprising an IL-6 inhibitor as an active ingredient. The "neutrophil-associated diseases with high expression level of a neutrophil-associated gene" herein preferably refers to neutrophil-associated diseases in which the expression level of a neutrophil-associated gene is high prior to administration of an IL-6 inhibitor, but the expression level of a neutrophil-associated gene is reduced following administration compared to before administration of the IL-6 inhibitor.

In the present invention, the phrase "comprising as an active ingredient" means comprising an IL-6 inhibitor as at least one of the active ingredients and does not limit the content percentage thereof. The therapeutic agent of the present invention may also contain active ingredients other than the IL-6 inhibitor. The therapeutic agent of the present invention may be used not only for therapeutic purposes but for preventive purposes.

The therapeutic agent of the present invention can be formulated according to a routine method (e.g., Remington's Pharmaceutical Science, latest edition, Mark Publishing Company, Easton, U.S.A). The therapeutic agent of the present invention may contain a pharmaceutically acceptable carrier and/or additive according to needs. The therapeutic agent of the present invention can contain, for example, a surfactant (PEG, Tween, etc.), an excipient, an antioxidant (ascorbic acid, etc.), a colorant, a flavoring agent, a preservative, a stabilizer, a buffer (phosphate, citrate, other organic acids, etc.), a chelating agent (EDTA, etc.), a suspending agent, a tonicity agent, a binder, a disintegrant, a lubricant, a flowability enhancer, and a corrigent. However, the therapeutic agent of the present invention may appropriately contain, without being limited to the above agents, other carriers routinely used. Specific examples thereof can include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium-chain fatty acid triglyceride, polyoxyethylene hydrogenated castor oil 60, white soft sugar, carboxymethylcellulose, corn starch, and inorganic salts. Also, the therapeutic agent of the present invention may contain other low-molecular-weight polypeptides, proteins (e.g., serum albumin, gelatin, and immunoglobulin), and amino acids. In the case of preparing an aqueous solution for injection, the IL-6 inhibitor is dissolved in, for example, an isotonic solution containing saline, glucose, or other adjuvants. Examples of the adjuvants include D-sorbitol, D-mannose, D-mannitol, and sodium chloride. The solution may be further used in combination with an appropriate solubilizer, for example, an alcohol (ethanol, etc.), a polyalcohol (propylene glycol, PEG, etc.), or a nonionic surfactant (polysorbate 80 or HCO-50).

The IL-6 inhibitor may be enclosed in a microcapsule (microcapsule made of hydroxymethylcellulose, gelatin, poly[methyl methacrylate], or the like) or prepared into a colloid drug delivery system (liposomes, albumin microspheres, microemulsions, nanoparticles, and nanocapsules, etc.) (see e.g., Remington's Pharmaceutical Science 16th edition & Oslo Ed. (1980)). Methods for formulating drugs as sustained-release drugs are also known in the art and may be applied to the IL-6 inhibitor of the present invention (Langer et al., J. Biomed. Mater. Res. (1981) 15: 167-277; Langer, Chem. Tech. (1982) 12: 98-105; U.S. Pat. No. 3,773,919; EP 58,481; Sidman et al., Biopolymers (1983) 22: 547-56; and EP 133,988). In addition, the therapeutic agent of the present invention may be supplemented or mixed with hyaluronidase to allow an increased amount of fluid to be subcutaneously administered (e.g., WO2004/078140).

The therapeutic agent of the present invention can be administered through any of oral and parenteral routes and is preferably administered parenterally. Specifically, the therapeutic agent of the present invention is administered to a patient through injection or percutaneous administration. Examples of the dosage form of the injection include systemic or local administration by intravenous injection, intramuscular injection, intraperitoneal injection, subcutaneous injection, or such. The therapeutic agent of the present invention may be injected locally, particularly, intramuscularly, to a treatment site or the neighborhood thereof. Examples of the dosage form of the percutaneous administration include ointments, gels, creams, poultices, and patches, which permit systemic or local administration. The administration method can be appropriately selected according to the age and symptoms of a patient. The dose can be selected, for example, within the range of 0.0001 mg to 100 mg of the active ingredient per kg of body weight per dose. Alternatively, for example, when administering to a human patient, the range of 0.001 to 1000 mg/kg body weight of the active ingredient per patient can be selected. The single dose preferably contains, for example, approximately 0.01 to 50 mg/kg body weight of the antibody of the present invention. However, the therapeutic agent of the present invention is not limited by these doses.

The therapeutic agent of the present invention can be used alone for treating neutrophil-associated diseases with high expression levels of neutrophil-associated genes in humans and animals. Alternatively, the therapeutic agent of the present invention can be administered orally as a mixture with other ingredients that may be commonly used in pharmaceuticals and foods. The therapeutic agent of the present invention can also be used in combination with other compounds, microbes, or the like known to have therapeutic and/or preventive effect on neutrophil-associated diseases.

The present invention also relates to a method for treating neutrophil-associated diseases in a subject having high levels of expression of neutrophil-associated genes, which comprises administering an IL-6 inhibitor to the subject. Subjects to which an IL-6 inhibitor is administered include mammals. Mammals include humans and non-human mammals in need of treatment or prevention of a neutrophil-associated disease, preferably humans and monkeys, and more preferably humans.

The present invention also relates to an IL-6 inhibitor for use in the treatment of neutrophil-associated diseases with high expression levels of neutrophil-associated genes. Alternatively, the present invention relates to the use of an IL-6 inhibitor in the manufacture of an agent for treating neutrophil-associated diseases with high expression levels of neutrophil-associated genes.

The present invention also relates to a method for manufacturing an agent for treating neutrophil-associated diseases with high expression levels of neutrophil-associated genes, comprising mixing an IL-6 inhibitor with a pharmaceutically acceptable carrier. All prior art documents cited herein are incorporated herein by reference.

Examples

Next, the present invention will be described more specifically with examples; however, the present invention is not limited to the examples below.

As described below, the present inventors analyzed by DNA microarray, genes that normalized in neuromyelitis optica (NMO) patients after administration of tocilizumab (TCZ).

Gene Expression Assay

Among NMO patients who received TCZ by intravenous injection once every four weeks at 8 mg/kg each time, seven patients with improved NMO were subject to collection of peripheral blood into the PAXgene blood RNA tubes (PreAnalytiX GmBH) prior to and twelve months after the administration of the first TCZ treatment. Peripheral blood was collected during the day. From the peripheral blood, mRNA was extracted using the PAXgene Blood miRNA spin-column (QIAGEN). From the mRNA, the cDNA was synthesized by One-Color Microarray-Based Gene Expression Analysis (Agilent Technologies), ver. 6.5. 600 ng of cDNA was hybridized with the SurePrint G3 Human GE microarray (Agilent Technologies), ver. 2.0 for 17 hours, washed, and scanned using the Aglient DNA microarray scanner. Scanned image data were quantified using Feature Extraction, ver. 10.7.1.1 software (Agilent Technologies). Data were normalized using the GeneSpring GX 12.0 software (Agilent Technologies). Changes in the expression ratio were analyzed by paired t-test. The expression ratios and variations in gene probes were extracted using the Excel 2013 software. Probes meeting one of the following two criteria were extracted: (1) expression ratio greater than or equal to 1.5 or less than or equal to 0.67, $p<0.05$; and (2) expression ratio greater than 1 and less than 1.5, or greater than 0.67 and less than 1, $p<0.01$. Extracted probes were analyzed online using DAVID 6.8 (Reference: Huang D W, Sherman B T, and Lempicki R A. Systematic and integrative analysis of large gene lists using DAVID bioinformatics resources. Nat Protoc. 4; 44-57 (2009)).

Improvements in NMO were determined based on a decrease in the number of relapses per year, a decrease in the subjective symptoms of pain and fatigue, and a decrease in the number of EDSS (Expanded Disability Status Scale).

Results

The results of the above analysis are shown in FIG. 1. Gene expressions in the NMO patients and non-NMO patients (controls) were analyzed by DNA microarray using a total number of 50599 probes, showing upregulation of 2219 probes and downregulation of 1890 probes in NMO patients compared to the controls. Also, 71 probes were upregulated and 224 probes were downregulated in patients after TCZ treatment compared with before TCZ treatment. Among the 2175 probes having high expression levels in NMO patients before TCZ treatment, 41 were downregulated after TCZ treatment.

Among the probes that were significantly different from the controls, examples of probes that were downregulated in NMO patients one year after TCZ treatment are shown in Table 1. Table 1 shows probes with a ratio of expression before and after TCZ treatment of less than 0.5, starting from those with greatly reduced expression ratios. Surprisingly, top nine of these genes are those associated with the granule content of neutrophils. These neutrophil-associated genes may be useful as markers for predicting or determining the therapeutic effect of IL-6 inhibitors in neutrophil-associated diseases, since they are genes with significantly higher expression levels in NMO patients and greatly reduced expression levels after TCZ-treatment.

Besides IL-6, neutrophils have been reported to be associated with the disease state of neuromyelitis optica (Non-Patent Documents 3 and 4). In addition to neuromyelitis optica, Neuro-Sweet disease, stroke, cerebral infarction and such are known as diseases in which IL-6 and neutrophil are associated with their pathological conditions (Clinical Neurology 2012; 52:1234-1236). It is believed that for these diseases also, the therapeutic effect of IL-6 inhibitors can be predicted or determined by measuring the expression levels of neutrophil-associated genes in patients.

TABLE 1

| Probe Name | Gene Symbol | Gene Name | Description | Expression ratio (NMO post/ NMO pre) | Expression ratio (NMO pre/control) |
|---|---|---|---|---|---|
| A_23_P140384 | CTSG | cathepsin G | Homo sapiens cathepsin G (CTSG), mRNA [NM_001911] | 0.102 | 11.566 |
| A_23_P326080 | DEFA4 | defensin, alpha 4, corticostatin | Homo sapiens defensin, alpha 4, corticostatin (DEFA4), mRNA [NM_001925] | 0.139 | 14.410 |
| A_33_P3279353 | AZU1 | azurocidin 1 | Homo sapiens azurocidin, 1 (AZU1), mRNA [NM_001700] | 0.143 | 9.705 |
| A_23_P131785 | BPI | bactericidal/ permeability-increasing protein | Homo sapiens bactericidal/permeability-increasing protein (BPI), mRNA [NM_001725] | 0.144 | 5.567 |
| A_23_P130961 | ELANE | elastase, neutrophil expressed | Homo sapiens elastase, neutrophil expressed (ELANE), mRNA [NM_001972] | 0.147 | 12.664 |
| A_23_P166848 | LTF | lactotransferrin | Homo sapiens lactotransferrin (LTF), transcript variant 1, mRNA [NM_002343] | 0.223 | 5.936 |
| A_23_P31816 | DEFA3 | defensin, alpha 3, neutrophil-specific | Homo sapiens defensin, aplpha 3, neutrophil-specific (DEFA3), mRNA [NM_005217] | 0.276 | 7.789 |
| A_23_P169437 | LCN2 | lipocalin 2 | Homo sapiens lipocalin 2 (LCN2), mRNA [NM_005564] | 0.277 | 5.934 |
| A_23_P253791 | CAMP | cathelicidin antimicrobial peptide | Homo sapiens cathelicidin antimicrobial peptide (CAMP), mRNA [NM_004345] | 0.319 | 9.094 |

PCR-Analysis of Blood cDNA

TCZ was administered by intravenous injection at 8 mg/kg once every four weeks; and for seven patients with improved NMO, whole blood was collected into the PAXgene RNA blood collection tubes (PreAnalytiX GmBH) and the whole blood mRNA was extracted on the PAXgene Blood miRNA Spin Column (QIAGEN). The PrimeScript RT-PCR Kit (TaKaRa) was used to synthesize cDNA from the extracted mRNA. The SYBER Ex Taq assay was used for RT-PCR, and reactions were monitored with the Light-Cycler 96 system (Roche). Commercial sets (Quantitect Primer Assay, AIAGEN) were used for the respective primers for amplification below with (3-actin (ACTB) as a control:

```
Hs_CTSG_1_SG
QuantiTect Primer Assay (200) QT00051667 QIAGEN

Hs_LTF_2_SG
QuantiTect Primer Assay (200) QT01677879 QIAGEN

Hs_AZU1_1_SG
QuantiTect Primer Assay (200) QT00012327 QIAGEN

Hs_BPI_1_SG
QuantiTect Primer Assay (200) QT00096649 QIAGEN

Hs_DEFA4_1_SG
QuantiTect Primer Assay (200) QT00001603 QIAGEN

β-actin
                                 (SEQ ID NO: 23)
Forward CACTCTTCCAGCCTTCCTTCC (SEQ ID NO: 24)
Reverse GCGTACAGGTCTTTGCGGATG
```

Whole blood was collected before and one year after TCZ administration. Improvements in NMO were determined based on a decrease in the number of relapses per year, a decrease in the subjective symptoms of pain and fatigue, and a decrease in the number of EDSS (Expanded Disability Status Scale).

Statistical Analysis

Wilcoxon's signed rank sum test was carried out to compare the NMO group data before and after TCZ-treatment using the Prism software. The Mann-Whitney test was used to compare the NMO and control groups. A p value less than 0.05 was considered to be significantly different.

Figure 2:
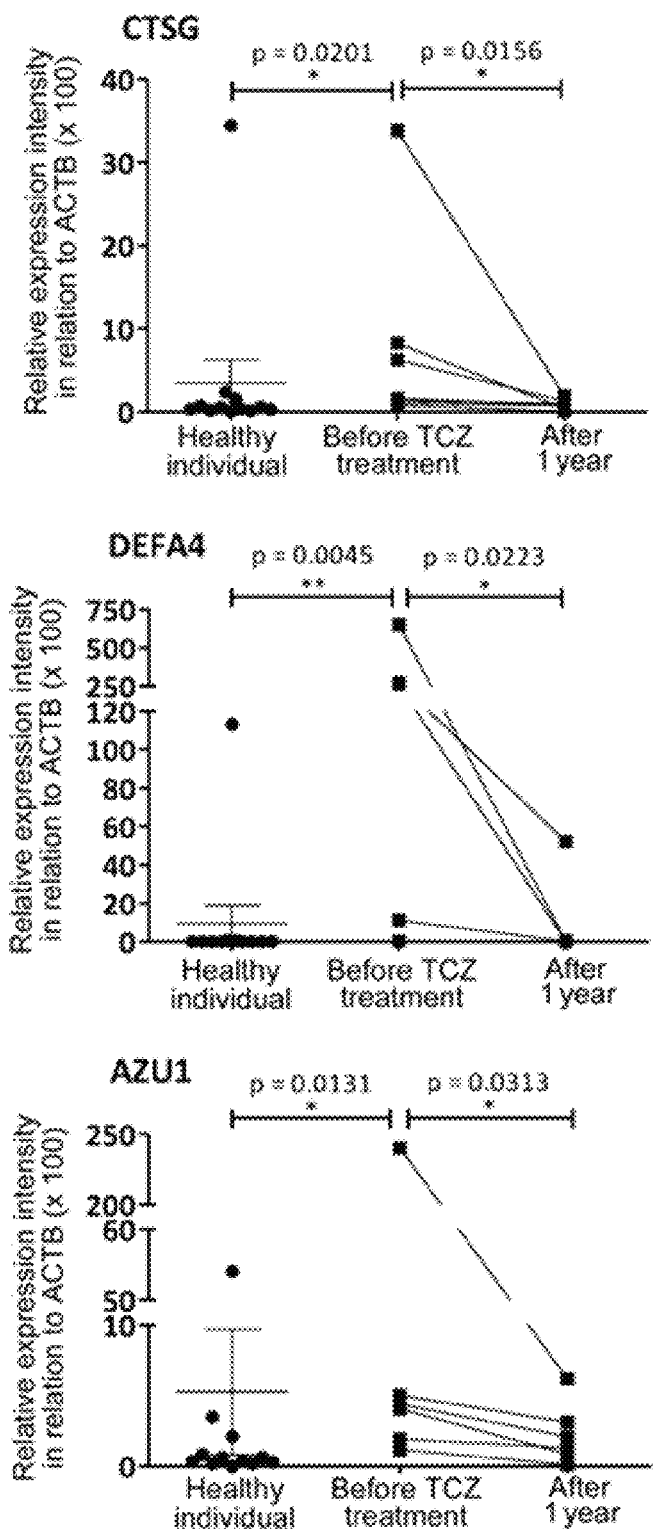
FIG. 2 shows RT-PCR results confirming the whole blood mRNA levels of CTSG, DEFA4, and AZU1 in NMO patients before and after TCZ treatment. The vertical axis shows the relative expression intensity in relation to the expression level of ACTB.

Some of the microarray-based analysis results verified by RT-PCR of the whole blood cDNA are shown in FIG. 2. The top three genes (CTSG, DEFA4, and AZU1) for which significant decreases in the expression levels were observed in the microarray analysis of NMO patients one year after TCZ treatment had a similarly decreasing trend in the expression level by RT-PCR analysis, and this supports the microarray analysis results. On the other hand, such changes in the expression level were not observed in healthy individuals (HC).

INDUSTRIAL APPLICABILITY

The present invention provides methods for predicting the effect of an IL-6 inhibitor in treating IL-6- and neutrophil-associated diseases by using the expression levels of neutrophil-associated genes of patients with the disease as an indicator. The present invention further provides novel methods for treating patients with IL-6- and neutrophil-associated diseases whose expression levels of neutrophil- -associated genes are high. By the present invention, administration of an IL-6 inhibitor to patients for whom therapeutic effect by an IL-6 inhibitor cannot be expected or who will be forced to experience serious side effects or worsening of concomitant immunological abnormalities can be avoided, and appropriate therapeutic methods can be selected.

The invention claimed is:

1. A method for treating the IL-6 associated disease neuromyelitis optica, comprising administering an anti-IL-6 receptor antibody to a patient having neuromyelitis optica, wherein a sample obtained from the patient prior to the administration is determined to have a high expression level of CTSG (cathepsin G) compared to the expression level of CTSG in a sample obtained from a healthy individual, wherein the administered anti-IL-6 receptor antibody is selected from MR16-1, PM-1, humanized PM-1 (Tocilizumab), AUK-12-20, AUK64-7, AUK-146-15 and SA237, wherein the anti-IL-6 receptor antibody is administered to the patient via systemic administration, and further wherein the sample obtained from the patient is a peripheral blood sample.

2. A method for treating the IL-6 associated disease neuromyelitis optica comprising administering an anti-IL-6 receptor antibody selected from MR16-1, PM-1, humanized PM-1 (Tocilizumab), AUK-12-20, AUK64-7, AUK-146-15 and SA237, to a patient for whom prior treatment of the IL-6 inhibitor has been determined to be highly effective,
   wherein the prior treatment is determined to be highly effective by:
      (i) measuring the expression level of CTSG (cathepsin G) in a sample obtained from the patient with neuromyelitis optica who has been administered the anti-IL-6 receptor antibody, and
      (ii) comparing the expression level measured in (i) with the expression level of CTSG in a sample obtained from the patient prior to administration of the anti-IL-6 receptor antibody, wherein the therapeutic effect of the IL-6 inhibitor is indicated to be high when the expression level of CTSG is lower than the expression level of CTSG in a sample obtained from the patient prior to administration of the anti-IL-6 receptor antibody
   wherein the anti-IL-6 receptor antibody is administered to the patient via systemic administration, and further wherein the sample obtained from the patient is a peripheral blood sample.

3. The method of claim 1, wherein the anti-IL-6 receptor antibody is a humanized antibody.

4. The method of claim 1, wherein the determined expression level of CTSG is five times or higher, or ten times or higher, than the expression level of CTSG in the sample obtained from a healthy individual.

5. The method of claim 2, wherein the anti-IL-6 receptor antibody is a chimeric antibody, a humanized antibody, or a human antibody.

6. The method of claim 2, wherein the measured expression level of CTSG in (i) is less than 0.5 times or less than 0.2 times the expression level of CTSG in the sample obtained from the patient before the prior administration of the anti-IL-6 receptor antibody.

7. A method for treating the IL-6 associated disease neuromyelitis optica, comprising administering an anti-IL-6 receptor antibody selected from MR16-1, PM-1, humanized PM-1 (Tocilizumab), AUK-12-20, AUK64-7, AUK-146-15 and SA237, to a patient for whom treatment with an IL-6 inhibitor is predicted to be highly effective, wherein the treatment is predicted to be highly effective by:
   (i) measuring the expression level of CTSG in a sample obtained from the patient with neuromyelitis optica, and
   (ii) comparing the expression level measured in (i) with the expression level of CTSG in a sample obtained from a healthy individual, wherein the therapeutic effect of the IL-6 inhibitor is indicated to be high when the expression level of CTSG is higher than the expression level of CTSG in the sample obtained from a healthy individual wherein the anti-IL-6 receptor antibody is administered to the patient via systemic administration, and further wherein the sample obtained from the patient is a peripheral blood sample.

8. The method of claim 7, wherein the anti-IL-6 receptor antibody is a chimeric antibody, a humanized antibody, or a human antibody.

9. The method of claim 7, wherein the measured expression level of CTSG is five times or higher, or ten times or higher, than the expression level of CTSG in the sample obtained from the healthy individual.

10. The method of claim 1, wherein the administered anti-IL-6 receptor antibody is MR16-1.

11. The method of claim 1, wherein the administered anti-IL-6 receptor antibody is PM-1.

12. The method of claim 1, wherein the administered anti-IL-6 receptor antibody is humanized PM-1 (Tocilizumab).

13. The method of claim 1, wherein the administered anti-IL-6 receptor antibody is AUK-12-20.

14. The method of claim 1, wherein the administered anti-IL-6 receptor antibody is AUK64-7.

15. The method of claim 1, wherein the administered anti-IL-6 receptor antibody is AUK-146-15.

16. The method of claim 1, wherein the administered anti-IL-6 receptor antibody is SA237.

* * * * *

```
                              SEQUENCE LISTING

<160> NUMBER OF SEQ ID NOS: 24

<210> SEQ ID NO 1
<211> LENGTH: 924
<212> TYPE: DNA
<213> ORGANISM: Homo sapiens

<400> SEQUENCE: 1
gcacagcagc aactgactgg gcagcctttc aggaaagatg cagccactcc tgcttctgct     60
ggcctttctc ctacccactg gggctgaggc aggggagatc atcggaggcc gggagagcag    120
gccccactcc cgcccctaca tggcgtatct tcagatccag agtccagcag gtcagagcag    180
atgtggaggg ttcctggtgc gagaagactt tgtgctgaca gcagctcatt gctggggaag    240
caatataaat gtcaccctgg gcgcccacaa tatccagaga cgggaaaaca cccagcaaca    300
catcactgcg cgcagagcca tccgccaccc tcaatataat cagcggacca tccagaatga    360
catcatgtta ttgcagctga gcagaagagt cagacggaat cgaaacgtga acccagtggc    420
tctgcctaga gcccaggagg gactgagacc cgggacgctg tgcactgtgg ccggctgggg    480
cagggtcagc atgaggaggg gaacagatac actccgagag gtgcagctga gagtgcagag    540
ggataggcag tgcctccgca tcttcggttc ctacgacccc gaaggcagat ttgtgtggg    600 ggaccggcgg gaacggaagg ctgccttcaa gggggattcc ggaggccccc tgctgtgtaa    660
caatgtggcc cacggcatcg tctcctatgg aaagtcgtca ggggttcctc cagaagtctt    720
caccagggtc tcaagtttcc tgccctggat aaggacaaca atgagaagct tcaaactgct    780
ggatcagatg gagaccccc tgtgactgac tcttcttctc ggggacacag gccagctcca    840
cagtgttgcc agagccttaa taaacgtcca cagagtataa ataaccaatt cctcatttgt    900
tcattaaacg tcattcagta ctta                                           924

<210> SEQ ID NO 2
<211> LENGTH: 255
<212> TYPE: PRT
<213> ORGANISM: Homo sapiens

<400> SEQUENCE: 2

Met Gln Pro Leu Leu Leu Leu Ala Phe Leu Leu Pro Thr Gly Ala
1               5                   10                  15

Glu Ala Gly Glu Ile Ile Gly Gly Arg Glu Ser Arg Pro His Ser Arg
            20                  25                  30

Pro Tyr Met Ala Tyr Leu Gln Ile Gln Ser Pro Ala Gly Gln Ser Arg
        35                  40                  45

Cys Gly Gly Phe Leu Val Arg Glu Asp Phe Val Leu Thr Ala Ala His
    50                  55                  60

Cys Trp Gly Ser Asn Ile Asn Val Thr Leu Gly Ala His Asn Ile Gln
65                  70                  75                  80

Arg Arg Glu Asn Thr Gln Gln His Ile Thr Ala Arg Arg Ala Ile Arg
                85                  90                  95

His Pro Gln Tyr Asn Gln Arg Thr Ile Gln Asn Asp Ile Met Leu Leu
            100                 105                 110

Gln Leu Ser Arg Arg Val Arg Arg Asn Arg Asn Val Asn Pro Val Ala
        115                 120                 125
```

Leu Pro Arg Ala Gln Glu Gly Leu Arg Pro Gly Thr Leu Cys Thr Val
                130                 135                 140

Ala Gly Trp Gly Arg Val Ser Met Arg Gly Thr Asp Thr Leu Arg
145                 150                 155                 160

Glu Val Gln Leu Arg Val Gln Arg Asp Arg Gln Cys Leu Arg Ile Phe
                165                 170                 175

Gly Ser Tyr Asp Pro Arg Arg Gln Ile Cys Val Gly Asp Arg Glu
                180                 185                 190

Arg Lys Ala Ala Phe Lys Gly Asp Ser Gly Gly Pro Leu Leu Cys Asn
                195                 200                 205

Asn Val Ala His Gly Ile Val Ser Tyr Gly Lys Ser Ser Gly Val Pro
210                 215                 220

Pro Glu Val Phe Thr Arg Val Ser Ser Phe Leu Pro Trp Ile Arg Thr
225                 230                 235                 240

Thr Met Arg Ser Phe Lys Leu Leu Asp Gln Met Glu Thr Pro Leu
                245                 250                 255

<210> SEQ ID NO 3
<211> LENGTH: 619
<212> TYPE: DNA
<213> ORGANISM: Homo sapiens

<400> SEQUENCE: 3
ccttaaataa ggaagtcctc tcctctgtgt gcatggctgc tcttgctaca taagacctgg      60
aacacaggac tgctgtctgc cctctctgct cgccctgcct agcttgagga tctgtcaccc     120
cagccatgag gattatcgcc ctcctcgctg ctattctctt ggtagccctc caggtccggg     180
caggcccact ccaggcaaga ggtgatgagg ctccaggcca ggagcagcgt gggccagaag     240
accaggacat atctatttcc tttgcatggg ataaaagctc tgctcttcag gtttcaggct     300
caacaagggg catggtctgc tcttgcagat tagtattctg ccggcgaaca gaacttcgtg     360
ttgggaactg cctcattggt ggtgtgagtt tcacatactg ctgcacgcgt gtcgattaac     420
gttctgctgt ccaagagaat gtcatgctgg gaacgccatc atcggtggtg ttagcttcac     480
atgcttctgc agctgagctt gcagaataga gaaaaatgag ctcataattt gctttgagag     540
ctacaggaaa tggttgtttc tcctatactt tgtccttaac atctttcttg atcctaaata     600
tatatctcgt aacaagatg                                                  619

<210> SEQ ID NO 4
<211> LENGTH: 97
<212> TYPE: PRT
<213> ORGANISM: Homo sapiens

<400> SEQUENCE: 4

Met Arg Ile Ile Ala Leu Leu Ala Ala Ile Leu Leu Val Ala Leu Gln
1               5                   10                  15

Val Arg Ala Gly Pro Leu Gln Ala Arg Gly Asp Glu Ala Pro Gly Gln
                20                  25                  30

Glu Gln Arg Gly Pro Glu Asp Gln Asp Ile Ser Ile Ser Phe Ala Trp
            35                  40                  45

Asp Lys Ser Ser Ala Leu Gln Val Ser Gly Ser Thr Arg Gly Met Val
        50                  55                  60

Cys Ser Cys Arg Leu Val Phe Cys Arg Arg Thr Glu Leu Arg Val Gly
65                  70                  75                  80

Asn Cys Leu Ile Gly Gly Val Ser Phe Thr Tyr Cys Cys Thr Arg Val
                85                  90                  95

Asp

<210> SEQ ID NO 5
<211> LENGTH: 936
<212> TYPE: DNA
<213> ORGANISM: Homo sapiens

<400> SEQUENCE: 5

```
tagccacaga cctgccccgc catgacccgg ctgacagtcc tggccctgct ggctggtctg      60
ctggcgtcct cgagggccgg ctccagcccc cttttggaca tcgttggcgg ccggaaggcg     120
aggccccgcc agttcccgtt cctggcctcc attcagaatc aaggcaggca cttctgcggg     180
ggtgccctga tccatgcccg cttcgtgatg accgcggcca gctgcttcca aagccagaac     240
cccggggtta gcaccgtggt gctgggtgcc tatgacctga gcggcgggag gaggcagtcc     300
cgccagacgt tttccatcag cagcatgagc gagaatggct acgaccccca gcagaacctg     360
aacgacctga tgctgcttca gctggaccgt gaggccaacc tcaccagcag cgtgacgata     420
ctgccactgc ctctgcagaa cgccacggtg aagccggca ccagatgcca ggtggccggc     480
tgggggagcc agcgcagtgg ggggcgtctc tcccgttttc ccaggtttgt caacgtgact     540
gtgaccccg aggaccagtg tcgccccaac aacgtgtgca ccggtgtgct cacccgccgc     600
ggtggcatct gcaatgggga cgggggcacc cccctcgtct gcgagggcct ggcccacggc     660
gtggcctcct tttccctggg gccctgtggc cgaggccctg acttcttcac ccgagtggcg     720
ctcttccgag actggatcga tgtgttctc aacaacccgg gaccggggcc agcctagggg     780
ggcctgtgac ctcccatgga gcccagcccc gccctccaca cctccggcgc tccgcaccca     840
cctcccacgg ccccgcccct gccccgctc cggccagagg ggccctggct gtaataaaga     900
agccgatctc tcctctgcaa aaaaaaaaa aaaaaa                                936
```

<210> SEQ ID NO 6
<211> LENGTH: 251
<212> TYPE: PRT
<213> ORGANISM: Homo sapiens

<400> SEQUENCE: 6

```
Met Thr Arg Leu Thr Val Leu Ala Leu Leu Ala Gly Leu Leu Ala Ser
1               5                   10                  15

Ser Arg Ala Gly Ser Ser Pro Leu Leu Asp Ile Val Gly Gly Arg Lys
            20                  25                  30

Ala Arg Pro Arg Gln Phe Pro Phe Leu Ala Ser Ile Gln Asn Gln Gly
        35                  40                  45

Arg His Phe Cys Gly Gly Ala Leu Ile His Ala Arg Phe Val Met Thr
    50                  55                  60

Ala Ala Ser Cys Phe Gln Ser Gln Asn Pro Gly Val Ser Thr Val Val
65                  70                  75                  80

Leu Gly Ala Tyr Asp Leu Arg Arg Arg Glu Arg Gln Ser Arg Gln Thr
                85                  90                  95

Phe Ser Ile Ser Ser Met Ser Glu Asn Gly Tyr Asp Pro Gln Gln Asn
            100                 105                 110

Leu Asn Asp Leu Met Leu Leu Gln Leu Asp Arg Glu Ala Asn Leu Thr
        115                 120                 125

Ser Ser Val Thr Ile Leu Pro Leu Pro Leu Gln Asn Ala Thr Val Glu
    130                 135                 140

Ala Gly Thr Arg Cys Gln Val Ala Gly Trp Gly Ser Gln Arg Ser Gly
```

```
                145                150                155                160
Gly Arg Leu Ser Arg Phe Pro Arg Phe Val Asn Val Thr Val Thr Pro
                    165                170                175

Glu Asp Gln Cys Arg Pro Asn Asn Val Cys Thr Gly Val Leu Thr Arg
                    180                185                190

Arg Gly Gly Ile Cys Asn Gly Asp Gly Thr Pro Leu Val Cys Glu
                195                200                205

Gly Leu Ala His Gly Val Ala Ser Phe Ser Leu Gly Pro Cys Gly Arg
    210                215                220

Gly Pro Asp Phe Phe Thr Arg Val Ala Leu Phe Arg Asp Trp Ile Asp
225                230                235                240

Gly Val Leu Asn Asn Pro Gly Pro Gly Pro Ala
                    245                250

<210> SEQ ID NO 7
<211> LENGTH: 1901
<212> TYPE: DNA
<213> ORGANISM: Homo sapiens

<400> SEQUENCE: 7
```

| | | | | | |
|---|---|---|---|---|---|
| ccgactcttt | tatagctccc | tggttcaacc | tcaaggcctt | gaggttttgg | cagctctgga | 60 |
| ggatgagaga | gaacatggcc | aggggcccct | gcaacgcgcc | gagatgggcg | tccctgatgg | 120 |
| tgctggtcgc | cataggcacc | gccgtgacag | cggccgtcaa | ccctggcgtc | gtggtcagga | 180 |
| tctcccagaa | gggcctggac | tacgccagcc | agcagggac | ggccgctctg | cagaaggagc | 240 |
| tgaagaggat | caagattcct | gactactcag | acagctttaa | gatcaagcat | cttgggaagg | 300 |
| ggcattatag | cttctacagc | atggacatcc | gtgaattcca | gcttcccagt | tcccagataa | 360 |
| gcatggtgcc | aatgtgggc | cttaagttct | ccatcagcaa | cgccaatatc | aagatcagcg | 420 |
| ggaaatggaa | ggcacaaaag | agattcttaa | aaatgagcgg | caatttgac | ctgagcatag | 480 |
| aaggcatgtc | catttcggct | gatctgaagc | tgggcagtaa | ccccacgtca | ggcaagccca | 540 |
| ccatcacctg | ctccagctgc | agcagccaca | tcaacagtgt | ccacgtgcac | atctcaaaga | 600 |
| gcaaagtggg | gtggctgatc | caactcttcc | acaaaaaaat | tgagtctgcg | cttcgaaaca | 660 |
| agatgaacag | ccaggtctgc | gagaaagtga | ccaattctgt | atcctccgag | ctgcaacctt | 720 |
| atttccagac | tctgccagta | atgaccaaaa | tagattctgt | ggctggaatc | aactatggtc | 780 |
| tggtggcacc | tccagcaacc | acggctgaga | ccctggatgt | acagatgaag | ggggagtttt | 840 |
| acagtgagaa | ccaccacaat | ccacctccct | ttgctccacc | agtgatggag | tttcccgctg | 900 |
| cccatgaccg | catggtatac | ctgggcctct | cagactactt | cttcaacaca | gccgggcttg | 960 |
| tataccaaga | ggctggggtc | ttgaagatga | cccttagaga | tgacatgatt | ccaaaggagt | 1020 |
| ccaaatttcg | actgacaacc | aagttctttg | gaaccttcct | acctgaggtg | gccaagaagt | 1080 |
| ttcccaacat | gaagatacag | atccatgtct | cagcctccac | cccgccacac | ctgtctgtgc | 1140 |
| agcccaccgg | ccttaccttc | taccctgccg | tggatgtcca | ggcctttgcc | gtcctcccca | 1200 |
| actcctccct | ggcttccctc | ttcctgattg | gcatgcacac | aactggttcc | atggaggtca | 1260 |
| gcgccgagtc | caacaggctt | gttggagagc | tcaagctgga | taggctgctc | ctggaactga | 1320 |
| agcactcaaa | tattggcccc | ttccggttg | aattgctgca | ggatatcatg | aactacattg | 1380 |
| tacccattct | tgtgctgccc | agggttaacg | agaaactaca | gaaaggcttc | cctctcccga | 1440 |
| cgccggccag | agtccagctc | tacaacgtag | tgcttcagcc | tcaccagaac | ttcctgctgt | 1500 |
| tcggtgcaga | cgttgtctat | aaatgaaggc | accaggggtg | ccggggctg | tcagccacac | 1560 |

```
ctgttcctga tgggctgtgg ggcaccggct gcctttcccc agggaatcct ctccagatct    1620
taaccaagag ccccttgcaa acttcttcga ctcagattca gaaatgatct aaacacgagg    1680
aaacattatt cattggaaaa gtgcatggtg tgtattttag ggattatgag cttctttcaa    1740
gggctaaggc tgcagagata tttcctccag gaatcgtgtt tcaattgtaa ccaagaaatt    1800
tccatttgtg cttcatgaaa aaaaacttct ggttttttc atgtgaaaaa aaaaaaaaa    1860 aaaaaaaaa aaaaaaaaa aaaaaaaaa aaaaaaaaa a                          1901
```

<210> SEQ ID NO 8
<211> LENGTH: 487
<212> TYPE: PRT
<213> ORGANISM: Homo sapiens

<400> SEQUENCE: 8

```
Met Arg Glu Asn Met Ala Arg Gly Pro Cys Asn Ala Pro Arg Trp Ala
1               5                   10                  15

Ser Leu Met Val Leu Val Ala Ile Gly Thr Ala Val Thr Ala Ala Val
                20                  25                  30

Asn Pro Gly Val Val Arg Ile Ser Gln Lys Gly Leu Asp Tyr Ala
            35                  40                  45

Ser Gln Gln Gly Thr Ala Ala Leu Gln Lys Glu Leu Lys Arg Ile Lys
    50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
    130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Glu Leu Gln Pro Tyr Phe Gln Thr Leu
    210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Phe Ala Pro
            260                 265                 270

Pro Val Met Glu Phe Pro Ala Ala His Asp Arg Met Val Tyr Leu Gly
        275                 280                 285

Leu Ser Asp Tyr Phe Phe Asn Thr Ala Gly Leu Val Tyr Gln Glu Ala
    290                 295                 300

Gly Val Leu Lys Met Thr Leu Arg Asp Asp Met Ile Pro Lys Glu Ser
```

```
                305                 310                 315                 320
        Lys Phe Arg Leu Thr Thr Lys Phe Phe Gly Thr Phe Leu Pro Glu Val
                        325                 330                 335

Ala Lys Lys Phe Pro Asn Met Lys Ile Gln Ile His Val Ser Ala Ser
                        340                 345                 350

Thr Pro Pro His Leu Ser Val Gln Pro Thr Gly Leu Thr Phe Tyr Pro
                        355                 360                 365

Ala Val Asp Val Gln Ala Phe Ala Val Leu Pro Asn Ser Ser Leu Ala
                370                 375                 380

Ser Leu Phe Leu Ile Gly Met His Thr Thr Gly Ser Met Glu Val Ser
        385                 390                 395                 400

Ala Glu Ser Asn Arg Leu Val Gly Glu Leu Lys Leu Asp Arg Leu Leu
                        405                 410                 415

Leu Glu Leu Lys His Ser Asn Ile Gly Pro Phe Pro Val Glu Leu Leu
                        420                 425                 430

Gln Asp Ile Met Asn Tyr Ile Val Pro Ile Leu Val Leu Pro Arg Val
                        435                 440                 445

Asn Glu Lys Leu Gln Lys Gly Phe Pro Leu Pro Thr Pro Ala Arg Val
                450                 455                 460

Gln Leu Tyr Asn Val Val Leu Gln Pro His Gln Asn Phe Leu Leu Phe
        465                 470                 475                 480

Gly Ala Asp Val Val Tyr Lys
                        485

<210> SEQ ID NO 9
<211> LENGTH: 1020
<212> TYPE: DNA
<213> ORGANISM: Homo sapiens

<400> SEQUENCE: 9
gggagaggaa gtggagggcg ctggccggcc gtggggcaat gcaacggcct cccagcacag      60
ggctataaga ggagccgggc gggcacggag gggcagagac cccggagccc cagccccacc     120
atgaccctcg gccgccgact cgcgtgtctt ttcctcgcct gtgtcctgcc ggccttgctg     180
ctgggggggca ccgcgctggc ctcggagatt gtgggggggcc ggcgagcgcg gccccacgcg     240
tggcccttca tggtgtccct gcagctgcgc ggaggccact tctgcggcgc caccctgatt     300
gcgcccaact tcgtcatgtc ggccgcgcac tgcgtggcga atgtaaacgt ccgcgcggtg     360
cgggtggtcc tgggagccca taacctctcg cggcgggagc ccaccggca ggtgttcgcc      420
gtgcagcgca tcttcgaaaa cggctacgac cccgtaaact gctcaacga catcgtgatt      480
ctccagctca cgggtcggc caccatcaac gccaacgtgc aggtggccca gctgccggct     540
cagggacgcc gcctgggcaa cggggtgcag tgcctggcca tgggctgggg ccttctgggc     600
aggaaccgtg ggatcgccag cgtcctgcag gagctcaacg tgacggtggt gacgtccctc     660
tgccgtcgca gcaacgtctg cactctcgtg aggggccggc aggccggcgt ctgtttcggg     720
gactccggca gccccttggt ctgcaacggg ctaatccacg gaattgcctc cttcgtccgg     780
ggaggctgcg cctcagggct ctaccccgat gcctttgccc cggtggcaca gtttgtaaac     840
tggatcgact ctatcatcca acgctccgag gacaaccccg tccccaccc ccgggacccg       900
gacccggcca gcaggaccca ctgagaaggg ctgcccgggt cacctcagct gcccacaccc     960
acactctcca gcatctggca caataaacat tctctgtttt gtagaaaaaa aaaaaaaaaa    1020

<210> SEQ ID NO 10
```

<211> LENGTH: 267
<212> TYPE: PRT
<213> ORGANISM: Homo sapiens

<400> SEQUENCE: 10

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
        35                  40                  45

Leu Arg Gly Gly His Phe Cys Gly Ala Thr Leu Ile Ala Pro Asn Phe
    50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
        115                 120                 125

Ile Asn Ala Asn Val Gln Val Ala Gln Leu Pro Ala Gln Gly Arg Arg
    130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His
            260                 265

<210> SEQ ID NO 11
<211> LENGTH: 2648
<212> TYPE: DNA
<213> ORGANISM: Homo sapiens

<400> SEQUENCE: 11
gactcctagg ggcttgcaga ctagtgggag agaaagaaca tcgcagcagc caggcagaac      60
caggacaggt gaggtgcagg ctggctttcc tctcgcagcg cggtgtggag tcctgtcctg     120
cctcagggct tttcggagcc tggatcctca aggaacaagt agacctggcc gcggggagtg     180
gggagggaag gggtgtctat tgggcaacag ggcggggcaa agccctgaat aaaggggcgc     240
agggcaggcg caagtggcag agccttcgtt tgccaagtcg cctccagacc gcagacatga     300
aacttgtctt cctcgtcctg ctgttcctcg ggccctcgg actgtgtctg ctggccgta      360 ggaggagtgt tcagtggtgc gccgtatccc aacccgaggc cacaaaatgc ttccaatggc     420

```
aaaggaatat gagaaaagtg cgtggccctc ctgtcagctg cataaagaga gactccccca    480
tccagtgtat ccaggccatt gcggaaaaca gggccgatgc tgtgacccctt gatggtggtt   540 tcatatacga ggcaggcctg ccccctaca  aactgcgacc tgtagcggcg aagtctacg     600 ggaccgaaag acagccacga actcactatt atgccgtggc tgtggtgaag aagggcggca    660
gctttcagct gaacgaactg caaggtctga agtcctgcca cacaggcctt cgcaggaccg    720
ctggatggaa tgtccctata gggacacttc gtccattctt gaattggacg ggtccacctg    780
agcccattga ggcagctgtg ccaggttct  tctcagccag ctgtgttccc ggtgcagata    840
aaggacagtt ccccaacctg tgtcgcctgt gtgcggggac aggggaaaac aaatgtgcct    900
tctcctccca ggaaccgtac ttcagctact ctggtgcctt caagtgtctg agagacgggg    960
ctggagacgg ggcttttatc agagagagca cagtgtttga ggacctgtca gacgaggctg   1020
aaagggacga gtatgagtta ctctgcccag acaacactcg gaagccagtg acaagttca    1080 aagactgcca tctggcccgg gtcccttctc atgccgttgt ggcacgaagt gtgaatggca   1140
aggaggatgc catctggaat cttctccgcc aggcacagga aaagtttgga aaggacaagt   1200
caccgaaatt ccagctcttt ggctcccta  gtgggcagaa agatctgctg ttcaaggact   1260
ctgccattgg gttttcgagg gtgcccccga ggatagattc tgggctgtac cttggctccg   1320
gctacttcac tgccatccag aacttgagga aaagtgagga ggaagtggct gcccggcgtg   1380
cgcgggtcgt gtggtgtgcg gtgggcgagc aggagctgcg caagtgtaac cagtggagtg   1440
gcttgagcga aggcagcgtg acctgctcct cggcctccac cacagaggac tgcatcgccc   1500
tggtgctgaa aggagaagct gatgccatga gtttggatgg aggatatgtg tacactgcag   1560
gcaaatgtgg tttggtgcct gtcctggcag agaactacaa atcccaacaa agcagtgacc   1620
ctgatcctaa ctgtgtggat agacctgtgg aaggatatct tgctgtggcg gtggttagga   1680
gatcagacac tagccttacc tggaactctg tgaaaggcaa gaagtcctgc cacaccgccg   1740
tggacaggac tgcaggctgg aatatcccca tgggcctgct cttcaaccag acgggctcct   1800
gcaaatttga tgaatatttc agtcaaagct gtgcccctgg gtctgacccg agatctaatc   1860
tctgtgctct gtgtattggc gacgagcagg gtgagaataa gtgcgtgccc aacagcaacg   1920
agagatacta cggctacact ggggctttcc ggtgcctggc tgagaatgct ggagacgttg   1980
catttgtgaa agatgtcact gtcttgcaga acactgatgg aaataacaat gaggcatggg   2040
ctaaggattt gaagctggca gactttgcgc tgctgtgcct cgatggcaaa cggaagcctg   2100
tgactgaggc tagaagctgc catcttgcca tggccccgaa tcatgccgtg tgtctcgga   2160 tggataaggt ggaacgcctg aaacaggtgt tgctccacca acaggctaaa tttgggagaa   2220
atggatctga ctgcccggac aagttttgct tattccagtc tgaaaccaaa aaccttctgt   2280
tcaatgacaa cactgagtgt ctggccagac tccatggcaa acaacatat  gaaaaatatt   2340 tgggaccaca gtatgtcgca ggcattacta atctgaaaaa gtgctcaacc tccccctcc    2400 tggaagcctg tgaattcctc aggaagtaaa accgaagaag atggcccagc tcccaagaa    2460 agcctcagcc attcactgcc cccagctctt ctccccaggt gtgttgggc  cttggcctcc    2520 cctgctgaag gtggggattg cccatccatc tgcttacaat tccctgctgt cgtcttagca   2580
agaagtaaaa tgagaaattt tgttgatatt ctctccttaa aaaaaaaaaa aaaaaaaaa    2640 aaaaaaaa                                                            2648
```

<210> SEQ ID NO 12
<211> LENGTH: 710

<212> TYPE: PRT
<213> ORGANISM: Homo sapiens

<400> SEQUENCE: 12

```
Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser Gln
            20                  25                  30

Pro Glu Ala Thr Lys Cys Phe Gln Trp Gln Arg Asn Met Arg Lys Val
        35                  40                  45

Arg Gly Pro Pro Val Ser Cys Ile Lys Arg Asp Ser Pro Ile Gln Cys
    50                  55                  60

Ile Gln Ala Ile Ala Glu Asn Arg Ala Asp Ala Val Thr Leu Asp Gly
65                  70                  75                  80

Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
    130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205

Phe Ser Tyr Ser Gly Ala Phe Lys Cys Leu Arg Asp Gly Ala Gly Asp
    210                 215                 220

Val Ala Phe Ile Arg Glu Ser Thr Val Phe Glu Asp Leu Ser Asp Glu
225                 230                 235                 240

Ala Glu Arg Asp Glu Tyr Glu Leu Leu Cys Pro Asp Asn Thr Arg Lys
                245                 250                 255

Pro Val Asp Lys Phe Lys Asp Cys His Leu Ala Arg Val Pro Ser His
            260                 265                 270

Ala Val Val Ala Arg Ser Val Asn Gly Lys Glu Asp Ala Ile Trp Asn
        275                 280                 285

Leu Leu Arg Gln Ala Gln Glu Lys Phe Gly Lys Asp Lys Ser Pro Lys
    290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                325                 330                 335

Leu Tyr Leu Gly Ser Gly Tyr Phe Thr Ala Ile Gln Asn Leu Arg Lys
            340                 345                 350

Ser Glu Glu Glu Val Ala Ala Arg Arg Ala Arg Val Val Trp Cys Ala
        355                 360                 365

Val Gly Glu Gln Glu Leu Arg Lys Cys Asn Gln Trp Ser Gly Leu Ser
    370                 375                 380

Glu Gly Ser Val Thr Cys Ser Ser Ala Ser Thr Thr Glu Asp Cys Ile
385                 390                 395                 400
```

Ala Leu Val Leu Lys Gly Glu Ala Asp Ala Met Ser Leu Asp Gly Gly
                405                 410                 415

Tyr Val Tyr Thr Ala Gly Lys Cys Gly Leu Val Pro Val Leu Ala Glu
            420                 425                 430

Asn Tyr Lys Ser Gln Gln Ser Ser Asp Pro Asp Pro Asn Cys Val Asp
        435                 440                 445

Arg Pro Val Glu Gly Tyr Leu Ala Val Ala Val Arg Arg Ser Asp
450                 455                 460

Thr Ser Leu Thr Trp Asn Ser Val Lys Gly Lys Ser Cys His Thr
465                 470                 475                 480

Ala Val Asp Arg Thr Ala Gly Trp Asn Ile Pro Met Gly Leu Leu Phe
                485                 490                 495

Asn Gln Thr Gly Ser Cys Lys Phe Asp Glu Tyr Phe Ser Gln Ser Cys
            500                 505                 510

Ala Pro Gly Ser Asp Pro Arg Ser Asn Leu Cys Ala Leu Cys Ile Gly
        515                 520                 525

Asp Glu Gln Gly Glu Asn Lys Cys Val Pro Asn Ser Asn Glu Arg Tyr
    530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
                565                 570                 575

Asn Asn Glu Ala Trp Ala Lys Asp Leu Lys Leu Ala Asp Phe Ala Leu
            580                 585                 590

Leu Cys Leu Asp Gly Lys Arg Lys Pro Val Thr Glu Ala Arg Ser Cys
        595                 600                 605

His Leu Ala Met Ala Pro Asn His Ala Val Val Ser Arg Met Asp Lys
    610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu
                645                 650                 655

Thr Lys Asn Leu Leu Phe Asn Asp Asn Thr Glu Cys Leu Ala Arg Leu
            660                 665                 670

His Gly Lys Thr Thr Tyr Glu Lys Tyr Leu Gly Pro Gln Tyr Val Ala
        675                 680                 685

Gly Ile Thr Asn Leu Lys Lys Cys Ser Thr Ser Pro Leu Leu Glu Ala
    690                 695                 700

Cys Glu Phe Leu Arg Lys
705                 710

<210> SEQ ID NO 13
<211> LENGTH: 501
<212> TYPE: DNA
<213> ORGANISM: Homo sapiens

<400> SEQUENCE: 13

```
ccttgctata gaagacctgg gacagaggac tgctgtctgc cctctctggt caccctgcct      60
agctagagga tctgtgaccc cagccatgag gaccctcgcc atccttgctg ccattctcct     120
ggtggccctg caggcccagg ctgagccact ccaggcaaga gctgatgagg ttgctgcagc     180
cccggagcag attgcagcgg acatcccaga agtggttgtt tcccttgcat gggacgaaag     240
cttggctcca aagcatccag gctcaaggaa aaacatggac tgctattgca gaataccagc     300
```

```
gtgcattgca ggagaacgtc gctatggaac ctgcatctac cagggaagac tctgggcatt        360
ctgctgctga gcttgcagaa aaagaaaaat gagctcaaaa tttgctttga gagctacagg        420
gaattgctat tactcctgta ccttctgctc aatttccttt cctcatctca aataaatgcc        480
ttgttacaag aaaaaaaaaa a                                                  501
```

<210> SEQ ID NO 14
<211> LENGTH: 94
<212> TYPE: PRT
<213> ORGANISM: Homo sapiens

<400> SEQUENCE: 14

```
Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
                20                  25                  30

Pro Glu Gln Ile Ala Ala Asp Ile Pro Glu Val Val Ser Leu Ala
        35                  40                  45

Trp Asp Glu Ser Leu Ala Pro Lys His Pro Gly Ser Arg Lys Asn Met
    50                  55                  60

Asp Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90
```

<210> SEQ ID NO 15
<211> LENGTH: 863
<212> TYPE: DNA
<213> ORGANISM: Homo sapiens

<400> SEQUENCE: 15

```
agggccaccc aggtgagcct ctcactcgcc acctcctctt ccaccccctgc caggcccagc        60 agccaccaca gcgcctgctt cctcggccct gaaatcatgc ccctaggtct cctgtggctg       120
ggcctagccc tgttgggggc tctgcatgcc caggcccagg actccacctc agacctgatc       180
ccagccccac ctctgagcaa ggtccctctg cagcagaact ccaggacaa ccaattccag       240 gggaagtggt atgtggtagg cctggcaggg aatgcaattc tcagagaaga caaagacccg       300
caaaagatgt atgccaccat ctatgagctg aaagaagaca gagctacaa tgtcacctcc       360 gtcctgtttta ggaaaaagaa gtgtgactac tggatcagga cttttgttcc aggttgccag       420
cccggcgagt tcacgctggg caacattaag agttaccctg gattaacgag ttacctcgtc       480
cgagtggtga gcaccaacta caaccagcat gctatggtgt tcttcaagaa gtttctcaa        540 aacagggagt acttcaagat caccctctac gggagaacca aggagctgac ttcggaacta       600
aaggagaact tcatccgctt ctccaaatct ctgggcctcc ctgaaaacca tcgtcttc        660 cctgtcccaa tcgaccagtg tatcgacggc tgagtgcaca ggtgccgcca gctgccgcac       720
cagcccgaac accattgagg gagctgggag accctcccca cagtgccacc catgcagctg       780
ctccccaggc caccccgctg atggagcccc accttgtctg ctaaataaac atgtgccctc       840
aggccaaaaa aaaaaaaaaa aaa                                                863
```

<210> SEQ ID NO 16
<211> LENGTH: 198
<212> TYPE: PRT
<213> ORGANISM: Homo sapiens

<400> SEQUENCE: 16

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
        50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
            195

<210> SEQ ID NO 17
<211> LENGTH: 758
<212> TYPE: DNA
<213> ORGANISM: Homo sapiens

<400> SEQUENCE: 17
gtcctgtgaa gcaatagcca ggggctaaag caaaccccag cccacaccct ggcaggcagc      60
cagggatggg tggatcagga aggctcctgg ttgggctttt gcatcaggct caggctgggc     120
ataaaggagg ctcctgtggg ctagagggag gcagacatgg ggaccatgaa gacccaaagg     180
gatggccact ccctggggcg gtggtcactg gtgctcctgc tgctgggcct ggtgatgcct     240
ctggccatca ttgcccaggt cctcagctac aaggaagctg tgcttcgtgc tatagatggc     300
atcaaccagc ggtcctcgga tgctaacctc taccgcctcc tggacctgga ccccaggccc     360
acgatggatg ggacccagag cacgccaaag cctgtgagct tcacagtgaa ggagacagtg     420
tgccccagga cgacacagca gtcaccagag gattgtgact tcaagaagga cgggctggtg     480
aagcggtgta tggggacagt gaccctcaac caggccaggg gctcctttga catcagttgt     540
gataaggata caagagatt tgccctgctg ggtgatttct tccggaaatc taaagagaag     600
attggcaaag agtttaaaag aattgtccag agaatcaagg attttttgcg gaatcttgta     660
cccaggacag agtcctagtg tgtgccctac cctggctcag gcttctgggc tctgagaaat     720
aaactatgag agcaatttcc tcaggaaaaa aaaaaaaa                              758

<210> SEQ ID NO 18
<211> LENGTH: 173
<212> TYPE: PRT
<213> ORGANISM: Homo sapiens

<400> SEQUENCE: 18

```
Met Gly Thr Met Lys Thr Gln Arg Asp Gly His Ser Leu Gly Arg Trp
1               5                   10                  15

Ser Leu Val Leu Leu Leu Gly Leu Val Met Pro Leu Ala Ile Ile
            20                  25                  30

Ala Gln Val Leu Ser Tyr Lys Glu Ala Val Leu Arg Ala Ile Asp Gly
            35                  40                  45

Ile Asn Gln Arg Ser Ser Asp Ala Asn Leu Tyr Arg Leu Leu Asp Leu
    50                  55                  60

Asp Pro Arg Pro Thr Met Asp Gly Asp Pro Thr Pro Lys Pro Val
65                  70                  75                  80

Ser Phe Thr Val Lys Glu Thr Val Cys Pro Arg Thr Thr Gln Gln Ser
                85                  90                  95

Pro Glu Asp Cys Asp Phe Lys Lys Asp Gly Leu Val Lys Arg Cys Met
            100                 105                 110

Gly Thr Val Thr Leu Asn Gln Ala Arg Gly Ser Phe Asp Ile Ser Cys
            115                 120                 125

Asp Lys Asp Asn Lys Arg Phe Ala Leu Leu Gly Asp Phe Phe Arg Lys
130                 135                 140

Ser Lys Glu Lys Ile Gly Lys Glu Phe Lys Arg Ile Val Gln Arg Ile
145                 150                 155                 160

Lys Asp Phe Leu Arg Asn Leu Val Pro Arg Thr Glu Ser
                165                 170
```

<210> SEQ ID NO 19
<211> LENGTH: 119
<212> TYPE: PRT
<213> ORGANISM: Artificial sequence
<220> FEATURE:
<223> OTHER INFORMATION: Heavy chain variable region

<400> SEQUENCE: 19

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115
```

<210> SEQ ID NO 20
<211> LENGTH: 107
<212> TYPE: PRT
<213> ORGANISM: Artificial sequence
<220> FEATURE:
<223> OTHER INFORMATION: Light chain variable region

<400> SEQUENCE: 20

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105
```

<210> SEQ ID NO 21
<211> LENGTH: 443
<212> TYPE: PRT
<213> ORGANISM: Artificial sequence
<220> FEATURE:
<223> OTHER INFORMATION: Heavy chain

<400> SEQUENCE: 21

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
            435                 440

<210> SEQ ID NO 22
<211> LENGTH: 214
<212> TYPE: PRT
<213> ORGANISM: Artificial sequence
<220> FEATURE:
<223> OTHER INFORMATION: Light chain

<400> SEQUENCE: 22

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 21
<212> TYPE: DNA
<213> ORGANISM: Artificial Sequence
<220> FEATURE:
<223> OTHER INFORMATION: an artificially synthesized sequence

<400> SEQUENCE: 23
cactcttcca gccttccttc c                                        21

<210> SEQ ID NO 24
<211> LENGTH: 21
<212> TYPE: DNA
<213> ORGANISM: Artificial Sequence
<220> FEATURE:
<223> OTHER INFORMATION: an artificially synthesized sequence

<400> SEQUENCE: 24
gcgtacaggt ctttgcggat g                                        21
```